United States Patent
Gjerde et al.

(12)

(10) Patent No.: US 6,455,692 B1
(45) Date of Patent: Sep. 24, 2002

(54) METHOD OF CONCENTRATING POLYNUCLEOTIDES USING MIPC

(75) Inventors: Douglas T. Gjerde, Saratoga; Paul D. Taylor, Gilroy; Robert M. Haefele, Campbell, all of CA (US)

(73) Assignee: Transgenomic, Inc., San Jose, CA (US)

( * ) Notice: Subject to any disclaimer, the term of this patent is extended or adjusted under 35 U.S.C. 154(b) by 0 days.

(21) Appl. No.: 09/698,938

(22) Filed: Oct. 26, 2000

Related U.S. Application Data

(63) Continuation of application No. 09/129,105, filed on Aug. 4, 1998, now Pat. No. 6,287,822.

(51) Int. Cl.$^7$ .................. C07H 21/04; C07H 21/02; C12Q 1/68; C12Q 19/34; B01D 15/01
(52) U.S. Cl. .............. 536/254; 536/22.1; 536/23.1; 435/6; 435/7.1; 435/91.1; 435/91.2; 210/656; 210/635; 210/198.2
(58) Field of Search .................. 435/6, 91.1, 91.2; 536/22.1, 23.1, 25.4; 210/656, 635, 198.2

(56) References Cited

U.S. PATENT DOCUMENTS

| | | | |
|---|---|---|---|
| 3,826,905 A | 7/1974 | Valkama et al. | 235/151.12 |
| 3,917,527 A | 11/1975 | Shaltiel | 210/31 |
| 4,683,202 A | 7/1987 | Mullis | 435/91 |
| 5,024,934 A | 6/1991 | Lee et al. | 435/6 |
| 5,100,547 A | 3/1992 | Hardiman et al. | 210/198.2 |
| 5,203,992 A | 4/1993 | Drouen et al. | 210/198.2 |
| 5,205,929 A | 4/1993 | Carr et al. | 210/198.2 |
| 5,207,914 A | 5/1993 | Lin | 210/635 |
| 5,217,863 A | 6/1993 | Cotton et al. | 435/6 |
| 5,334,310 A | 8/1994 | Frechet et al. | 210/198.2 |
| 5,340,452 A | 8/1994 | Brenner et al. | 204/180.1 |
| 5,446,147 A * | 8/1995 | Kung et al. | 540/595 |
| 5,453,185 A | 9/1995 | Frechet et al. | 210/198.2 |
| 5,508,204 A | 4/1996 | Norman | 436/161 |
| 5,522,994 A | 6/1996 | Frechet et al. | 210/635 |
| 5,527,676 A | 6/1996 | Vogelstein et al. | 435/6 |
| 5,550,025 A | 8/1996 | Walker | 435/6 |
| 5,585,236 A | 12/1996 | Bonn et al. | 435/5 |
| 5,654,144 A | 8/1997 | Mann et al. | 435/6 |
| 5,695,971 A | 12/1997 | Kadokami et al. | 435/172.1 |
| 5,728,526 A | 3/1998 | George, Jr. et al. | 435/6 |
| 5,763,178 A | 6/1998 | Chirikjian et al. | 435/6 |
| 5,766,888 A | 6/1998 | Sobol et al. | 435/91.2 |
| 5,772,889 A | 6/1998 | Gjerde et al. | 210/635 |
| 5,789,153 A | 8/1998 | Falkner et al. | 435/5 |
| 5,795,976 A | 8/1998 | Oefner et al. | 536/25.4 |
| 5,969,228 A | 10/1999 | Gorenstein | 73/23.22 |
| 6,066,258 A * | 5/2000 | Gjerde et al. | 210/635 |
| 6,207,378 B1 | 3/2001 | Yamane et al. | 435/6 |

FOREIGN PATENT DOCUMENTS

| | | | |
|---|---|---|---|
| EP | 0 507 591 A2 | 10/1992 | B01J/41/06 |
| WO | 95/29258 | 11/1995 | C12Q/1/68 |
| WO | 98/40395 | 9/1998 | C07H/21/04 |
| WO | 99/47710 | 9/1999 | C12Q/1/68 |
| WO | 99/54498 | 10/1999 | C12Q/1/68 |
| WO | 00/34652 | 6/2000 | F04B/1/14 |
| WO | 00/66772 | 11/2000 | C12Q/1/68 |

OTHER PUBLICATIONS

Andre et al, Fidelity an Mutational Spectrum of PFU DNA Polymerase On A Human Mitochondrial DNA Sequence, Genome Research No. 7:843–852 (1997).*

Apffel et al. Applications of HPLC for the Analysis of Doublse Stranded DNA Use of Wide Pore Sisilca Based Materials, ISPPP'97 17th International Symposium on Separation of Proteins, Peptids & Polynucleotides, Oct. 26–29, 1997.*

Arnold et al, A Highly Sensitive Fast and Economical Technique for Mutation Analysis in Hereditary Breast and Ovarian Cancers, Humnan Mutation 14:333–339 (1999).*

Barder et al. Fast Chromatography and Nonporous Silica, LC–GC (1997) 15: 918–926, No. 10.*

Barros et al, Double– and Single–Strand Conformation Polymorphism Analysis of Point Mutations and Short Tandem Repeats, Electrophoresis, 15: 566–571 (1994).*

Belenky et al, High–Thoughput Bioplymer Desalting Prior to Mass Spectrometry Using 96–Well Solid–Phase Extraction Plates, DNA 2000 International Symposium on the State–Of–The–Art in Genetic Analysis.*

Bernardi, Chromatrography of Nucleic Acids on Hodroxyapatite Columns Methods of Enzymology, vol. XXI, pp. 95–147, 1971.*

Berti, Dissertation, Untersuchungen Zur Ionenpaar–Umkehrphasen–Chromatographie Von DNA, Jun. 1996, pp. 52–53.*

Bischoff et al, Isolation of Specific TRNAS Using an Ionic–Hydrophobic Mixed–Mode Chromatographic Matrix, Analytical Biochemistry, 151: 526–533 (1985).*

Brossette et al, A Program for Selecting DNA Framents to Detect Mutations by Denaturing Gel Electrophoresis Methods, Nueleic Acids Research, 1994. vol. 22, No. 20 4321–4325.*

(List continued on next page.)

*Primary Examiner*—Jeffrey Siew
(74) *Attorney, Agent, or Firm*—William B. Walker

(57) ABSTRACT

The present invention is directed to improved methods for detection of mutations in DNA using Denaturing Matched Ion Polynucleotide Chromatography (DMIPC). The invention includes the following aspects: analysis of PCR amplification products to identify factors that affect PCR replication fidelity; design of PCR primers; selection of an optimal temperature for performing DMIPC; selection of the mobile phase composition for gradient elution; methods for column preparation and maintenance; and methods for preparing polynucleotide samples prior to chromatographic analysis.

7 Claims, 21 Drawing Sheets

OTHER PUBLICATIONS

Cadwell et al, Randomization of Genes by PCR Mutagenesis, PCR Methods and Applications, vol. 2 pp. 28–33, Cold Spring Harbor Laboratory (1992).*

Chen et al. High–Speed High–Performance Liquid Chromatography of Peptides and Proteins, J. of Chromatography A (1995) 705: 3–20.*

Coenen et al. Optimization of the Separation of the PR and SP Diasteromers of Phsphate–Methylated DNA and RNA Dinuleotides, Journal of Chromatography, 596, 59–66, (1992).*

Cotton et al, Slowly by Surely Toward Better Scanning For Mutations, TIG, vol. 13, No. 2: 43–46 (Feb. 1997).*

Cotton, Richard G.H., Mutation Detection. Ch. 3.2 Mismatch Cleavage or Bindings Assays pp. 67–95.*

DHPLC Workshop, Stanford University, CA, pp. 32–43 (Mar. 17, 1997).*

Dierick et al, Incorporation of DITP or 7–DEAZA DGTP During PCR Improves Sequencing of the Product, Nucleic Acids Research, vol. 21 No. 18: 4427–4428 (1993).*

Djordjevic et al, HPLC Separation of Oligonucleotides in Isocratic and Temperature–Programming Mode, Analytical Chemistry, 70: 1921–1925 (1988).*

Doris et al, Q–RT–PCR: Data Analysis Sofrware for Measurement of Gene Expression by Competitive RT–PCR, vol. 13 No. 6: 587–591 (1997).*

Doris et al. Quantitative Analysis of Gene Expression by Ion Pair HPLC, Handout of DHPLC Workshop, Stanford University (Mar. 17, 1997).*

Doris et al., Quantitative Analysis of Gene Expression by Ion–Pair High–Performance Liquid Chromatography, Journal of Chromatography (1988) 806: 47–60.*

Echert et al. The Fidelity of DNA Polymerases Used in the Polymerase Chain Reactions, pp. 225–240.*

Engelhardt et al. Polymer Encapsulated Stationary Phases: Advantages, Properties and Selectivities, Chromatographia (1989) 27: 535–543, No. 1112.

Erikkson et al, Separation of DNA Restriction Fragments by Ion–Pair Chromatography, Journal of Chromatography, 359: 265–274 (1986).

Fixman et al, Theory of DNA Melting Curves, Biopolymers, 16: 2693–2704 (1977).

Frey et al, Demonstration of the Expand PCR System's Greater Fidelity and Higher Yields with A LACL–Based PCR Fidelity Assay, Biochemica, No. 2 (1995).

Fritz et al. High–Perofrmance Liquid Chromatography in Polynucleotide Synthesis, Biochemistry 17, 7, pp. 1257–1267, (1978).

Fromant et al, Effects of DNTP and Divalent Metal Ion Concentrations on Random PCR Mutagenesis, Genetic Engineering with PCR, Horizon Scientifiec Press, Wymondham, U.K. (1998).

Furst et al. Simultaneous Determination of Myocardial Nucleotides, Nucleosides, Purine Bases and Creatine Phosphate by Ion–Pair High–Performance Liquid Chrmatography, J. Chromatography, 578, 39–44, Jul. 1, 1992.

Gelfi et al, Detection of Point Mutations by Capillary Electrophoresis in Liquid Polymers in Temporal Thermal Gradients, Electrophoresis, 15: 1506–1511 (1994).

Giordano et al, Identification by Denaturing High–Performance Liquid Chromatography of Numerous Polymorphisms in a Canidate Region for Multiple Sclerosis Susceptibility, 56, 247–253 (1999).

Green et al. HPLC Purification of Synthetic Oligodeoxyribonucleotides Contatining Base– and Backbone–Modified Sequences, BioTecnhniques 19:836–841 (Nov. 1993).

Green et al. Preparative Purification F Sypercoiled Plasmid DNA for Therapeutic Applications, BioPharm, 10:5 pp. 52–62, May 1997.

Gross et al, A Comparison of BRCA1 Mutation Analysis by Direct Sequencing, SSCP and DHPLC, Hum Genet (1999) 105:72–78.

Hayward et al., Modeling and Analysis of Competitive RT–PCR, Nucleic Acids Res. (1998) 26:2511–2518, No. 11.

Hayward–Lester et al, Accurate and Absolute Quantitative Measurement of Gene Expression by Single–Tube RT–PCR and HPLC, Genome Research, No. 5: 494–499 (1995).

Hayward–Lester et al. Rapid Quantification of Gene Expression by Competitive RT–PCR and Ion–Pair Reversed Phase HPLC, BioTechniques (1996) 20: 250–257.

Hayward–Lester et al., Quantification of Specific Nucleic Acids, Regulated RNA Processing and Genomic Polymorphisms Using Reversed–Phase HPLC.

Heftman, Chromatogrphay, 5th Edition, Journal of Chromatography Library—Vol. 51A, Elsevier, pp. A299–A300, 1992.

Hewlett–Packard, ZORBAX Stable Bond ZORBAX Eclipse Reverse Phase HPLC Columns, Product Specification.

Hirabayashi et al. Size–Dependent Chromatographic Separation of Double–Stranded DNA Which is not Based on Gel Permeation Mode, Analytical Biochemistry 178, 336–341, 1989.

Hirabayashi, Slalom Chromatography: Size–Dependent Separation of DN Molecles by a Hudrodynamic Phenomenon, Biochemistry (1990) 29: 9515–9521.

Hite et al, Factors Affecting Fidelity of DNA Synthesis During PCR Amplification of D(C–A) D(G–T) Microsatellite Repeats, Nucleic Acids Research, vol. 24 No. 12:2429–2434 (1996).

http://www.lcresources.com/dlmain.htm (Jul. 9, 1998).

http://www.transgenomic.com/html/tmha.html (May 12, 1998).

Huber et al, High–Resolution Liquid Chromatography of Oligonucleotides on Noporus Alkylated Styrene–Divinylbenzene Copolymers, Analytical Biochemistry 212, 351–358 (1993).

Huber et al, High–Resolution Liguid Chromatography of DNA Fragments on Non–Porous Poly(Styrene–Divinylbenzene) Particles, Nucleic Acids Research, 1993, vol. 21, No. 5 1061–1066.

Huber et al, High–Performance Liquid Chromatographic Separation of Detritylated Oligonucleotides on Highly Cross–Linked Poly–(Styrene–Divinylbenzene) Particles, Journal of Chromatography, 599 (1992) 113–118.

Huber et al, Detection of Partial Denaturation in At–Rich DNA Fragments BYION–Pair Reversed–Phase Chromatography, Analytical Chemistry, 68: 2959–2965 (1996).

Huber et al, Rapid Analysis of Biopolymers on Modified Non–Porous Polystyrene–Divinylbenzene Particles, Chromatographia, vol. 37, No. 11/12: 653–658 (Dec. 1993).

Huber et al, Rapid and Accurate Sizing of DNA Fragments by Ion–Pair Chromatography on Alkylated Nonporous Poly-(Styrene–Divinylbenzene) Particles, Analytical Chemistry, 67: 578–585 (1995).

Huber et al., Micropellicluar Stationary Phases for High–Performance Liquid Chromatography of Double–Stranded DNA, J. of Chromatography A (1997) 000:000–000.

Innis et al. Optimiation of PCRs, PCR Protocols: A Guide in Methods and Applications, pp. 3–12 (1990).

Ip et al. Separation O Nucleosides and Nucleotides by Reversed–Phase HPLC with Volatile Buffers Allowing Sample Recovery, Analytical Biochemistry, 147, 180–185, (1985).

Issaq et al. Enthalpy and Entropy Effects for Hologous Solutes in HPLC with Alkul Chain Bonded Phasese, J. of Liquid Chromatography (1989) 12(11): 2067–2082.

J. Williams et al. Understanding Temperature Dynamics in PCR Reaction Tubes, Perkin Elmer PCR Technical Information pp. 78–81.

Jackson et al, Recognition of DNA Base Mismatches by a Phodium Intercalator, J. Am. Chem. Soc., vol. 119 No. 32: 12986–12987 (1997).

Jones et al, Optimal Temperature Selection for Mutation Detection by Denaturing HPLC and Comparison to Single–Stranded Conformation Polymorphism and Heteroduplex Analysis, Clinical Chemistry 45:8 1133–1140 (1999).

Keohavong et al, Fidelity of DNA Polymerases in DNA Amplification, Proc. Natl. Acad. Sci. USA, 86: 9253–9255 (1989).

Kuklin et al, Detection of Single–Nucleotide Polymorphisms with the Wave(TM) DNA Fragment Analysis Sytem, Genetic Testing, vol. 1 No. 3: 201–206 (1997).

Kwiatkowski et al. Use of RP Ion Pair Chromatography to Fractionate and Purify DNA Fragments and Monomeric Components of RNA, Acta Chemica scandinavica B. 38, 9, 721–733, (1984).

Kowk et al, Procedures to Minimize PCR Product Carry–Over Perkin Elmer Corporation, PCR Technical Information pp. 81–82.

Kuklin et al., New Paradigms in DNA Polymorphism Detection, Biomedical Products (1998) 7: 90–92.

Lerman et al, Computation Simulation of DNA Melting and Its Application to Denaturing Gradient Gel Electrophoreis, Methods in Enzymology, vol. 155: 482–501 (1987).

Lester et al, Rapid Quantification of Gene Expression by Competitive PT–PCR and Ion–Pair Reversed–Phase HPLC, Biotechniques, 20: 250–257 (1996).

Li et al, Strategies for Faster Gradient Chromatography, LC–GC, vol. 16 No. 5 (May 1998).

Lim, Sharon, DNA Denaturation Using the Cary 1/3 Thermal Analysis System, Varian Cor. Technical Note, Jun. 1991.

Lin–Goerke et al, PCR–Based Random Mutagenesis Using Manganese and Reduced DNTP Concentration, BioTechniques, vol. 23 No. 3:409–412 (1997).

Lisby, Gorm, Application of Nucleic Acid Amplification in Clinical Microbiology, Methods im Molecular Biology, vol. 92: PCR in Bioanalysis (1998).

Liu et al, Denaturing High Performance Liquid Chromatography (DHPLC) Used in the Detection of Germline and Somatic Mutations, Nucleic Acids Research. 1998, vol. 26, No. 6 1396–1400.

Mansukhani et al, Convenient, Nonradioactive, Heteroduplex–Based Methods for Identifying Recurrent Mutations in the BRCA1 and BRCA2 Genes, Diagnostic Molecular Pathology 6(4): 229–237, 1997.

Mark Meuth, The Molecular Basis of Mutations Induced by Deozyribonucleoside Triphosphate Pool Imbalances in Mammalian Cells, Experimental Cell Research, 181: 305–316 (1989).

Marlow et al, A Method for the Detection and Quantitation of PCR Template in Environmental Samples by High Performance Liquid Chromatography, Journal of Microbiological Methods 28 (1997) 45–53.

Melander et al., Mobile Phase Effects in Reversed–Phase Chromatography, J. of Chromatography (1979) 185: 99–109.

Moriyama et al. New RP HPLC Column for Oligonucleotide Separtion, Journal of Chromatography, 445, 225–233, (1988).

Mueller et al, Facile Oligomer Concentration and Tm Determination for Estimation of PCR Annealing Temperature Perkin Elmer Corporation, PCR Technical Information.

Myers et al, Detection of Single Base Changes in DNA: Ribonuclease Cleavage and Denaturing Gradient Gel Electrophoresis, Genomic Analysis: A Practical Approach, PRL Press, K. Davies, ed. (1988).

Myers et al, Nearly All Singel Base Substitutions in DNA Fragments Joined to a GC–Clamp can be Detected by Denaturing Graident Gel Elecrophoresis, Nucleic Acids Research, vol. 13 No. 9: 3131–3145 (1985).

Myers et al, Modification of the Melting Properties of Duplex DNA by Attachment of a GC–Rich DNA Sequence as Determined by Denaturing Gradient Gel Electrophoresis, Nucleic Acids Research vol. 13 No. 9 (1985) 3111–3129.

Nahum et al. Surface Silnols in Silica–Bonded Huydrocarbonaceous Stationary Phases, J. of Chromatography (1981) 203: 53–63.

Nollau et al, Methods for Detection of Point Mutations: Performance and Quality Assessment, Clinical Chemistry 43:7 1114–1128 (1997).

Oefner et al, High–Performance Liquid Chromatography for Routing Analysis of Hepatitis C Virus CDNA/PCR Products, Research Reports, vol. 16 No. 5 (1994).

Oefner et al.Poster Symposium—Session 29 Comparative DNA Sequencing by Denaturing High–Performance Liquid Chromatography (DHLPC), Am. J. Human Genet. Oct. 1995, 57:A66.

Oefner et al, High–Resoution Liquid Chromatography of Fluorescent Dye–Labeled Nucleic Acids, Analytical Biochemistry 223, 001–008 (1994).

Oefner et al, High–Resolution Liquid Chromatography of Nucleic Acids, American Laboratory (1994) 28C–28J.

Oefner et al, Allelic Discrimination by Denaturing High–Performance Liquid Chromatography, Journal of Chromatographyb, 1 (2000) 739 (2) 345–355.

Oefner et al, DNA Mutation Detection Using Denaturing High–Performance Liquid Chromatography, (DHPLC) Human Genetics 7.10.1–7.10.12.

Oleykowski et al, Mutation Detection Using a Novel Plant Endonuclease, Nucleic Acids Research, vol. 26 No. 20: 4597–4602 (1998).

Pager, A Liquid Chromatpgraphic Prepartion of Retroviral RNA, Anal. Biochem. (1993) 215: 231–235.

Petro et al, Molded Monolithid Rod of Macrophrous Poly-(Styrene–Co–Divinylbenzene) as a Separation Medium for PHLC of Synthtic Polymers . . . , Analytical Chemistry 68: 315–321 (1996).

Poland et al, Recursion Relation Generation of Probability Profiles for Specific–Sequence Macromolecules with Long–Range Correlations, Biopolymers, 13: 1859–1871 (1974).

Poole et al. Chromatography Today (1991) Elsevier, New York, pp. 313–342.

Rao et al, Direct Sequencing of Polymerase Chain Reaction–Amplified DNA, Analytical Biochemistry, 216: 1–14 (1994).

Ruano et al. PCR: The First Few Cycles, Amplifications, Issue 7: 1–4 (Oct. 1991).

Sardelli et al. PCR Optimization—Reaction Conditions and Components, Perkin Elmer Corporation, PCR Technical Information.

Schoburg et al. Immobilization of Stationary Liquids in Reversed– and Normal–Phase Liquid Chromatography, J. of Chromatography (1983) 282: 27–39.

Schoburg et al. Immobilization of Stationary Liquids of Silica Particles by Y–Radiation, Chromatographia (1984) 18: 265–274, No. 5.

Snyder et al. Gradient Elution in Reversed–Phase HPLC, Anal. Chem. (1983) 55: 1412A–1430A, No. 14.

Tashlitskii et al. Optimization of Conditions for Ion–Pair HPLC of Oligonucleotides Bioorg. Khim., 23 (9), 732–741 (1997) Biosis Abstract No. 01070821.

Taylor, Graham R., Laboratory Methods for the Detection of Mutations and Polymorphisms in DNA, Ch. 9, 18–22, CRC Press, Boca Raton, New York (1997).

Transgenomic, Inc. Technical Note General Description: DNASep.

Underhill et al, A Pre–Columbian Y Chrromosome–Specific Transition and Its Implications for Human Evolutionary History, Proc. Natl. Acad. Sci., 93: 196–200 (Jan. 1996).

Underhill et al, Detection of Numerous Y Chromosome Biallelic Polymorphisms by Denaturing High–Performance Liquid Chromatography, Genome Research, No. 7: 996–1005 (1997).

Vtorushna et al. Study of Diastereomers of Non–Ionin Oligonucleotide Analogues. VI. Separation of Diastereomers of Ethyl Phosphotriesters O Octanucleotide d(GC-CAAACA) by Means of HP Complementary Chromatography, Bioorg. Khim. 18, 1, 92–99 (1992).

Wang et al, Reversed–Phase Chromatography of SMLL Molecules and Peptides ONA Continous Rod of Macrophorous Poly(Styrene–Codivinylbenzene), Journal of Chromatography, No. 669: 230–235 (1994).

Zon et al. Purification of Synthetic Oligodeoxyribonucleotides, Chapter 14 in High Performance Liquid Chromatography in Biotechnology, Hancock (ed.) John Wiley & Sons, New York, NY, 1990, pp. 301–398.

Breslauer et al, Predicting DNA Duplex Stability From the Base Sequence, Proc. Natl. Acad. Sci., 83: 3746–3750 (Jun. 1986).

Huber et al, Analysis of Nucleic Acids by Capillary Ion–Pair Reversed–Phase HPLC Coupled to Negative–Ion Electrospray Ionization Mass Spectrometry, Anal. Chem. 71: 3730–3739, (1999).

Khrapko et al, Identification of Point Mutations in Mixtures by Capillary Electrophoresis Hybridization, Nucleic Acids Research, 26: 5738–5740 (1998).

Schmitter et al. Rapid Purification of DNA Fragments by High–Performance Size–Exclusion Chromatography, J of Chrom.378: 462–466, (1986).

Slater et al, PFU DNA Polymerase: A High Fidelity Enzyme For Nucleic Acid Amplification, Promega Notes 68: 7–10.

Sofer et al, Process Chromatography, A Guide To Validation, Academic Press, 5–20 (1991).

Wages et al. High–Performance Chromatography Analysis of PCR Products, PCR Strategies, Academic Press, 140–153, (1995).

Wong et al, General Method for HPLC Purification and Sequencing of Selected dsDNA Gene Fragments from Complex PCRs Generated Durign Gene Expression Profiling, BioTechniques 28: 776–783, (Apr. 2000).

Xiao et al, Human Mutation, 17:439–474 (2001).

* cited by examiner

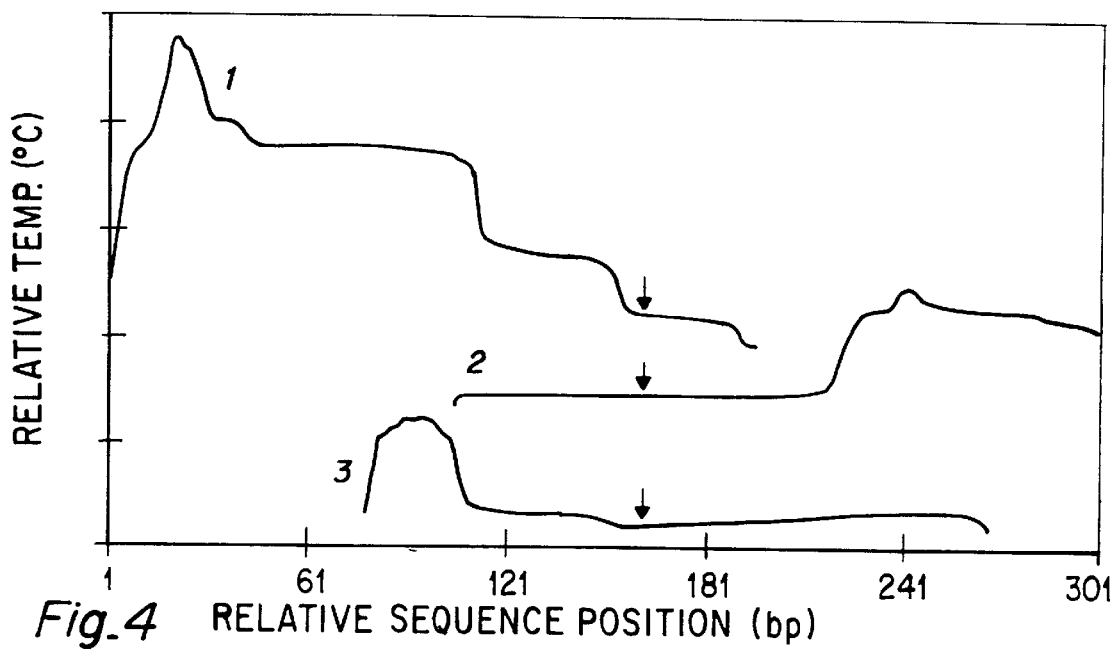
Fig. 4 RELATIVE SEQUENCE POSITION (bp)
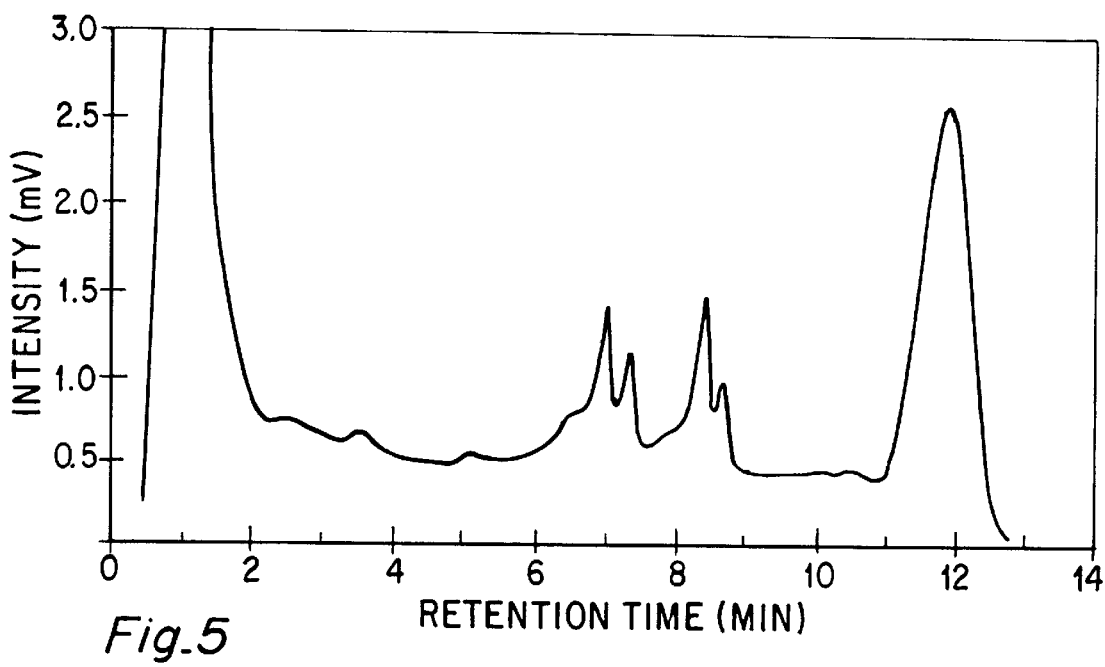
Fig. 5 RETENTION TIME (MIN)

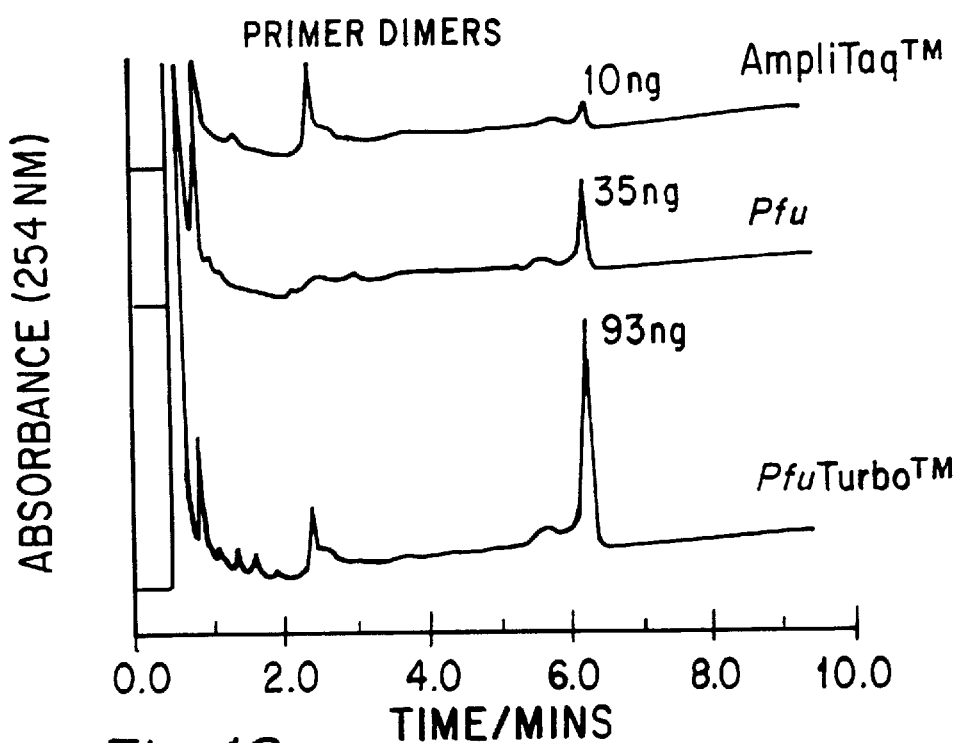
Fig_19
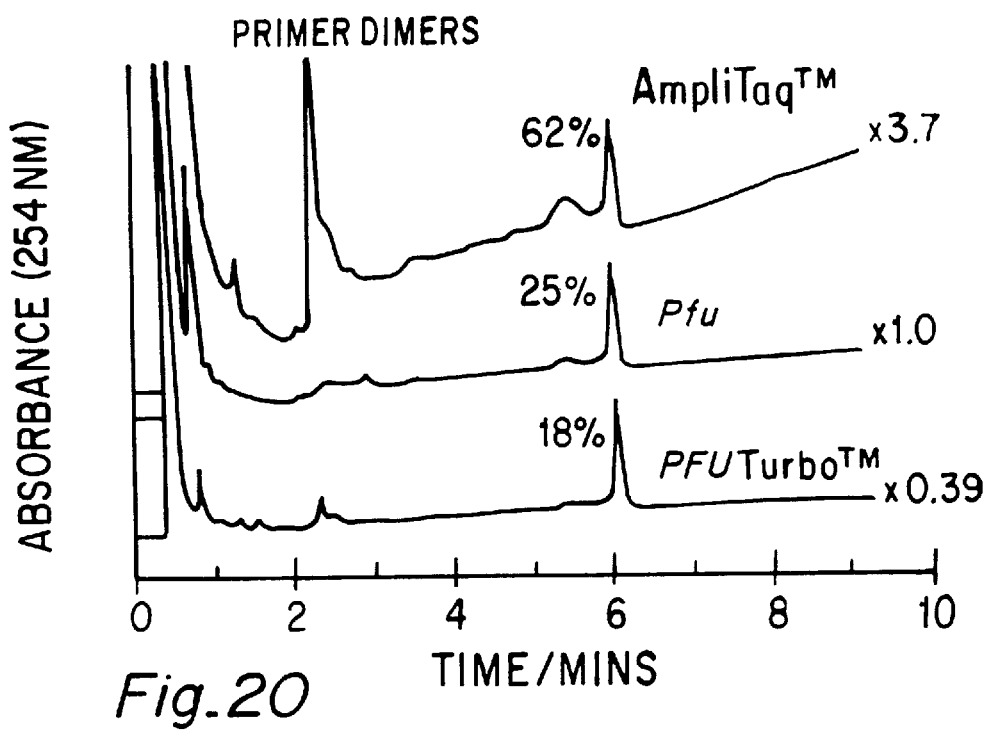
Fig_20

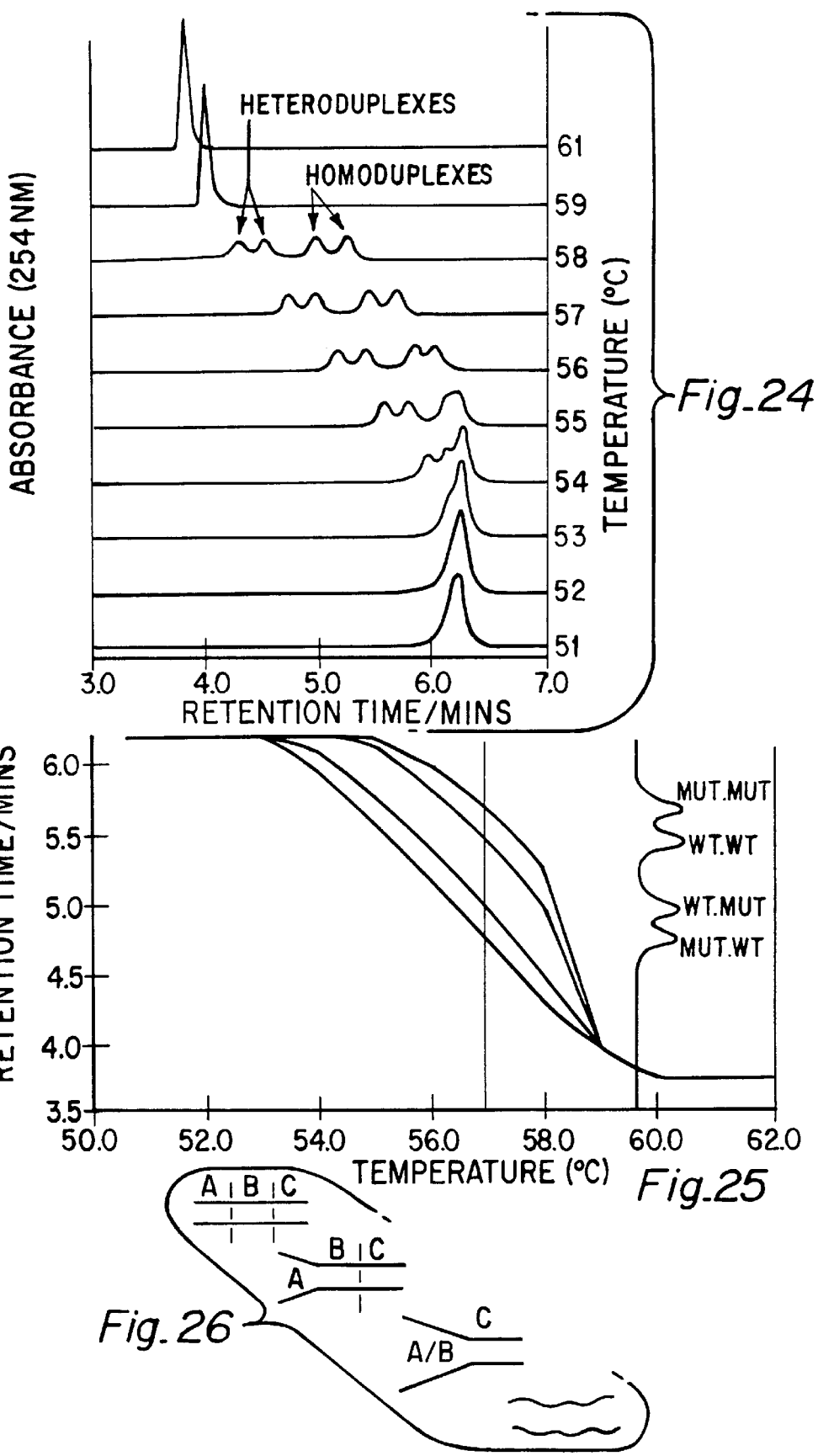

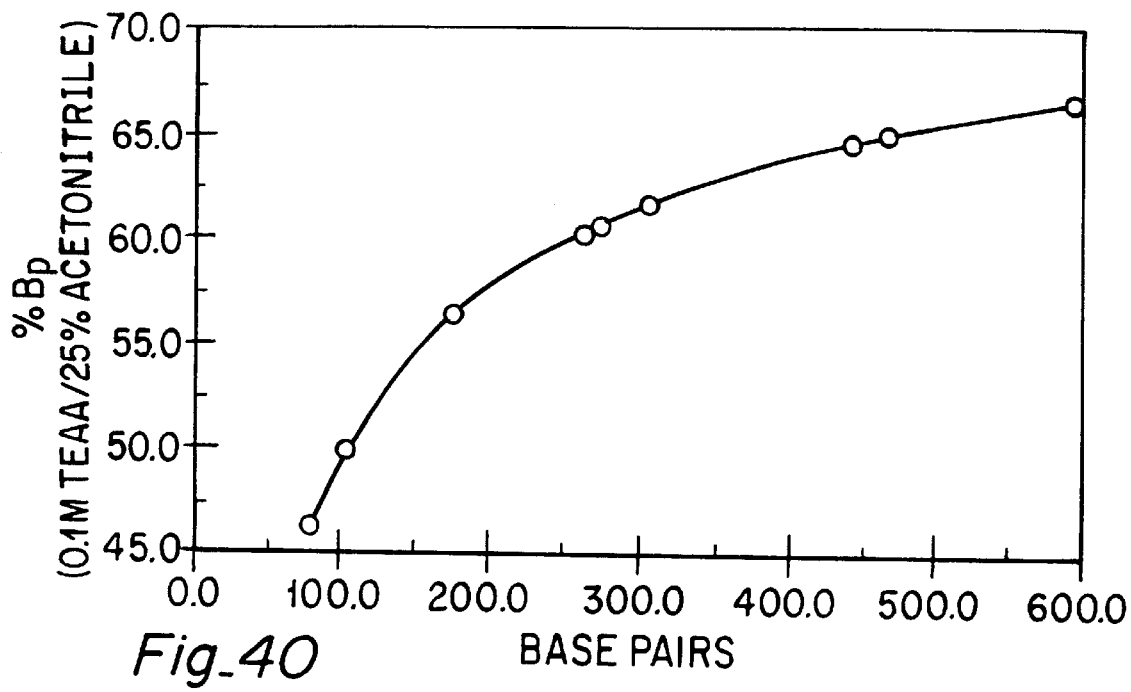
Fig_40
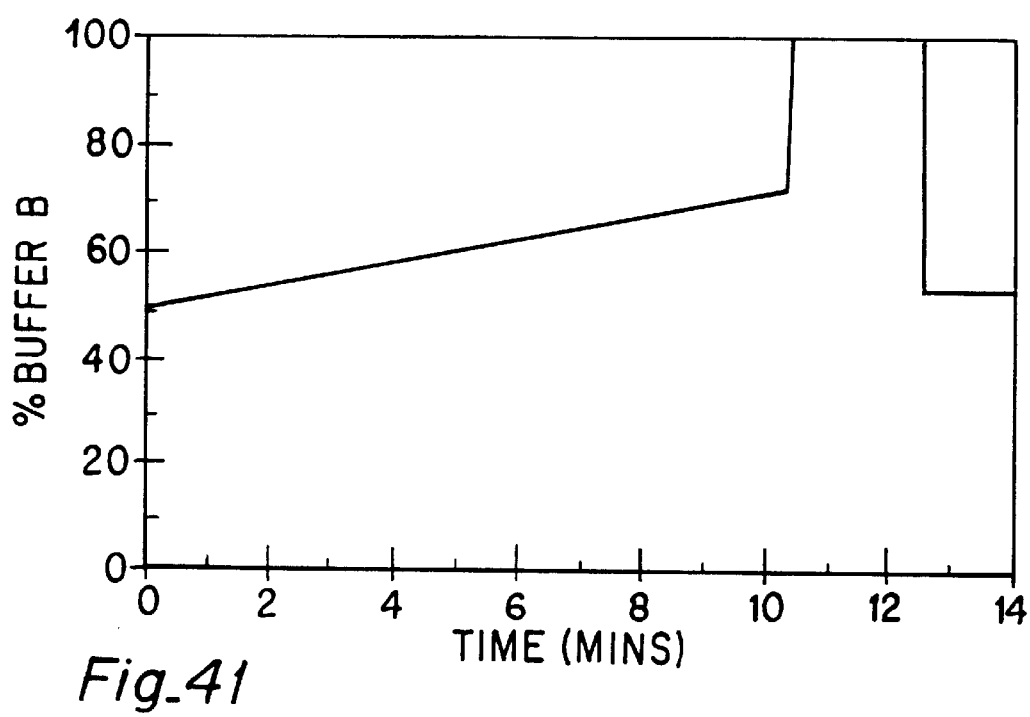
Fig_41

METHOD OF CONCENTRATING POLYNUCLEOTIDES USING MIPC

CROSS REFERENCE TO RELATED CO-PENDING APPLICATIONS

This application is a continuation of U.S. patent application Ser. No. 09/129,105, filed Aug. 4, 1998, now U.S. Pat. No. 6,287,822. This application is a regular U.S. patent application under 35 U.S.C. §111(a).

FIELD OF THE INVENTION

The present invention concerns an improved method for detection of mutations in nucleic acids.

BACKGROUND OF THE INVENTION

The ability to detect mutations in double stranded polynucleotides, and especially in DNA fragments, is of great importance in medicine, as well as in the physical and social sciences. The Human Genome Project is providing an enormous amount of genetic information which is setting new criteria for evaluating the links between mutations and human disorders (Guyer et al., *Proc. Natl. Acad. Sci. USA* 92:10841 (1995)). The ultimate source of disease, for example, is described by genetic code that differs from wild type (Cotton, TIG 13:43 (1997)). Understanding the genetic basis of disease can be the starting point for a cure. Similarly, determination of differences in genetic code can provide powerful and perhaps definitive insights into the study of evolution and populations (Cooper, et. al., *Human Genetics* vol. 69:201 (1985)). Understanding these and other issues related to genetic coding is based on the ability to identify anomalies, i.e., mutations, in a DNA fragment relative to the wild type. A need exists, therefore, for a methodology to detect mutations in an accurate, reproducible and reliable manner.

DNA molecules are polymers comprising sub-units called deoxynucleotides. The four deoxynucleotides found in DNA comprise a common cyclic sugar, deoxyribose, which is covalently bonded to any of the four bases, adenine (a purine), guanine(a purine), cytosine (a pyrimidine), and thymine (a pyrimidine), hereinbelow referred to as A, G, C, and T respectively. A phosphate group links a 3'-hydroxyl of one deoxynucleotide with the 5'-hydroxyl of another deoxynucleotide to form a polymeric chain. In double stranded DNA, two strands are held together in a helical structure by hydrogen bonds between, what are called, complementary bases. The complementarity of bases is determined by their chemical structures. In double stranded DNA, each A pairs with a T and each G pairs with a C, i.e., a purine pairs with a pyrimidine. Ideally, DNA is replicated in exact copies by DNA polymerases during cell division in the human body or in other living organisms. DNA strands can also be replicated in vitro by means of the Polymerase Chain Reaction (PCR).

Sometimes, exact replication fails and an incorrect base pairing occurs, which after further replication of the new strand results in double stranded DNA offspring containing a heritable difference in the base sequence from that of the parent. Such heritable changes in base pair sequence are called mutations.

In the present invention, double stranded DNA is referred to as a duplex. When the base sequence of one strand is entirely complementary to base sequence of the other strand, the duplex is called a homoduplex. When a duplex contains at least one base pair which is not complementary, the duplex is called a heteroduplex. A heteroduplex duplex is formed during DNA replication when an error is made by a DNA polymerase enzyme and a non-complementary base is added to a polynucleotide chain being replicated. Further replications of a heteroduplex will, ideally, produce homoduplexes which are heterozygous, i.e., these homoduplexes will have an altered sequence compared to the original parent DNA strand. When the parent DNA has the sequence which predominates in a natural population it is generally called the "Wild type."

Many different types of DNA mutations are known. Examples of DNA mutations include, but are not limited to, "point mutation" or "single base pair mutations" wherein an incorrect base pairing occurs. The most common point mutations comprise "transitions" wherein one purine or pyrimidine base is replaced for another and "transversions" wherein a purine is substituted for a pyrimidine (and visa versa). Point mutations also comprise mutations wherein a base is added or deleted from a DNA chain. Such "insertions" or "deletions" are also known as "frameshift mutations". Although they occur with less frequency than point mutations, larger mutations affecting multiple base pairs can also occur and may be important. A more detailed discussion of mutations can be found in U.S. Pat. No. 5,459,039 to Modrich (1995), and U.S. Pat. No. 5,698,400 to Cotton (1997). These references and the references contained therein are incorporated in their entireties herein.

The sequence of base pairs in DNA codes for the production of proteins. In particular, a DNA sequence in the exon portion of a DNA chain codes for a corresponding amino acid sequence in a protein. Therefore, a mutation in a DNA sequence may result in an alteration in the amino acid sequence of a protein. Such an alteration in the amino acid sequence may be completely benign or may inactivate a protein or alter its function to be life threatening or fatal. On the other hand, mutations in an intron portion of a DNA chain would not be expected to have a biological effect since an intron section does not contain code for protein production. Nevertheless, mutation detection in an intron section may be important, for example, in a forensic investigation.

Detection of mutations is, therefore, of great interest and importance in diagnosing diseases, understanding the origins of disease and the development of potential treatments. Detection of mutations and identification of similarities or differences in DNA samples is also of critical importance in increasing the world food supply by developing diseases resistant and/or higher yielding crop strains, in forensic science, in the study of evolution and populations, and in scientific research in general (Guyer et al., *Proc. Natl. Acad. Sci. USA* 92:10841 (1995); Cotton, TIG 13:43 (1997)). These references and the references contained therein are incorporated in their entireties herein.

Alterations in a DNA sequence which are benign or have no negative consequences are sometimes called "polymorphisms". In the present invention, any alterations in the DNA sequence, whether they have negative consequences or not, are called "mutations". It is to be understood that the method of this invention has the capability to detect mutations regardless of biological effect or lack thereof. For the sake of simplicity, the term "mutation" will be used throughout to mean an alteration in the base sequence of a DNA strand compared to a reference strand. It is to be understood that in the context of this invention, the term "mutation" includes the term "polymorphism" or any other similar or equivalent term of art.

There exists a need for an accurate and reproducible analytical method for mutation detection which is easy to implement. Such a method, which can be automated and provide high throughput sample screening with a minimum of operator attention, is also highly desirable.

Analysis of DNA samples has historically been done using gel electrophoresis. Capillary electrophoresis has been used to separate and analyze mixtures of DNA. However, these methods cannot distinguish point mutations from homoduplexes having the sa me base pair length.

The "heteroduplex site separation temperature" is defined herein to mean, the temperature at which one or more base pairs denature, i.e., separate, at the site of base pair mismatch in a heteroduplex DNA fragment. Since at least one base pair in a heteroduplex is not complementary, it takes less energy to separate the bases at that site compared to its fully complementary base pair analog in a homoduplex. This results in the lower melting temperature of a heteroduplex compared to a homoduplex. The local denaturation creates, what is generally called, a "bubble" at the site of base pair mismatch. The bubble distorts the structure of a DNA fragment compared to a fully complementary homoduplex of the same base pair length. This structural distortion under partially denaturing conditions has been used in the past to separate heteroduplexes and homoduplexes by denaturing gel electrophoresis and denaturing capillary electrophoresis. However, these techniques are operationally difficult to implement and require highly skilled personnel. In addition, the analyses are lengthy and require a great deal of set up time. A denaturing capillary gel electrophoresis analysis of a 90 base pair fragment takes more than 30 minutes and a denaturing gel electrophoresis analysis may take 5 hours or more. The long analysis time of the gel methodology is further exacerbated by the fact that the movement of DNA fragments in a gel is inversely proportional to the length of the fragments.

In addition to the deficiencies of denaturing gel methods mentioned above, these techniques are not always reproducible or accurate since the preparation of a gel and running an analysis is highly variable from one operator to another.

Recently, a chromatographic method called Matched Ion Polynucleotide Chromatography (MIPC) was introduced to effectively separate mixtures of double stranded polynucleotides, in general and DNA, in particular, wherein the separations are based on base pair length (U.S. Pat. No. 5,585,236 to Bonn (1996); Huber, et al., *Chromatographia* 37:653 (1993); Huber, et al., *Anal. Biochem.* 212:351 (1993)). These references and the references contained therein are incorporated herein in their entireties. MIPC is not limited by any of the deficiencies associated with gel based separation methods.

The term "Matched Ion Polynucleotide Chromatography" as used herein is defined as a process for separating single and double stranded polynucleotides using non-polar separation media, wherein the process uses a counter-ion agent, and an organic solvent to release the polynucleotides from the separation media. MIPC separations are complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and column inlet areas.

As the use and understanding of MIPC developed it became apparent that when MIPC analyses were carried out at a partially denaturing temperature, i.e., a temperature sufficient to denature a heteroduplex at the site of base pair mismatch, homoduplexes could be separated from heteroduplexes having the same base pair length (Hayward-Lester, et al., *Genome Research* 5:494 (1995); Underhill, et al., *Proc. Natl. Acad. Sci. USA* 93:193 (1996); Doris, et al., DHPLC Workshop, Stanford University, (1997)). These references and the references contained therein are incorporated herein in their entireties. Thus, the use of DHPLC was applied to mutation detection (Underhill, et al., *Genome Research* 7:996 (1997); Liu, et al., *Nucleic Acid Res.,* 26;1 396 (1998)).

DHPLC can separate heteroduplexes that differ by as little as one base pair. However, separations of homoduplexes and heteroduplexes can be poorly resolved. Artifacts and impurities can also interfere with the interpretation of DHPLC separation chromatograms in the sense that it may be difficult to distinguish between an artifact or impurity and a putative mutation (Underhill, et al., *Genome Res.* 7:996 (1997)). The presence of mutations may even be missed entirely (Liu, et al., *Nucleic Acid Res.* 26:1396 (1998)). The references cited above and the references contained therein are incorporated in their entireties herein.

The accuracy and reproducibility of mutation detection assays based on DHPLC have been compromised in the past for two principle reasons; DHPLC system related problems and PCR related problems.

When used under partially denaturing conditions, MIPC is defined herein as Denaturing Matched Ion Polynucleotide Chromatography (DMIPC).

Samples to be analyzed for the presence or absence of mutations often contain amounts of material too small to detect. The first step in mutation detection assays is, therefore, sample amplification using the PCR process. PCR amplification comprises steps such as primer design, choice of DNA polymerase enzyme, the number of amplification cycles and concentration of reagents. Each of these steps, as well as other steps involved in the PCR process affects the purity of the amplified product. Although the PCR process and the factors which affect fidelity of replication and product purity are well known in the PCR art, these factors have not been addressed, heretofore, in relation to mutation detection using MIPC. As a result, PCR induced mutations, wherein a non-complementary base is added to a template, are often formed during sample amplification. Such PCR induced mutations make mutation detection results ambiguous, since it may not be clear if a detected mutation was present in the sample or was produced during the PCR process. Unfortunately, many workers in the PCR and mutation detection fields make the erroneous assumption that PCR replication is perfect or close to perfect and PCR induced mutations are generally not taken into consideration in mutation detection analyses. This approach can result in false positives. Applicants have recognized the importance of optimizing PCR sample amplification in order to minimize the formation of PCR induced mutations and ensure an accurate and unambiguous analysis of putative mutation containing samples. The use of MIPC by Applicants to identify and optimize the factors affecting PCR replication fidelity will be discussed in the Detailed Description.

Other aspects of mutation detection by MIPC which have not been heretofore addressed, comprise the treatment of, and materials comprising chromatography system components, the treatment of, and materials comprising separation media, solvent pre-selection to minimize methods development time, optimum temperature pre-selection to effect partial denaturation of a heteroduplex during MIPC and optimization of MIPC for automated high throughput mutation detection screening assays. These factors are essential in order to achieve unambiguous, accurate and reproducible mutation detection results using MIPC.

A need exists to identify and optimize all the aspects of the MIPC methodology in order to minimize artifacts and remove ambiguity from the analysis of samples containing putative mutations.

SUMMARY OF THE INVENTION

Accordingly, one object of the present invention is to provide a method for detecting mutations in nucleic acids which is accurate, i.e., practically free of misleading results (e.g. "false positives"), is convenient to use, makes it possible to rapidly obtain results, is reliable in operation, is simple, convenient and inexpensive to operate.

Another object of the present invention is to provide a method for detecting mutations which utilizes a chromatographic method for separating polynucleotides with improved and predictable separation and efficiency.

An additional object of the present invention is to provide an improved method for preparing a sample of nucleic acids (e.g. DNA or RNA) prior to analysis for mutation.

Still another object of the instant invention is to provide a method for optimizing PCR for use in mutation detection.

Yet another object of the invention is to provide an improved method for selecting the temperature for conducting a chromatographic separation of nucleic acids for mutation detection.

An additional object of the invention is to provide an improved method for determining the optimal mobile phase for eluting nucleic acids in screening for mutations.

Still yet another object of the invention is to provide a method which can be automated.

A further object of the invention is to provide a method which can be used in basic research to test for unknown mutations and which can be used to rapidly screen numerous samples for a known mutation.

These and other objects which will become apparent from the following specification have been achieved by the present invention.

In one aspect, the present invention is an improved method for separating a sample mixture of polynucleotides by Matched Ion Polynucleotide Chromatography in which the concentration of polynucleotides (e.g., double stranded DNA) in the sample mixture is below a determined threshold concentration (e.g., the lower limit of detection of the polynucleotides). The improvement includes applying the sample to the column whereby the polynucleotides are accumulated on the column. In a preferred embodiment, the method includes applying the sample in a mobile phase having a concentration of organic solvent less than a concentration necessary to elute the polynucleotides in the mixture. The mobile phase preferably also includes a counterion agent. In a specific embodiment, the method further includes applying the mixture to a Matched Ion Polynucleotide Chromatography column and flowing an aqueous mobile phase under isocratic conditions through said column wherein impurities are removed from said mixture. If the sample mixture is applied to the column in an aliquot of greater than 10 $\mu L$, the solvent mixture preferably includes a counterion reagent.

In an important aspect, the present invention is a method for preparing a double stranded DNA fragment for mutation detection and is also a method for mutation detection of a double stranded DNA fragment in which each method uses Denaturing Matched Ion Polynucleotide Chromatography (DMIPC). DMIPC is MIPC but carried out at a temperature which causes denaturing at any mutation site (i.e., a base pair mismatch site) without denaturing another portion a sample sequence. For each of these methods, the double stranded DNA fragment corresponds to a wild type double stranded DNA fragment having a known nucleotide sequence. The steps of the methods include (a) analyzing the sequence of the wild type double stranded DNA fragment to segment the double stranded DNA fragment into sample sequences, e.g., constant melting domains, of nucleotides having a melting point range of less than about 15 degrees C., each sample sequence having a first end and a second end opposite thereto; (b) amplifying one of these sample sequences by PCR using a set of primers which flank the first and second ends of this sample sequences, and (c) analyzing the amplified sample by MIPC. The PCR amplification can include an analog of dGTP, e.g., 2,6-aminopurine, and can include a G-C clamp of up to 40 bases in a primer. In a preferred embodiment, the mixture of the amplified sample sequence and the corresponding wild type double stranded DNA segment are subjected to a hybridization process in which the mixture is heated to a temperature at which the strands are completely denatured and then cooled until the strands are completely annealed, whereby a mixture comprising two homoduplexes and two heteroduplexes is formed if the sample sequence includes a mutation.

In another embodiment for preparing a double stranded DNA fragment for mutation detection by Denaturing Matched Ion Polynucleotide Chromatography wherein the double stranded DNA fragment corresponds to a wild type double stranded DNA fragment having a known nucleotide sequence, the method steps include analyzing the sequence of the wild type double stranded DNA fragment to segment the double stranded DNA fragment into sample sequences of nucleotides having a high melting domain and a low melting domain in which a mutation site is located; and amplifying one of said sample sequences by PCR using a set of primers which flank the first and second ends of said sample sequences.

In a still further embodiment for preparing a double stranded DNA fragment for mutation detection by Denaturing Matched Ion Polynucleotide Chromatography, wherein the double stranded DNA fragment corresponds to a wild type double stranded DNA fragment having a known nucleotide sequence, the method comprises the steps of analyzing the sequence of the wild type double stranded DNA fragment to segment the double stranded DNA fragment into sample sequences of nucleotides wherein the mutation site is within twenty-five percent of the total number of base pairs from an end of the fragment; and amplifying one of said sample sequences by PCR using a set of primers which flank the first and second ends of said sample sequences.

In another aspect, the invention provides a method for evaluating a PCR process to determine if it induces mutations. The method includes the steps of (a) amplifying a polynucleotide by performing a plurality of PCR process cycles to yield a PCR amplification product, (b) analyzing the PCR amplification product preferably by MIPC to yield a PCR amplification product profile, including a profile of any mutations produced by PCR produced mutation. An example of such a profile is the elution profile obtained from the Denaturing Matched Ion Polynucleotide Chromatography process. In a preferred embodiment, the product profile is compared against a reference profile to determine the presence of PCR induced mutations in the PCR amplification product. In a related aspect, the invention is a method for identifying deviations of a PCR process from a predetermined reference profile. The method steps include amplifying a polynucleotide by performing a plurality of PCR process cycles to yield a PCR amplification product and analyzing the PCR amplification product by MIPC to yield a PCR amplification product profile, including a profile of any PCR-induced mutations. The PCR amplification product profile can be compared against a reference profile to identify the deviations of the PCR reaction product, including PCR-induced mutations, from a predetermined reference profile. In a preferred embodiment, PCR induced mutations are detected by hybridizing the reaction after the last cycle and analyzing the reaction by MIPC.

In an important aspect, the invention is a method for reducing PCR-induced mutations which includes (a) amplifying a polynucleotide by performing a plurality of PCR amplification process cycles to yield a first PCR amplification product (b) analyzing the first PCR amplification product by MIPC to yield a PCR amplification product profile (c) comparing the PCR amplification product profile against a reference profile to determine the presence of PCR induced mutations, and (d) amplifying a polynucleotide by performing a plurality of PCR amplification process cycles with an adjustment of one or more process variables to form a second PCR amplification product with reduced PCR induced mutations.

The method can include the additional steps of analyzing the PCR reaction product obtained in step (d) by MIPC to yield a second reaction product profile followed by (f) comparing the second reaction product profile against a set of standard profiles to determine deviations of the PCR process from a predetermined standard; and (g) performing a plurality of PCR process cycles with an adjustment of one or more process variables to form a third PCR reaction product with reduced deviation of the PCR process from the predetermined standard. Examples of the process variables include magnesium concentration, dNTP concentrations, enzyme concentration, temperature, and source of DNA polymerase. For example, a non-proof reading DNA polymerase can be replaced by a proof reading polymerase. The analysis of the PCR products can be used to evaluate primers and re-design primers to minimize artifacts, such as primer dimer formation.

The evaluation of the PCR process by MIPC can also be used to increase product yield and minimize byproducts. A PCR product profile is compared to a predetermined standard profile. The PCR is repeated with an increase of one or more of, the nucleotide, magnesium ion, or enzyme concentrations, or a decrease in the temperature or a combination thereof. Additional improvements in the PCR can be made by reducing the number of PCR process cycles when an excessive level of by products is observed.

Deviations from a predetermined standard profile can be further reduced by analyzing a second product profile, obtained using MIPC, of a PCR reaction after a reaction variable has been adjusted. This second profile is compared to a set of standard profiles to determine deviations of the PCR process form the predetermined standard. Another set of PCR cycles is then performed with a adjustment of one or more process variables to afford a third PCR reaction product profile with reduced deviation in the PCR products form the predetermined standard.

In another preferred embodiment of this aspect of the invention, the PCR product can be separated from reaction impurities and collected during MIPC analysis of the reaction. In this manner, the purified PCR product can be amplified in another series of PCR cycles. The purified PCR product can also be amplified by cloning in a host system.

In yet another important aspect, the invention provides a method for determining the heteromutant site separation temperature. The method comprises the steps of (a) heating a mixture of a sample double stranded DNA segment and a corresponding wild type double stranded DNA segment to a temperature at which the strands are completely denatured; (b) cooling the product of step (a) until the strands are completely annealed, whereby a mixture comprising two homoduplexes and two heteroduplexes is formed if the sample segment includes a mutation; (c) determining the heteromutant site separation temperature; (d) analyzing the product of step (b) with MIPC at the heteromutant site separation temperature to identify the presence of any heteromutant site separated components therein. In one embodiment, if the sequence of the normal double stranded DNA is known, the heteromutant site separation temperature is determined by the equation: $T(hsst)=X+m \cdot T(w)$, wherein $T(hsst)$ is the heteromutant site separation temperature, $T(w)$ is the temperature, calculated by software or determined experimentally, at which there is a selected equilibrium between denatured and non-denatured states (e.g., a ratio of 50/50 or 25/75 denatured to non-denatured) of the normal double stranded DNA, m is a weighting factor, and X is the DMIPC detection factor. In a related embodiment, the heteromutant site separation, temperature, referred to above, is determined by analyzing the product of step (b) by MIPC in a series of incremental MIPC separations in the mutation separation temperature range, each successive separation having a higher temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample. Similarly, the heteromutant site separation temperature can be determined by performing a series of incremental MIPC separations in the mutation separation temperature range, each successive separation having a lower temperature than the preceding separation until a mutation separation profile is observed or the absence of any mutation separation profile in the mutation separation temperature range is observed, wherein a mutation separation profile identifies the presence of a mutation and the absence of a mutation separation profile indicates an absence of mutation in the sample. In a preferred embodiment, determination of a T(hsst) by MIPC is computer controlled and automated, whether the series of MIPC separations is performed at incrementally higher or incrementally lower temperatures.

A further aspect of the invention provides a preferred method for detecting DNA genetic mutations comprising the steps of (a) a calculation step for obtaining a calculated heteromutant site separation temperature; (b) a prediction step for obtaining a predicted heteromutant site separation temperature; (c) heating a mixture of a sample double stranded DNA segment and a corresponding wild type double stranded DNA segment to the predicted heteromutant site separation temperature; (d) analyzing the product of step (c) with MIPC at the predicted heteromutant site separation temperature to identify the presence of any heteromutant site separated components therein. In a preferred embodiment, the calculation step comprises calculating the calculated heteromutant site separation temperature according to a first mathematical model. Also in a preferred embodiment, the prediction step comprises adjusting the calculated heteromutant site separation temperature according to a second mathematical model. The second mathematical model can be based on a comparison of empirically determined heteromutant site separation temperatures with calculated heteromutant site separation temperatures. The calculated heteromutant site separation temperatures can be calculated using the first mathematical model. In a preferred embodiment, determination of a T(hsst) by MIPC is computer controlled and automated.

In another important aspect of the invention, a chromatographic method is provided for separating a mixture of heteroduplex and homoduplex DNA molecules, including a first eluting DNA molecule and a last eluting DNA molecule, under conditions which selectively denature a mutation site present in the heteroduplex DNA molecule, comprising the steps of: (a) applying the mixture to a Matched Ion Polynucleotide Chromatographic column, (b) eluting the molecules of the mixture using a mobile phase comprising a counterion agent and a pre-selected fragment bracketing range of organic solvent concentration, the range comprising an initial concentration and a final concentration of organic solvent, the initial concentration containing an organic solvent concentration up to an amount required to elute the first eluting DNA molecule in the mixture, and the final concentration containing an organic solvent concentration sufficient to elute the last eluting DNA molecule in the mixture.

In a preferred embodiment, the pre-selected fragment bracketing range is obtained from a reference relating organic solvent concentration required for eluting DNA molecules of different base pair length, and base pair length. In a particular embodiment, a preliminary organic solvent concentration, capable of eluting a DNA molecule of a specific base pair length, is obtained from a reference relating organic solvent concentration required for eluting DNA molecules of different base pair length, and base pair length, and the preliminary solvent concentration is used to select a fragment bracketing range. The heteroduplex molecules and the homoduplex molecules can have the same base pair length. The heteroduplex molecules can consist of at least two different heteroduplexes and the homoduplex molecules can be at least two different homoduplexes. These molecules are detected (e.g., by UV absorbance) after being eluted from the column. The organic solvent used in this aspect of the invention is selected from the group consisting of methanol, ethanol, acetonitrile, ethyl acetate, and 2-propanol. The preferred organic solvent is acetonitrile. The counterion agent in this aspect of the invention is selected from the group consisting of lower alkyl primary, secondary, and tertiary amines, lower trialkylammonium salts and lower quaternary ammonium salts. Examples of a counterion agent include octylammonium acetate, decylammonium acetate, octadecylammonium acetate, pyridiniumammonium acetate, cyclohexylammonium acetate, diethylammonium acetate, propylethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, carbonate, phosphate, sulfate, nitrate, propionate, formate, chloride, bromide, and mixtures of any one or more of the above. However, the most preferred counterion agent is triethylammonium acetate.

A related aspect, involves, before step (a) immediately above, the preliminary steps of: (a) deriving a relationship between organic solvent concentration in the mobile phase required for eluting DNA molecules of different base pair length from the column, as a function of base pair length, and (b) determining from this derived relationship a preselected fragment bracketing range of organic solvent and a preliminary organic solvent concentration.

A critical aspect of the invention is a method for treating a matched ion polynucleotide chromatography column in order to improve the resolution of double stranded DNA fragments separated on the column comprising flowing a solution containing a multivalent cation binding agent through the column, wherein said solution has a temperature of about 50° C. to 90° C. The preferred temperature is about 70° C. to 80° C. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide, α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α,α',α"-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyldlthiocarbarbamate, and zinc dibenzyldithiocarbamate. However, the most preferred chelating agent is EDTA. In this aspect of the invention, the solution preferably includes an organic solvent as exemplified by alcohols, nitriles, dimethylformamide, tetrahydrofuran, esters, and ethers. The most preferred organic solvent is acetonitrile. In one embodiment, the solution can include a counterion agent such as lower primary, secondary and tertiary amines, and lower trialkyammonium salts, or quaternary ammonium salts. More specifically, the counterion agent can be octylammonium acetate, decylammonium acetate, octadecylammonium acetate, pyridiniumammonium acetate, cyclohexylammonium acetate, diethylammonium acetate, propylethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, carbonate, phosphate, sulfate, nitrate, propionate, formate, chloride, bromide, and mixtures of any one or more of the above. However, the most preferred counterion agent is triethylammonium acetate.

In yet a further aspect, the invention provides a method for storing a Matched Ion Polynucleotide Chromatography column in order to improve the resolution of double stranded DNA fragments separated on the column. The preferred method includes flowing a solution containing a multivalent cation binding agent through the column prior to storing the column. In a preferred embodiment, the multivalent cation binding agent is a coordination compound, examples of which include water-soluble chelating agents and crown ethers. Specific examples include acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide. α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α,α', α"-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyldlthiocarbarbamate, and zinc dibenzyldithiocarbamate. However, the most preferred chelating agent is EDTA. In this aspect of the invention, the solution preferably includes an organic solvent as exemplified by alcohols, nitriles, dimethylformamide, tetrahydrofuran, esters, and ethers. The most preferred organic solvent is acetonitrile. In one embodiment, the solution can also include a counterion agent such as lower primary, secondary and tertiary amines, and lower trialkyammonium salts, or quaternary ammonium salts. More specifically, the counterion agent can be octylammonium acetate, decylammonium acetate, octadecylammonium acetate, pyridiniumammonium acetate, cyclohexylammonium acetate, diethylammonium acetate, propylethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, tetrabutylammonium acetate, carbonate, phosphate, sulfate, nitrate, propionate, formate, chloride, bromide, or mixtures of any one or more of the above. However, the most preferred counterion agent is triethylammonium acetate.

BRIEF DESCRIPTION OF THE DRAWINGS

FIG. 4 shows the melting map of three DNA fragments with a mutation site indicated by an arrow.

FIG. 5 shows the DMIPC elution profile of fragment 1 of FIG. 4.

FIG. 19 is a comparison of MIPC chromatograms showing the yield obtained after PCR with different DNA polymerase enzymes.

FIG. 20 is a comparison of MIPC chromatograms showing fidelity of PCR products obtained using different DNA polymerase enzymes.

FIG. 24 shows the temperature dependent separation of homo- and heteroduplexes.

FIG. 25 shows the change in retention time with temperature of the peaks of the homo-and heteroduplexes from FIG. 24.

FIG. 26 is a schematic of a stepwise melting of a theoretical three domain DNA molecule.

FIG. 40 is a reference chart used to select a mobile phase composition for eluting double stranded polynucleotides.

FIG. 41 shows an embodiment of a mobile phase gradient for mutation detection by DMIPC.

DETAILED DESCRIPTION OF THE INVENTION

Figure 1:
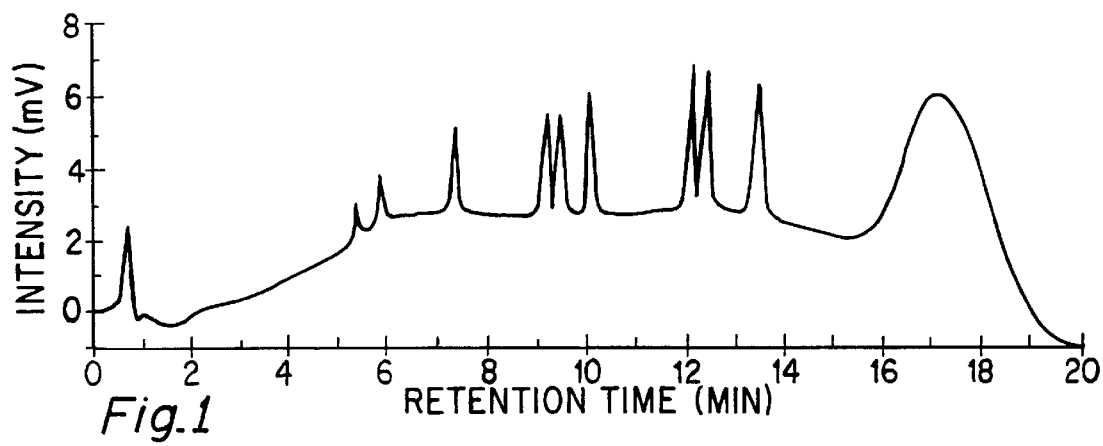
FIG. 1 is a MIPC separation of pUC18 DNA-HaeIII digestion fragments on a column containing alkylated poly(styrene-divinylbenzene) beads.

In its most general form, the subject matter of the present invention primarily relates to an improved method for separating mixtures homoduplex and heteroduplex DNA fragments having the same base pair (bp) length using MIPC. Since such a separation is performed under partially denaturing conditions, i.e., at an elevated temperature which is sufficient to denature a heteroduplex at the site of bp mismatch, the separation process will be called Denaturing Matched Ion Polynucleotide Chromatography (DMIPC) herein.

A separation process called "Denaturing HPLC" (DHPLC) has been used to detect mutations by separating a heteroduplex (resulting from the presence of a mutation) and a homoduplex having the same bp length. This separation is based on the fact that a heteroduplex has a lower melting temperature (Tm) than a homoduplex. When DHPLC is carried out at a partially denaturing temperature, i.e., a temperature sufficient to denature a heteroduplex at the site of base pair mismatch, homoduplexes can be separated from heteroduplexes having the same base pair length (Hayward-Lester, et al., *Genome Research*, 5:494 (1995); Underhill, et al., *Proc. Natl. Acad. Sci. USA* 93:193 (1996); Doris, et al., DHPLC Workshop, Stanford University, (1997)). These references and the references contained therein are incorporated herein in their entireties. Thus, the use of DHPLC was applied to mutation detection (Underhill, et al., *Genome Research* 7:996 (1997); Liu, et al., *Nucleic Acid Res.,* 26:1396 (1998))

DHPLC can separate heteroduplexes that differ by as little as one base pair under certain conditions. However, separations of homoduplexes and heteroduplexes can be poorly resolved. Artifacts and impurities can also interfere with the interpretation of DHPLC separation chromatograms in the sense that it may be difficult to distinguish between an artifact or impurity and a putative mutation (Underhill, et al., *Genome Research* 7:996 (1997). For these and other reasons, which will soon become apparent, the presence of mutations may even be missed entirely (Liu, et al., *Nucleic Acid Res.* 26:1396 (1998)). For example, if a mutation is located in a high melting domain of DNA fragment, it may not be possible to detect that mutation using the known art. The references cited above and the references contained therein are incorporated in their entireties herein.

Applicants have discovered a chromatographic separation process called Matched Ion Polynucleotide Chromatography (MIPC) which can separate DNA fragments comprising 10 to 1500 base pairs based on the size of the fragments when the chromatography is conducted at non-denaturing temperature, typically less than or equal to 50° C. The term "Matched Ion Polynucleotide Chromatography" as used herein is defined as a process for separating single and double stranded polynucleotides using non-polar separation media, wherein the process uses a counter-ion agent, and an organic solvent to release the polynucleotides from the separation media. When MIPC is conducted at partially denaturing temperature, i.e. a temperature sufficient to denature a heteroduplex at the site of base pair mismatch, the process is called herein "Denaturing Matched Ion Polynucleotide Chromatography" (DMIPC). DMIPC can be used to detect mutations which differ from wild type by even a single base pair. Applicants have distinguished their mutation detection process from DHPLC by discovering and addressing many heretofore unrecognized aspects of mutation detection analysis by MIPC.

MIPC uses unique non-polar separation media which comprises organic polymers, silica media having a non-polar surface comprising coated or covalently bound organic polymers or covalently bound alkyl and/or aryl groups, continuous non-polar separation media, so called monolith or rod columns, comprising non-polar silica gel and organic polymer. The separation media used in MIPC can be porous or non-porous. A detailed description of the MIPC separation process, MIPC separation media, and MIPC systems is found in U.S. Pat. No. 5,772,889 (1998) to Gjerde and in co-pending U.S. patent applications Ser. No. 09/058,580 filed Apr. 10, 1998 (abandoned); Ser. No. 09/058,337 filed Apr. 10, 1998 (abandoned); Ser. No, 09/065,913 filed Apr. 24, 1998, now U.S. Pat. No. 5,986,085; Ser. No. 09/081,040 filed May 18, 1998, now U.S. Pat. No. 5,997,742; Ser. No. 09/081,039 filed May 18, 1998, now U.S. Pat. No. 5,972, 222; and Ser. No. 09/080,547 filed May 18, 1998, now U.S. Pat. No. 6,017,457. MIPC systems and separation media are commercially available (Transgenomic, Inc. San Jose, Calif.)

The quality of MIPC separations of DNA fragments is very sensitive to the presence of multivalent cations anywhere in the in solvent and sample flow path. Therefore, MIPC separation media are washed with acid prior to column packing. In addition, freshly packed columns are washed with 0.1M EDTA solution at least 50° C., and preferably at least 70° C. to ensure removal of residual traces of multivalent cations from the separation media and the column interior. Columns and all solution contacting surfaces of an MIPC system comprise materials which do not release multivalent metal cations e.g., coated stainless steel, titanium, polyetherether ketone (PEEK) or any combination thereof. To further ensure long column life and effective separations after many uses, the columns and samples are additionally protected from adventitious multivalent cations by placing guard cartridges containing multivalent cation capture resin in-line between the solvent reservoir and the column and/or injection port.

Applicants have surprisingly found that, when MIPC is used for mutation detection, the method is even more sensitive to purity of the separation media, the presence of trace levels of multivalent cations, and other separation parameters. A column that operates well for MIPC may not operate for DMIPC until additional cleaning is performed; the cleaning processes can include flushing with organic solvents and/or chelating agents to remove contaminants. Thus, the requirement for preventing contamination with multivalent cations is even more stringent for detection of mutations using DMIPC.

Samples to be analyzed for the presence or absence of mutations often contain amounts of material too small to detect. The usual first step in mutation detection assays is, therefore, sample amplification using the PCR process. PCR amplification comprises steps such as primer design, choice of DNA polymerase enzyme, the number of amplification cycles and concentration of reagents. Each of these steps, as well as other steps involved in the PCR process affects the purity of the amplified product. Although the PCR process and the factors which affect fidelity of replication and product purity are well known in the PCR art, these factors have not been addressed, heretofore, in relation to mutation detection using MIPC. As a result, PCR induced mutations, wherein a non-complementary base is added to a template, are often formed during sample amplification. Such PCR induced mutations make mutation detection results ambiguous, since it may not be clear if a detected mutation was present in the sample or was produced during the PCR process. Unfortunately, many workers in the PCR and mutation detection fields make the erroneous assumption that PCR replication has essentially "perfect" fidelity and PCR induced mutations are generally not taken into consideration in mutation detection analyses. This approach can result in false positives. Applicants have recognized the importance of optimizing PCR sample amplification in order to minimize the formation of PCR induced mutations and ensure an accurate and unambiguous analysis of putative mutation containing samples. The use of MIPC by Applicants to identify and optimize the factors affecting PCR replication fidelity will be discussed herein below.

Other aspects of mutation detection by MIPC which have not been heretofore addressed, comprise improved methods for treating of materials comprising chromatography system components, improved methods for treating separation media, methods for solvent pre-selection to minimize methods development time, methods for optimum temperature pre-selection to effect partial denaturation of a heteroduplex during DMIPC and optimization for rapid DMIPC analysis using automated high throughput mutation detection screening assays. Another important discovery by Applicants takes advantage of the unique mechanism of MIPC to concentrate the polynucleotides in a sample by a plurality of applications onto a MIPC column. This novel method obviates the need to concentrate samples by solvent evaporation which may cause sample degradation or introduce contaminants.

Therefore, Applicants have devised a novel and comprehensive protocol which addresses the problems in the prior art described above. This protocol comprises all the steps necessary to ensure the accuracy, reproducibility and speed of mutation detection using MIPC. Such a comprehensive approach to mutation detection using MIPC has not been previously described. For the sake of clarity, the various aspects of the protocol of this invention will be described under their individual headings. An optimal embodiment of the present invention includes implementation of all of the aspects described herein in order to achieve unambiguous, accurate and reproducible mutation detection results using MIPC.

For purposes of organization, the following presentation is divided into sections: Sample Preparation; Primer Design; Optimization of PCR; Temperature Selection; Mobile Phase Selection; Column Preparation and Maintenance.

Analysis of polynucleotides is often hindered by a dilute sample wherein the concentration of polynucleotide is too low to detect or the sample volume is too large. The sample can be subjected to a process for reducing the volume until a polynucleotide concentration is reached which is sufficient to detect. An example is evaporation with or without heating of the solution. Alternatively, the sample can be treated with a precipitating agent, e.g., ethanol, acetonitrile or other organic solvents. There are also methods based on the use of solid media such as those based on ion exchange (e.g., as available from Qiagen, Valencia, Calif.), silica gel (e.g., as sold by CPG, Inc. Lincoln Park, N.J.), and polymers (e.g., as sold by Hamilton, Inc., Reno, Nev.). These approaches for concentrating the sample are inconvenient and time consuming, and can subject the sample to possible inaccurate collection, contamination, degradation, or accidental loss.

There is a need, therefore, for a rapid, sample concentration method. Applicants have surprisingly discovered that in Matched Ion Polynucleotide Chromatography (MIPC), polynucleotides bind to the stationary phase and are released all at once, in a tight band, in order of base pair length only when the organic solvent concentration in the mobile phase is sufficient to release a corresponding base pair length fragment. The term "release" is not one that is normally used in liquid chromatography. The term is used for MIPC because the conditions at which the DNA is adsorbed to the separation media and at which is fully dissolved in the mobile phase are (1) well defined and (2) have small differences with respect to conditions required to separate different fragment lengths. For example, the change of concentration of bulk acetonitrile from which there is complete adsorption of a 102 bp DNA fragment to the separation media to complete desorption is less than 2%. Larger fragments require a larger range, but the total range of acetonitrile change for the separation of a range of 100–600 bp of DNA is 7.5% acetonitrile, which can be performed over a 5 minute gradient.

Without wishing to be bound by theory, it is believed that during a gradient as performed in MIPC, the DNA is released from the top of the column. The release may be gradual, but as the concentration of the acetonitrile is increased by the gradient elution process, the fragment will travel faster until it is traveling at the linear velocity of the mobile phase. Based on experiments comparing 1 cm and 5 cm long columns, it is estimated that the release process with the conditions reported in these examples, the release length is 1 cm or less. Thus, the separation of the fragments is based mostly on the top 20% of a 5 cm column and especially on the top thin section of the column bed. This means that the integrity or uniformity of the top of the column bed is much more important the length of the column for achieving high resolution separations. This is not to say that the length of the column cannot be made to be important when elution conditions are changed to small gradients or isocratic separation conditions.

The term "Matched Ion Polynucleotide Chromatography" as used herein is defined as a process for separating single and double stranded polynucleotides using non-polar separation media, wherein the process uses a counterion agent, and an organic solvent to release the polynucleotides from the separation media. MIPC separates polynucleotides based on size under non-denaturing conditions, i.e., less than about 50° C. As discussed herein, an organic solvent concentration in the mobile phase sufficient to elute a polynucleotide of known base pair length can be predetermined from a reference relating organic solvent concentration and base pair length. For a selected concentration of organic solvent in the mobile phase, only a single base pair length polynucleotide (and all shorter polynucleotides) will elute form the column in a tight band. As an illustration, if a polynucleotide mixture containing 100 bp and 400 bp fragments is applied to an MIPC column, when the column is eluted with a mobile phase containing sufficient organic solvent concentration to elute the 100 bp fragment, but not sufficient to elute the 400 bp fragment, the latter will remain at the top of the column, even after large volumes of mobile phase or multiple injections have been run through the column. This result is quite different from conventional reverse phase chromatography wherein a quantity of organic solvent in the mobile phase sufficient to elute one mixture component will generally partially elute other mixture components of interest, albeit slowly. In such a case, the later eluting components will generally be broad, poorly defined peaks. In contrast, during MIPC the later eluting mixture components elute in sharp bands as soon as a sufficient concentration of organic solvent is added to the mobile phase.

In a main aspect of the present invention, Applicants have advantageously used this property of the MIPC process to obviate the prior art methods of processing highly dilute samples prior to chromatographic analysis. The present invention is an improved method for separating a sample mixture of polynucleotides by MIPC wherein the concentration of polynucleotides in the sample mixture is contained in a large volume in which the sample concentration is below a determined threshold concentration. An example of such a threshold is the limit of detection of a UV absorbance signal which is at or below the background signal. A particular example is a 3 μL injection containing less that about 0.3 ng DNA.

The improvement comprises applying the sample to an MIPC column in more than one aliquot or by a large aliquot (e.g., greater than about 20 μL) whereby the sample accumulates and is concentrated on the column. Polynucleotide samples, generally double stranded DNA, are applied in a solvent or mobile phase which has a concentration of organic component less than a concentration necessary to elute the polynucleotides from the MIPC column. Since the organic solvent concentration in the mobile phase is not sufficient to elute the polynucleotides, the polynucleotides applied to the column from a plurality of aliquots, simply accumulate and concentrate, at the top of the column. This improvement obviates the need to concentrate the sample by evaporation and, therefore, eliminates a step which can degrade the sample. This is extremely important, since eliminating a step which can degrade the sample concomitantly eliminates a source of ambiguity in the analysis.

For very large injection volumes, i.e., greater than about 20 μL, it may be necessary to add counterion agent, e.g. TEAA, to the sample prior to injection.

In a preferred embodiment, the plurality of sample aliquots is applied to the MIPC column automatically by means of a sample autoinjector. In another preferred embodiment, a large dilute sample (e.g., greater than 20 μL) is injected and preconcentrated on the column. The sample contains a counterion agent such as TEAA to facilitate binding of the sample on the column.

In another aspect of the invention, when multiple aliquots of a sample are applied, the column can be subjected to a wash process under isocratic conditions in which an aqueous mobile phase containing a fixed concentration of organic solvent which is not sufficient to elute any of the polynucleotides of interest. This process washes away impurities such as salts, nucleotide bases, buffers, and other debris, but leaves the polynucleotide sample in a concentrated band at the top of the column.

The mobile phase preferably comprises a counterion agent and an organic solvent selected from the group consisting of acetonitrile, ethanol, methanol, 2-propanol and ethyl acetate. The preferred organic solvent in the mobile phase is acetonitrile. The concentration of acetonitrile in the isocratic mobile phase is preferably greater than or equal to 2%.

The counterion agent in the mobile phase is selected from the group consisting of lower alkyl primary, secondary, and tertiary amines, lower trialkylammonium salts, and lower quaternary ammonium salts. The preferred counterion agent is triethylammonium acetate due to its volatility.

Figure 2:
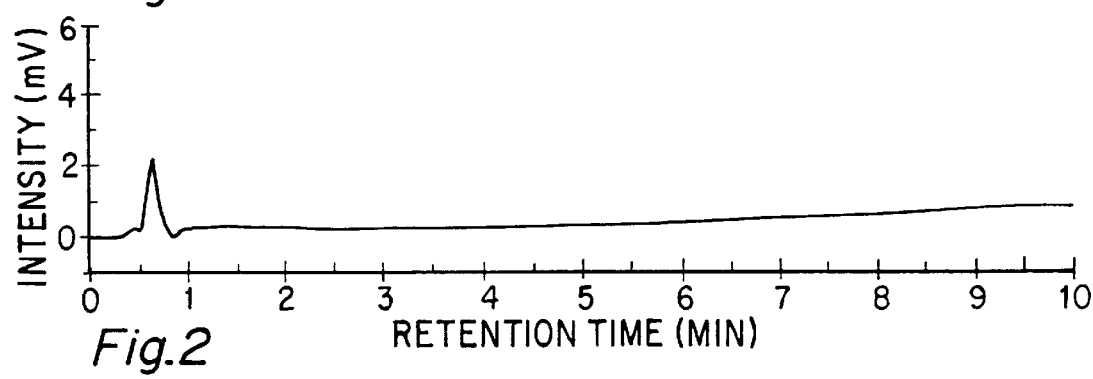
FIG. 2 is a chromatogram obtained after applying a 5 μL sample as in FIG. 1 but flowing a fixed concentration of 35% B through the column under isocratic conditions.
Figure 3:
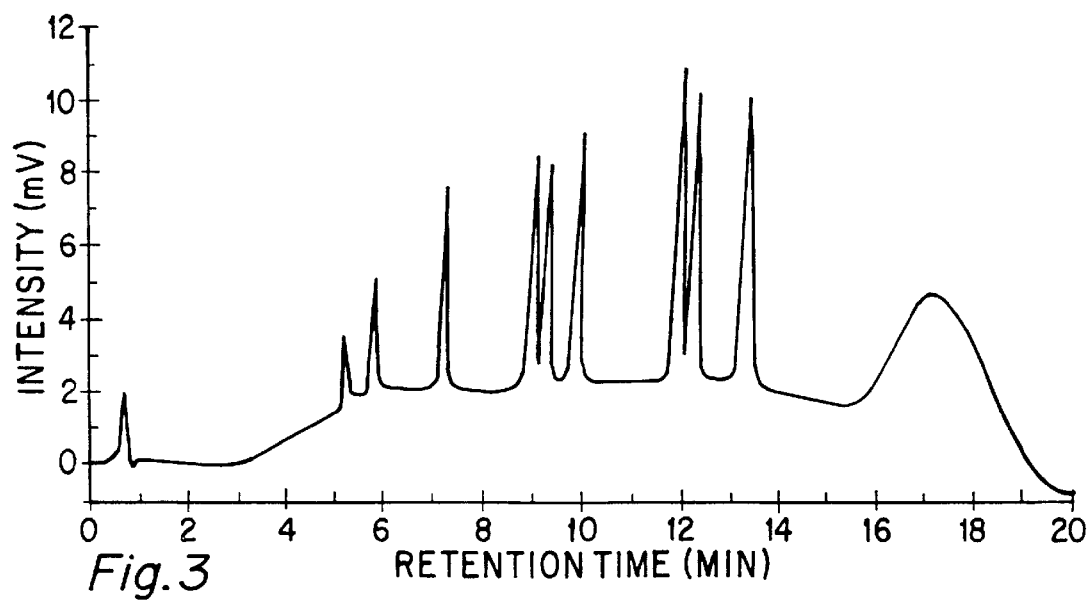
FIG. 3 is a chromatogram obtained after applying a second 5 μL aliquot of the standard pUC18 DNA-HaeIII digest to the column of FIG. 2 and eluting with a gradient as described in FIG. 1.

Following the application of a plurality of sample aliquots and the isocratic elution described above, the sample is separated using gradient elution wherein the concentration of organic solvent in the mobile phase is increased to a final concentration sufficient to elute the longest polynucleotide fragment in the sample. Solvent and gradient conditions suited to a particular size range of DNA fragments can be pre-selected as described herein. Example 1 and FIGS. 1, 2 and 3 are presented to demonstrate the concept and application of this aspect of the invention. FIG. 1 is an MIPC chromatogram of a standard pUC18 DNA-HaeIII digest. A 5 μL sample containing 0.22 μg DNA was applied to the column and the mixture was separated using gradient elution.

In a separate experiment, another 5 μL sample of pUC18 DNA-HaeIII digest was applied to an MIPC column and washed in an isocratic mode with 35% B (where B is 25% acetonitrile plus 0.1M TEAA) for 10 minutes. FIG. 2 shows that no DNA fragments eluted as represented by the flat baseline of the chromatogram. In FIG. 3, a second 5 μL pUC18 DNA-HaeIII digest was injected onto the same MIPC column and the column was eluted with 35% B followed by the gradient described above in relation to FIG. 1. As seen in FIG. 3, the peaks had essentially identical retention times and twice the height as the reference chromatogram shown in FIG. 1. The fact that there was neither a shift in retention time nor peak broadening, demonstrates that the first sample injection remained in a tight band at the top of the column despite isocratic washing for the ten minutes of FIG. 2 and the subsequent application of the second sample.

It will be appreciated that the present method can be used in the case where a sample is contained in a volume which is too small to be accurately injected onto a MIPC column, e.g., less than about 1 μL. In this situation, the sample can be diluted and then injected in multiple aliquots as described hereinabove. Large volume samples can also be loaded onto a MIPC column as a single continuous application, e.g., by using a pump or syringe.

Detection of unknown mutations requires a highly sensitive, reproducible and accurate analytical method. The design of polymerase chain reaction (PCR) primers used to amplify DNA samples which are to be analyzed for the presence of mutations is an important factor contributing to accuracy, sensitivity and reliability of mutation detection. The design of primers specifically for the purpose of enhancing and optimizing mutation detection by MIPC has not been previously reported, and is an important feature of the present invention.

Generally, a fragment, such as an exon, will contain sample sequences having different melting temperatures, but which have a narrow range of variation within any one sample sequence. The sample sequences can be from about 150 to 450 base pairs. It is possible to detect a single base mutation in long fragments, e.g. 1.5 kbase. However, if in such a fragment a mutation occurred in a sample sequence having a high melting point (e.g. a G-C rich region) then it might not be detectable, since high temperatures would be needed to partially denature at the mutation site, and all the other lower melting sequences would denature first.

In an embodiment of the present invention, Applicants have found that the required degree of accuracy is best achieved by seqmenting the exon preferably into 150 to 600 bp sections and more preferably into 150 to 400 bp sections, despite the fact that single base mutations have been detected in 1.5 kb fragments using MIPC.

In one aspect of the invention, Applicants have found that mutation detection of dsDNA using MIPC is more reliable and accurate if the mutation is located within a sample sequence having a narrow melting point range. A range of less than about 20° C. is preferred in the present invention, i.e. any one base in the sample sequence has a melting point that is within about ±10° C. of any other base in the sample sequence. In a more preferred embodiment, the range is less than about 15° C. An example of a sample sequence is the constant melting domain as described by Lerman et al. (*Meth. Enzymol.* 155:482 (1987)).

The change in the structure of DNA from an orderly helix to a disordered, unstacked structure without base pairs is called the helix-random chain transition, or melting. Statistical-mechanical analysis of equilibria representing this change as a function of temperature for double-stranded molecules of natural sequence has been presented by Wartell and Montroll ((*Adv. Chem. Phys.* 22: 129 (1972)) and by Poland (1974). The theory assumes that each base pair can exist in only two possible states-either stacked, helical, and hydrogen bonded, or disordered. It permits calculation of the probability that each individual base pair is either helical or melted at any temperature, given only the base sequence and a very small number of empirically calibrated parameters. The statistical-mechanical theories take into account the differing intrinsic stabilities of each base pair or cluster of neighboring base pairs, the influence of adjacent helical structure on the probability that a neighboring base pair is helical or melted (the cooperativity), and the restrictions on the conformational liberty of a disordered region if it is bounded at both ends by helical regions. Poland (*Cooperative Equilibria in Physical Biochemistry,* Oxford Univ. Press, Oxford, England, (1978)) has presented a relatively accessible explanation of the theory and its development from simple principles. Wartell and Benight (*Phys. Rep.* 126: 67 (1985)) have recently reviewed the theory and presented a careful comparison of theoretical and experimental results. A more general survey has been presented by Gotoh (*Adv. Biophys.* 16: 1 (1983)). Since the theory is based on distribution of each base pair between only two states, it does not take into account patterns of pairing between the two strands that do not occur in the original helix, nor pairing within sections of the separated strands. The relevance of such considerations has not yet been demonstrated, but they can be imagined to occur as melting intermediates in relatively long molecules where the calculated and experimental results may show significant discrepancies. Apparent departure of experimental results from theoretical expectation occurs for some sequences because of exceedingly slow approach to equilibrium (Suyama et al. *Biopolymers* 23: 409 (1984); Anshelevich et al, *Biopolymers* 23: 39 (1984)).

Iteration of the probability calculation at a closely spaced series of temperature steps and interpolation permit determination of the midpoint temperature at which each base pair is at 50/50 equilibrium between the helical and melted states. The MELT program provides the midpoint temperature and some other functions. A plot of midpoint temperature as a function of position along the molecule is called a melting map. It clearly shows that the melting of nearby base pairs is closely coupled over substantial lengths of the molecule despite their individual differences in stability. The existence of fairly long regions, 30–300 bp, termed domains, in which all bases melt at very nearly the same temperature, is typical. The melting map directly delineates the lowest melting domains in the molecules.

In the instant specification, when referring to a base pair, the term "melting point" is synonymous with the term "midpoint temperature", as described by Lerman et al. (1987).

At a partially denaturing temperature, a heteroduplex having a base pair mismatch within a sample sequence will denature at the site of the mismatch, while the rest of the sample sequence will remain intact. The partially denatured heteroduplex can be separated and detected using DMIPC.

In another aspect, the present invention is a method for preparing the sequence of the normal dsDNA fragment to segment, i.e., mark off, the dsDNA fragment into sample sequences of nucleotides having a melting point range of less than about 15° C., each sample sequence having a first end and a second end opposite thereto. A selected sample sequence is amplified by PCR using both forward and reverse primers which flank the first and second ends of the sequence.

In an important aspect of the present invention, when the sequence of a DNA fragment to be amplified by PCR is known, commercially available software can be used to design primers which will produce either the whole fragment, or any sample sequence within the fragment. The melting map of a fragment can be constructed using software such as MacMelt® (BioRad Laboratories, Hercules, Calif.), MELT (Lerman et al. *Meth. Enzymol.* 155:482 (1987)), or WinMelt™ (BioRad Laboratories).

In still another aspect, the present invention is a method for analyzing the PCR amplified sequence (amplicon) by MIPC. Prior to analysis by MIPC, the sample is mixed with a standard, such as a wild type homoduplex DNA, and the mixture is subjected to a hybridization process in which the mixture is heated and reannealed to form a mixture of homoduplexes and heteroduplexes.

In yet another aspect, the present invention concerns a method for improved primer design for mutation detection analysis by MIPC. The overall design process design consists of both long range and short range primer design. In long range primer design, the objective is to design primers that produce good quality PCR products. "Good quality" PCR products are defined herein to mean PCR products produced in high yield and having low amounts of impurities such as primer dimers and PCR induced mutations. Good quality PCR can also be affected by other reaction parameters, such as the enzyme used, the number of PCR cycles, the concentration and type of buffer used, temperature thermal cycling procedures and the quality of the genomic template. Methods for producing good quality PCR products are discussed by Eckert et al. (PCR: *A Practical Approach,* McPherson, Quirke, and Taylor eds., IRL Press, Oxford, Vol. 1, pp. 225–244, 1991). This reference and the references therein are incorporated herein in their entireties.

Short range primer design should fulfill two requirements. First, It should fulfill all the requirements of long range primer design and give good quality PCR products. In addition, it must produce fragments that allow the MIPC method to detect a mutation or polymorphism regardless of the location of the mutation or polymorphism within the amplified fragment. For example, large DNA fragments, having up to several thousand base pairs, can be amplified by PCR. If the only goal of the amplification is to replicate the desired fragment, then there is a large latitude in the design of primers which can be used for this purpose. However, if the purpose of a PCR amplification is to produce a DNA fragment for mutation detection analysis by DMIPC, then primers must be designed such that the fragment produced in the PCR process is capable of being detected, and will produce a signal, when analyzed by DMIPC. In a preferred embodiment of the invention, the fragment length is 150–600 bp. In the most preferred embodiment, the fragment length for DMIPC mutation detection analysis is 150–400 bp.

There are two goals of designing short range primers. One goal for primer design is if the analysis is used as a "screening" test. Another goal is in analysis for research or diagnostic purposes. "Screening" is defined herein as the study or analysis of DNA fragments to determine if the fragments contain variations (polymorphisms) in a population and correlate that variation to disease. It is to be understood that, within the context of this invention, the term "mutation" includes polymorphism. When DMIPC is used as a screening technique, then an important aspect of the present invention is a method for designing primers to produce a fragment in which a putative mutation can be detected, regardless of where the mutation site is located within the fragment. If the mutation is known, on the other hand, then the primer design can be further refined so that the analysis is optimized, i.e., the resolution of the homoduplex and the hetroduplex peaks is maximized. By improving the resolution for the analysis of known mutations, accuracy of analysis can be performed. Improved resolution is required for diagnostic mutation applications. Furthermore, with improved resolution, automatic identification of the positive presence of mutation can be more easily implemented with appropriate software and an algorithm that overlays and comparatively measures the peaks of the wild type and mutant DNA samples.

In an important aspect, the method of the present invention allows the determination of whether the amplified fragment contains a region within which it would be difficult to detect a putative mutation. Applicants have discovered that a mutation can be detected by DMIPC even if located in a position within a fragment in which it would be difficult to detect by other methods, e.g., in the middle of a fragment or in a high melting domain. Mutations so located can be detected by DMIPC in three ways. In one embodiment of this aspect of the invention, a "peak overlay" technique can be used, wherein a wild type standard peak is overlayed onto a partially resolved mutation-containing sample peak. The area of the standard peak is subtracted from the area of the sample peak. If the difference in area is greater than or equal to 10% of the standard, the sample is considered to contain a mutation. In a second embodiment of this aspect of the invention, if the fragment contains a region where the melting is high, the DMIPC analysis can be performed at two or more temperatures, each temperature corresponding to a different melting domain, as further described hereinbelow. It has been surprisingly discovered by Applicants that for a multi-domain fragment, that changing the selection of primers has a dramatic effect on the melting profile of the amplified sequence predicted by a software program. This observation is advantageously used in a third embodiment of this aspect of the present invention in which primers are re-selected to change the melting map of the fragment of interest to lower the differences between the Tm's of the domains in the fragment. As stated hereinabove, there are two situations under which short range primer selection is performed. One is if the mutation is to be used for screening for variation in a genome. The other is a diagnostic or clinical application where the presence of a particular mutation is measured in a set of samples. The following summarizes the options for preferred short range primer selection in each of these situations.

Screening applications require that the mutation can be detected regardless of where the mutation might be located on the fragment. In this situation, the mutation might be located in the middle of the fragment or in a higher melting domain, both cases where it is more difficult to detect. It is preferred than the range of melting variation of the fragment is no greater than 10° C. and most preferred is the range of variation is no greater than 5° C.

Another method of primer design for screening applications is to design the primers so that the region of interest is at a lower melting domain within the fragment. In this case the primers are preferred to be designed so that the fragment being measured will overlap the regions of interest as the analysis is performed traveling down the exon. In these cases, the temperature difference between the higher melting domain and the lower melting domain is preferred to be greater than 5° C. and most preferred to be greater than 10° C.

Once the mutation of interest is identified, primers can be redesigned for R&D diagnostic or clinical applications. In these cases, the mutation is preferably located within 25% or 25 bases of the end which ever is closer to the end. The other end of the fragment contains a higher melting domain of preferably 5° C., more perferably 10° C. higher, and most perferably 15° C. higher than the lower domain where the mutation is located. If the primer selection does not result in a high melting domain on the opposite end of the fragment, then a G-C clamp can be applied. The size of the clamp can be up to 40 bp, but can be as little as 4–5 bp, with 10–20 bp most preferred.

If it is not possible to design primers which will produce, upon PCR amplification, domains having a constant melting range or domains within a fragment which are sufficiently close in Tm, then it may be necessary to lower the Tm of a domain of interest for successful mutation detection by DMIPC. This can be done by substituting dGTP with the analog 7-deaza-2'-dGTP which is known to effectively lower the melting temperature of G-C base pairs (Dierick et al., *Nucl. Acids Res.* 21:4427 (1993)). If it is necessary to raise the Tm of the domain, then 2,6-aminopurine can be used in place of dGTP in the PCR amplification.

Once the mutation of interest is identified, primers can be redesigned for research and development diagnostic or clinical applications. In a preferred embodiment of the present invention, the primers are selected to produce a fragment having the mutation near one of the ends. This could be within about 25 bases of one of the ends for fragments having similar length to the examples described herein, or this could be within about 25% of the total length from either end. Also in a preferred embodiment of the invention, the primers are selected to produce a fragment having a domain that has at least a 5° C. higher Tm at the end opposite to the end containing the mutation.

In a most preferred embodiment, the primers are selected so that the mutation is located in a "lower melting" domain of the fragment. However, a mutation can also be detected by DMIPC in a high melting domain of the fragment either if the high melting domain does not have a melting temperature that is too different from other domains in the fragment or if a higher column temperature is used that is optimized for the higher melting domain of the fragment.

Figure 6:
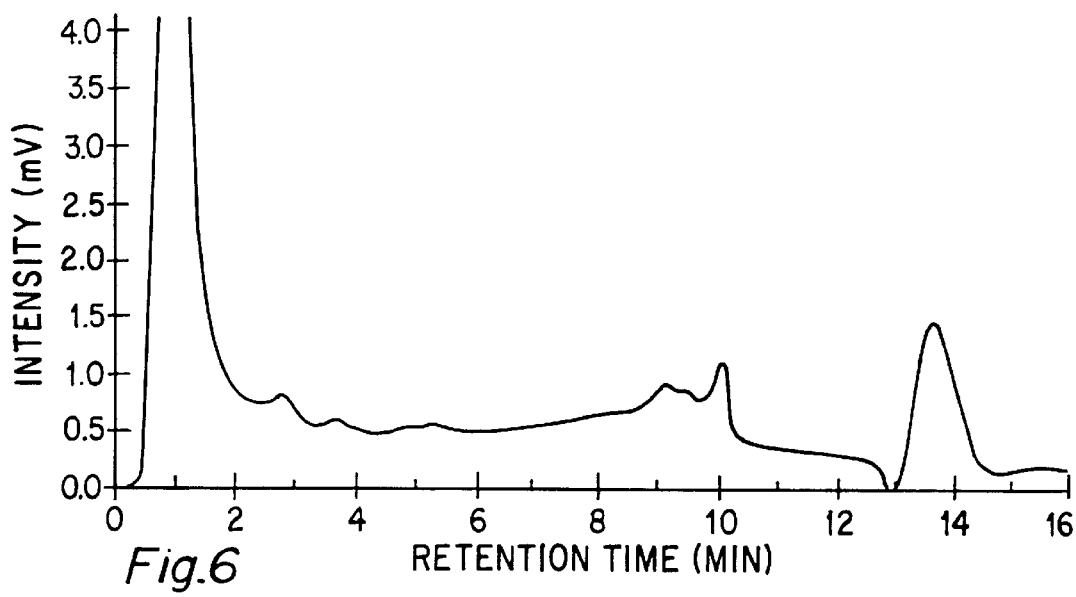
FIG. 6 shows the DMIPC elution profile of fragment 2 of FIG. 4.
Figure 7:
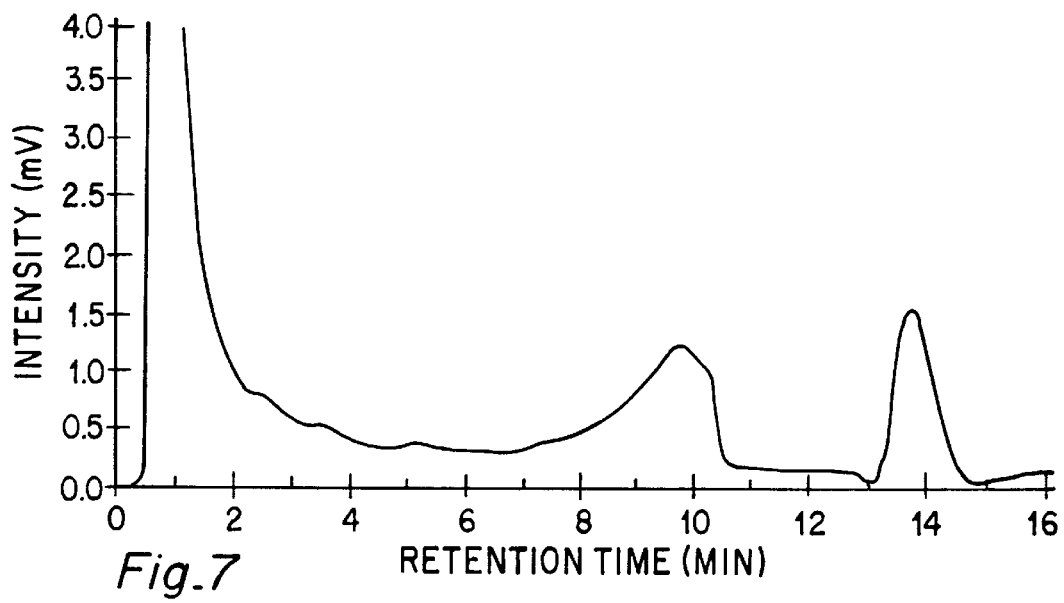
FIG. 7 shows the DMIPC elution profile of fragment 3 of FIG. 4.

The method of the invention for the design of primers is illustrated by Example 2. A p53 DNA template containing a mutation was amplified by means of PCR processes in which three different sets of primers were used. Each primer set was designed to produce amplicon fragments having the mutation located in a different melting domain. The melting maps, calculated using WinMelt™, showing the melting domains of the three amplicon fragments of similar size and the relative position of mutation within the fragments is shown in FIG. 4. FIGS. 5, 6, and 7 show the effects of primer design on the DMIPC mutation detection analysis results of three selected amplicon fragments. The best resolution of homoduplexes and heteroduplexes, showing four distinct peaks, was seen in FIG. 5, representing fragment 1, in which the mutation was located near the end of the fragment in a constant melting domain. The poorest resolution, showing one broad peak, was seen in FIG. 7, representing fragment 3 in which the mutation was located near the middle of the fragment.

Example 3 provides a further illustration of the use of the method of the present invention. Primer design which located the mutation within about 20% of either end gave the best resolution upon DMIPC analysis. Fragment 1 (in FIG. 8), with the mutation located in a constant melting domain, gave the best resolution (FIG. 9), while the poorest resolution was seen (FIG. 12) when the mutation was located near the middle of a fragment (fragment 4 in FIG. 8).

If it is not possible to design a primer which will produce, upon PCR amplification, a high melting domain on the opposite end of the fragment, then in an embodiment of the invention, a G-C clamp can be applied to increase the melting temperature at the desired end (Myers et al., *Nucleic Acids Res.* 13:3111 (1985)). G-C clamping is a technique in which additional G or C bases are included on the 5' end of one or both of the primers. The polymerase enzyme will extend over these additional bases incorporating them into the amplified fragment thereby raising the melting temperature of the end(s) of the fragment relative to that in the vicinity of the mutation. The size of the G-C clamp can be up to 40 bp and as little as 4 or 5 bp. The most preferred G-C clamp for mutation detection by DMIPC is 10 to 20 bp.

In denaturing gradient gel electrophoresis, G-C clamps are required (Sheffield et al., *Proc. Natl. Acad. Sci. USA* 86:232 (1989)) for almost all fragment mutation analysis whereas in DMIPC, G-C clamps are rarely needed. An exception is perhaps where the mutation is in the center of the fragment and the length is less than 100 bp and the melting profile is flat or in cases where the mutation in a high melting region of the fragment and a higher melting region is in effect a G-C clamp. In these cases, proper primer selection will result in a fragment in which the mutation can be detected.

The long range primer design described above can be further refined by local primer design in which several other factors should be considered. For example, primers with non-template tails, such as universal sequencing primers or T7 promoters, should be avoided. The preferred primer has a Tm of about 56° C. The difference in Tm between the forward and reverse primers is preferably about 1° C. The difference in Tm between primer and template is preferably 25° C. The 3'-pentomer of each primer should be more stable than $\Delta G°=-6$ kcal/mol (i.e., more negative). Any possible primer dimers should be less stable than the 3'-pentomer by at least 5 kcal/mol (i.e., 5 kcal more positive). Any primer self annealing loops should have a Tm of less than 12° C. Primers should be of high purity without failure sequences. To avoid degradation, storage in Tris-HCl (pH 8.0) buffer is preferable to pure water.

Figure 13:
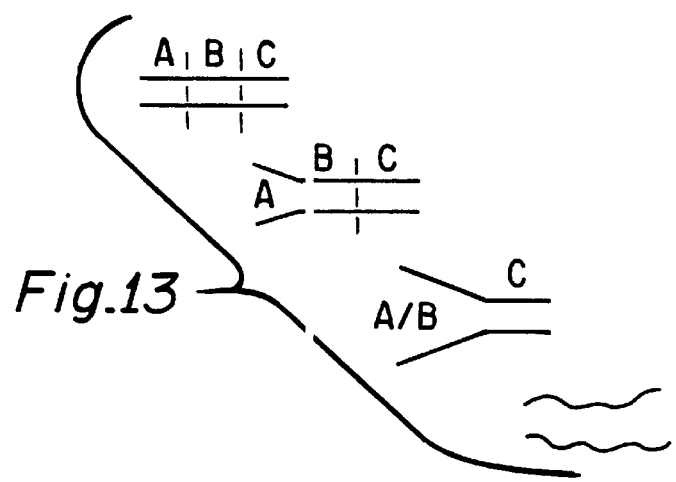
FIG. 13 is a schematic diagram showing stepwise melting of a theoretical three domain DNA molecule.

In some cases, it is more convenient to directly screen a long fragment, e.g., an exon, of up to 1.5 kb for mutations. Such long fragments generally contain multiple melting temperature domains. Double-stranded DNA fragments melt in a series of discontinuous steps as different regions with differing thermal stabilities which denature in response to increasing temperature. These different regions of thermal stability are referred to as "domains", and each domain is approximately 50–300 bp in length. Each domain has its own respective Tm and will exhibit thermodynamic behavior which is related to its respective Tm. The presence of a base mismatch within a domain will destabilize it, resulting in a decrease in the Tm of that domain in the heteroduplex relative to its fully hydrogen-bonded counterpart found in the homoduplex. Generally. the presence of a base mismatch will lower the Tm by approximately 1°–2° C. FIG. 13 depicts the melting of a theoretical three domain fragment in schematic form.

As described above, every DNA fragment is comprised of one or more regions of independent thermal stability or domains. The Tm of a domain serves as a thermodynamic signature and determines the thermodynamic behavior of a domain. As depicted in the schematic in FIG. 13, as the temperature is gradually increased domain A will denature first because its Tm is lower than that of domain B or C. Domain B has an intermediate Tm and would melt next, and domain C would be the last to melt because its domain has the highest Tm within this fragment.

Rather than gradually "unzippering" from one end to the other, the base pairs within a domain melt in unison over a very narrow temperature range. The denaturing of a domain is characterized by a sigmoidal profile (FIG. 14) which indicates "cooperativity" among the base-pairs comprising the domain. The midpoint of the inflection (slope) is the Tm and corresponds to a temperature at which the domain exists in equilibrium between single and double stranded states. As the temperature is increased beyond the Tm, the entire domain will rapidly convert to a completely single-stranded conformation.

In the three domain molecule illustrated in FIG. 13, a putative point mutation could be present in any of the domains: A, B or C. In order to establish a high probability of detecting polymorphic mutations or mutations in previously uncharacterized DNA fragments, it is necessary to carefully select one or more temperatures at which fragment analysis will be performed by DMIPC.

The MIPC system is capable of automatically profiling the melting behavior of a DNA fragment by running a series of separations at incremental temperature increases over the entire likely denaturation range (e.g. 50°–70° C.).

Figure 14:
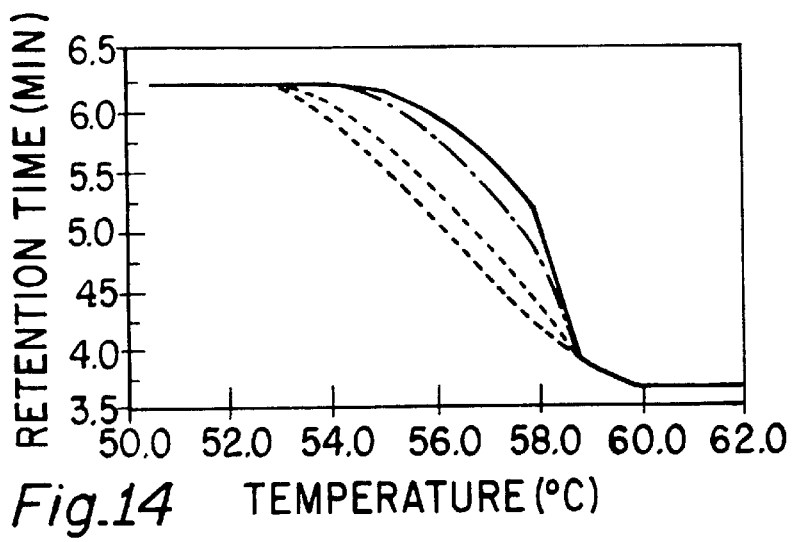
FIG. 14 shows a temperature titration curve of two homoduplexes (upper two curves) and two heteroduplexes (lower two curves).

FIG. 14 depicts the melting of the four related homo- and heteroduplex forms of a DNA fragment (the homoduplexes are represented by dashed lines). These melting profiles illustrate how the midpoints of the heteroduplex inflections are shifted to the left, indicating lower Tms and more rapid elution from the MIPC column compared to the homoduplexes. It is also apparent that the Tms of the heteroduplexes are approximately 1°–2° C. lower than the homoduplexes.

Figure 15:
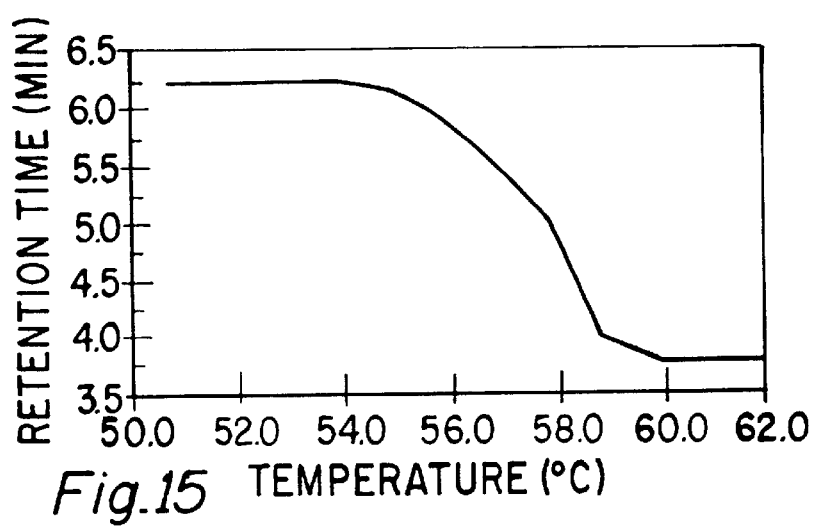
FIG. 15 shows the melting profile for DNA fragment sY81.

FIG. 15 depicts the melting profile of a 230 bp restriction fragment designated sY81. Any domains present in this fragment are now represented by a single sigmoidal curve extending between approximately 54°–59° C. The temperature at this midpoint of the inflection is the Tm of the melting profile of the homoduplex fragment or $Tm_{homo}$. Determining the $Tm_{homo}$ from the melting profile is necessary for selecting an appropriate temperature at which to carry out mutation screening. Since the presence of a base mismatch will lower the Tm of the corresponding heteroduplex domain being scrutinized by approximately 1°–2° C., a fairly accurate estimation can be made of the Tm of the respective heteroduplex fragment, $Tm_{hetero}$, where $Tm_{hetero}=Tm_{homo}-1°$ C.

As indicated above, the appearance of the melting profile indicates that the $Tm_{homo}$ is approximately 56° C. Therefore, the preferred temperature for screening for mutations within this fragment would be $Tm_{hetero}=Tm_{homo}-1°$ C. or 55°. However, given the steepness of the slope created by the inflections for both domains and the closeness of the two domains' Tms, we also know that any domains present in this fragment will be partially denatured at that temperature, In the case where the Tms of two different domains are within 5° C. of one another, it is possible to screen for mutations in both domains simultaneously by selecting a single analysis temperature. However, the temperature selected must be less than or equal to the Tm of that domain which has the lower Tm. If an intermediate temperature is selected, the lower Tm domain in both the heteroduplex and homoduplex fragments will be denatured and the ability to detect mutations in that domain will be lost. If the DNA fragment melts over a temperature range greater than 5° C., more than one temperature must be used to screen the fragment.

Figure 16:
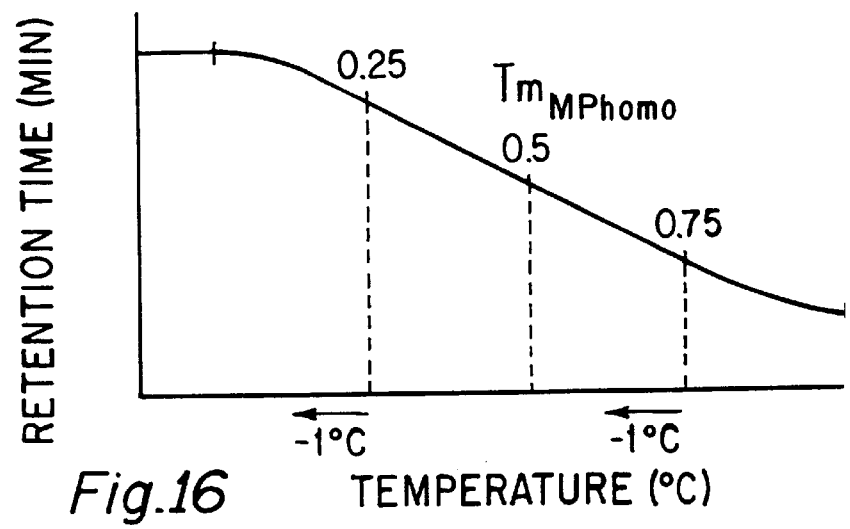
FIG. 16 shows a theoretical melting profile of a three domain DNA fragment in which the domains have melting temperatures of 55° C., 60° C. and 65° C., respectively.

For example, if a DNA fragment contains three domains, A, B and C with Tms of 55° C., 60° C., and 65° C., respectively, the slope of the melting profile will extend over a 10° C. range and be broader than the profile depicted in FIG. 15. This indicates that more than one screening temperature will have to be used to comprehensively screen all of the domains within this fragment for the presence of mutations. Domains A and B can be simultaneously screened at a temperature of 54° C. and domains B and C can be simultaneously screened at 59° C. However, there is no single temperature which will allow all three domains to be screened simultaneously. FIG. 16 depicts a theoretical melting profile for a three domain fragment with Tms of 55° C., 60° C. and 65° C.

When a melting profile which extends over a temperature range greater than about 5° C., the following steps can be used to carry out comprehensive mutation screening, as shown in FIG. 16.

1. Divide the slope of the inflection into quarters.
2. Subtract 1° C. from temperatures at positions 0.25 and 0.75.
3. Carry out the first analysis at a temperature corresponding to position 0.25 less 1° C.
4. Carry out the second analysis at a temperature corresponding to the 0.75 position less 1° C.

The Polymerase Chain Reaction (PCR) described in U.S. Pat. No. 4,683,202 to Mullis was a transforming invention in the field of biotechnology. PCR makes possible the amplification (replication) of minute samples of DNA or other polynucleotides of any base pair length (size) by taking advantage of highly selective enzymes called DNA polymerases, to extend small DNA strands called "primers" along a "template". The minute DNA sample serves as the template. PCR reproduces the complementary sequence of deoxynucleotide triphosphate (dNTP) bases present in the template or any chosen portion thereof. The PCR can be used in conjunction with diagnostic techniques wherein, for example, a DNA sample having a concentration below the limit of detection is amplified by the PCR process, and the larger amount so obtained is subsequently analyzed. In a similar manner, DNA samples obtained from genetic material may be amplified and sequenced, or studied to determine its biological effects.

Apparatus for performing PCR amplifications, e.g. Air Thermo Cycler (Idaho Technologies) and reagents are commercially available from numerous sources, e.g. Perkin-Elmer Catalog "PCR Systems, Reagents and Consumables" (Perkin-Elmer Applied Biosystems, Foster City, Calif.).

PCR is typically run in a buffer at pH 5–8. The buffer contains a double stranded DNA sample to be amplified, a first primer, a second primer, magnesium chloride ($MgCl_2$), and the four deoxynucleotide triphosphates (dATP, dTTP, dCTP, and dGTP) generally referred to as "bases", the building blocks of DNA. The reaction mixture is heated to a temperature (typically 90° C.) sufficient to denature the DNA sample, thereby separating its two complementary polynucleotide strands. Alternatively, the DNA may be denatured enzymatically at ambient temperature using a helicase enzyme. If denaturing is effected by heat and a thermostable DNA polymerase is used, the DNA polymerase is added before the reaction is started. If denaturing is effected by heat and a thermolabile DNA polymerase is used, the DNA polymerase is added after the denaturing step. If denaturing is effected by helicases at ambient temperature, a thermolabilie DNA polymerase may be included with the other reagents before the start of the reaction. Other denaturing conditions are well known to those skilled in the art and are described in U.S. Pat. No. 5,698,400 to Cotton (1997). This reference and the references cited therein are incorporated in their entirety herein. DNA polymerases are commercially available from a variety of sources, e.g. Perkin-Elmer Applied Biosystems, (Foster City, Calif.) and Stratagene (La Jolla, Calif.).

The primers are an oligonucleotide sequence typically consisting of 7–25 nucleotide bases. Primers are usually synthesized chemically in a predetermined defined sequence. The primer sequence is designed to be complementary to an identified portion of the denatured DNA strands to be replicated by PCR. Primers are commercially available from a variety sources, e.g., Synthetic Genetics (San Diego, Calif.). Upon cooling the reaction to about 50° C., each of the primers anneals to its complementary base sequence in each strand of the denatured DNA sample to be replicated. Heated to about 70° C. in the presence of the DNA polymerase, the 4 dNTPs and $Mg^{++}$, replication extends the primers from their 3'—ends by adding complementary dNTPs along the length of the strand. dNTPs are commercially available from a variety of sources, e.g. Pharmacia (Piscataway, N.J.). By repeating this process numerous times, a geometric increase in the number of desired DNA strands is achieved in the initial stages of the process or as long as a sufficient excess of reagents are present in the reaction medium. Thus, the amount of the original DNA sample is amplified.

PCR is well known in the biotechnology art and is described in detail in U.S. Pat. No. 4,683,202 to Mullis (1987); Eckert et al., *The Fidelity of DNA polymerases Used In The Polymerase Chain Reactions,* McPherson, Quirke, and Taylor (eds.), "PCR: A Practical Approach", IRL Press, Oxford, Vol. 1, pp. 225– 244; Andre, et. al., GENOME RESEARCH, Cold Spring Harbor Laboratory Press, pp. 843–852 (1977). These references and the references cited therein, are hereby incorporated by reference in their entireties.

The PCR process is limited in its ability to replicate DNA strands by the specificity of the DNA polymerase used, as well as other features of the reaction. For example, the primers may bind to portions of a DNA strand which are only partially complementary. Such nonspecific primer binding will produce products with an undesired sequence. In addition, the first and second primers may also bind to complementary portions of each other, producing primer dimers. The specificity of DNA polymerases varies with the reaction conditions employed as well as with the type of enzyme used. No enzyme affords completely error-free extensions of a primer. A non-complementary base will be introduced from time to time. Such enzyme related errors produce double stranded DNA products which are not exact copies of the original DNA sample, that is, the products contain PCR induced mutations. Other PCR process variables which may degrade the accuracy or fidelity of DNA replication include reaction temperature, primer annealing temperature, enzyme concentration, dNTP concentration, $Mg^{++}$ concentration, source of the enzyme and combinations thereof.

Most applications of PCR require the highest level of replication fidelity which can be achieved. In particular, detection of mutant genes, the construction of genetically engineered monoclonal antibodies, analysis of T-cell receptor allelic polymorphism, the study of HIV variation in vivo and cloning of individual DNA molecules from the PCR amplified population depend upon high fidelity amplification for their success.

Prior to this invention, PCR products and processes have been monitored by gel electrophoresis or capillary electrophoresis. These methods separate DNA fragments by size but cannot detect PCR induced mutations. The term "PCR induced mutations", as used herein, is defined to mean an insertion, during the PCR process, of one or more bases which are not complementary to their corresponding base in the template. Thus, a PCR induced mutation is a deviation from replication fidelity. Such mutations have been heretofore separated from their normal counterparts by gradient gel electrophoresis or gradient capillary electrophoresis. However, these techniques are operationally difficult to perform, are time consuming, require a great deal of expertise and are not always reproducible. Capillary electrophoresis analysis takes at least 30 minutes. A gel electrophoresis analysis takes several hours. These analytical methods are not optimal for routine analysis of PCR processes where quick setup, ease of use, high throughput, high reproducibility, and quantitative results are necessary.

A need exists, therefore, for an easy to use analytical method which can analyze PCR processes and optimize the PCR process in a predictable manner, in order to minimize deviations from perfect replication. A need also exists for a method for easily separating and collecting pure PCR product from artifacts such as PCR induced mutations and primer dimers.

Minimizing deviations in the PCR replication process can be achieved by modifying a reaction condition or reagent which causes the deviations if the cause of the deviation can be identified. One aspect of this invention is based on the discovery that the product profile obtained from application of the Matched Ion Polynucleotide Chromatography (MIPC) method to PCR reaction products can be used to identify the sources of the deviations from accurate replication.

The term "Matched Ion Polynucleotide Chromatography" as used herein is defined as a process for separating single and double stranded polynucleotides using non-polar separation media, wherein the process uses a counterion agent, and an organic solvent to release the polynucleotides from the separation media. Depending on the conditions, MIPC separates double stranded polynucleotides by size or by base pair sequence and is therefore a preferred separation technology for evaluating and analyzing PCR. When mixtures of DNA fragments are applied to an MIPC column, they are separated by size, the smaller fragments eluting from the column first. MIPC, when performed at a temperature which is sufficient to partially denature a heteroduplex, is referred to as "Denaturing Matched Ion Polynucleotide Chromatography" (DMIPC). Typically, heteroduplexes elute from the column faster than the corresponding homoduplexes during DMIPC.

The parameters which optimize PCR fidelity of replication or yield can be predicted by creating and analyzing a PCR product profile and comparing the profile to a standard product profile to predict which of the many possible PCR parameters require adjustment in order to achieve an optimum fidelity of DNA replication and yield. By analyzing a PCR process and identifying the undesired products in the reaction product profile, the reaction parameter which is responsible for producing the undesired product can be determined and modified in a subsequent PCR process in order to eliminate or minimize said undesired product.

The term "PCR product profile" as used herein is defined to mean the data generated by MIPC as applied to the product of a PCR process. The MIPC data can distinguish the expected product and other components of the reaction mixture from one another. These components comprise desired product(s), byproducts and reaction artifacts. The PCR product profile can be in the form of a visual display, a printed representation of the data or the original data stream.

The preferred method of this invention for generating a PCR product profile is MIPC. The preferred display is a separation chromatogram output of the MIPC process as seen on a video screen or on printed hard copy or the data stream corresponding thereto. Applicants have discovered that MIPC is an efficient analytical method which can separate all the potential products of a PCR process in an accurate, reproducible manner required to quantify the results. Furthermore, the method is easy to implement. MIPC has not previously been used to analyze and optimize PCR processes.

The term "standard profile" as used herein is defined to mean the data generated by the MIPC method when this method was used to separate reference standards related to the PCR process. Reference standards can comprise the expected product of the PCR process, DNA fragments of known base pair length which can be used to calibrate the display for base pair length, primers, primer dimers, heteroduplexes of the expected PCR product or combinations of more than one of these. The standard profile can also comprise an actual PCR process which has been separated by MIPC. The standard profile can be in the form of a visual display, a printed representation of the data or the original data stream.

MIPC is easy to implement, provides reproducible results, and is capable of effectively separating single and double stranded polynucleotides on the basis of both size and base sequence. Operating MIPC at the higher temperatures as used in DMIPC enables the separation of the desired DNA product from PCR induced mutations which differ from the desired product by even a single base. It separates the desired product from any byproducts of the PCR process which represent a deviation from replication fidelity. Byproducts can then be evaluated and identified by comparing their product profile to a selected standard profile as described hereinabove. Methods other than MIPC are either not capable of separating and detecting deviations from replication fidelity and/or, are inaccurate, inconvenient, time consuming and have limited scope. MIPC can separate mixtures of single and double stranded polynucleotides in general and DNA fragments in particular, with essentially none of the limitations of the previously known gel based methods described above. MIPC separations are typically complete in less than 10 minutes, and frequently in less than 5 minutes. MIPC systems (Transgenomic, Inc. San Jose, Calif.) are equipped with computer controlled ovens which enclose the columns and fluid inlet areas. Performing separations of PCR mixtures at the temperature required for partial denaturation (melting) of the DNA at the site of mutation can therefore, be automated and easily performed. The system used for MIPC separations is rugged and provides reproducible results. It is computer controlled and the entire analysis of multiple samples can be automated. The system offers automated sample injection, data collection, choice of predetermined eluting solvent selection based on the size of the fragments to be separated, and column temperature selection based on the base pair sequence of the fragments being analyzed. The separated PCR mixture components provide a reaction product profile which can be displayed either in a gel format as a linear array of bands or as an array of peaks. The display can be stored in a computer storage device. The display can be expanded and the detection threshold can be adjusted to optimize the product profile display. The reaction profile may be displayed in real time or retrieved from the storage device for display at a later time. The product profile display can be viewed on a video display screen or as hard copy printed by a printer.

Figure 18:
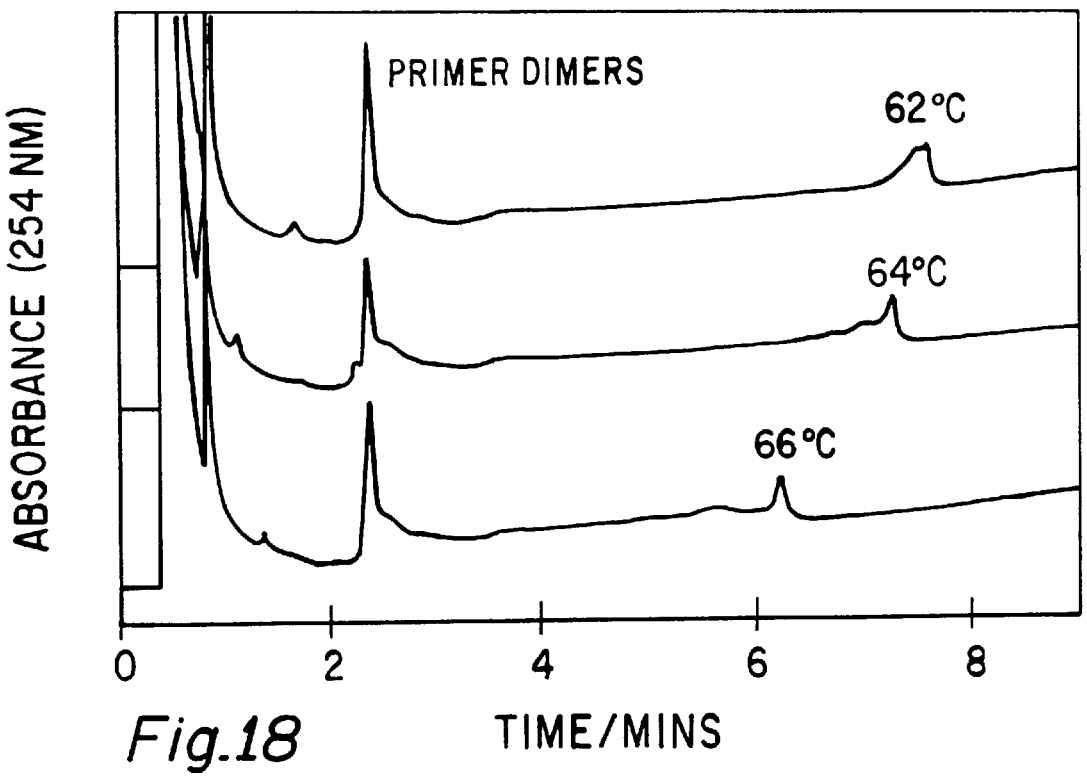
FIG. 18 shows the effect of temperature on the separation of homoduplexes and heteroduplexes by MIPC.

Example 9 describes the effect of temperature on the separation of heteroduplexes (PCR induced mutations) and homoduplexes by MIPC. FIG. 18. shows the results of Example 9 as a product profile of a PCR process (described in Examples 4–8) in the form of a separation chromatogram, wherein the separation was performed at three different temperatures by MIPC. The product fragment contained 405 base pairs. At 62° C., two poorly resolved peaks are seen. When the temperature of the separation process was raised to 64° C. a broad shoulder, representing heteroduplexes resulting form PCR induced mutations, is seen at a lower retention time than the main, sharp peak. The latter peak represents the desired product of the PCR. The appearance of the chromatogram at 64° C. indicates that the heteroduplexes were just starting to denature at the site(s) of a base pair mismatch, as evidenced by the broad, low retention time peak which is poorly separated form the product peak. When the separation temperature was raised to 66° C., complete denaturation occurred at the site of mismatch as evidenced by the complete separation of the PCR induced mutations from the sharp product peak which appears at higher retention time. Furthermore, the lower retention time peak is now partially resolved into at least two heteroduplexes. FIG. 18 also shows a primer dimer peak at very low retention time, near the void volume. As can be seen in FIG. 18 the entire separation was complete in 6–8 minutes. The injection of the sample and temperature of each run were pre-programmed and automatically performed by a computer controlled sample auto-injector and computer controlled column oven.

The series of steps described in Example 4 represent one cycle of the PCR process. These cycles are repeated until the desired amount of product is obtained. After the last cycle, the mixture is usually not denatured again since no additional binding of the primers to their respective templates is necessary. However, in order to analyze a final PCR mixture accurately, all the component double strands must have an opportunity to denature and rehybridize so that all the possible homoduplex and heteroduplex combinations of complementary strands can have an opportunity to form (Example 3).

The degree of specificity of DNA polymerases varies with the reaction conditions employed as well as with the type of enzyme used. No enzyme affords completely error free extension of a primer. Therefore, a non-complementary base may be introduced from time to time. Such enzyme related errors produce double stranded DNA products which are not exact copies of the original DNA sample, but contain PCR induced mutations. Other PCR process features, such as reaction temperature, primer annealing temperature, enzyme concentration, dNTP concentration, $Mg^{++}$ concentration, and combinations thereof, all have the potential to contribute to the degradation of the accuracy or fidelity of DNA replication by the PCR process.

The degree of fidelity of replication of DNA fragments by PCR depends on many factors which have long been recognized in the art. Some of these factors are interrelated in the sense that a change in the PCR product profile caused by an increase or decrease in the quantity or concentration of one factor can be offset, or even reversed by a change in a different factor. For example, an increase in the enzyme concentration may reduce the fidelity of replication, while a decrease in the reaction temperature may increase the replication fidelity. An increase in magnesium ion concentration or dNTP concentration may result in an increased rate of reaction which may have the effect of reducing PCR fidelity. A detailed discussion of the factors contributing to PCR fidelity is presented by Eckert et al., (in PCR: *A Practical Approach,* McPherson, Quirke, and Taylor eds., IRL Press, Oxford, Vol. 1, pp. 225–244, (1991)); and Andre, et. al., (GENOME RESEARCH, Cold Spring Harbor Laboratory Press, pp. 843–852 (1977)). These references and the references cited therein are incorporated in their entirety herein. Thus, availability of a product profile of the PCR process, makes possible the optimization of PCR conditions to improve results in a highly efficient manner. This approach, coupled with the MIPC analytical methods has not been previously reported.

Hence, in another aspect of the invention, PCR reaction product profiles generated by MIPC can be analyzed and evaluated. By comparing a PCR reaction product profile to that of a standard profile, deviations from the standard product profile can be identified and one or more PCR process variables known to cause the observed deviations can be adjusted. Performing a plurality of PCR process cycles using an adjusted process variable followed by analysis of the reaction mixture by MIPC will now show a reduction in deviation of the product profile from a predetermined standard.

As an example of the operation of the invention, the discussion hereinbelow refers to a PCR amplification of 500 base pair DNA fragment under a variety of conditions. Single strand extensions at one or both ends of the product fragment, so-called "overhangs", are not unusual. Because of the sensitivity and separation power of MIPC, such product overhangs appear as shoulders on the product peak and can be confused with PCR induced mutations. In order to eliminate any ambiguity in the assessment of replication fidelity by MIPC, PCR reaction products were routinely treated with HaeIII endonuclease to cleave the product fragments near each end, creating a 405 base pair fragments having blunt ends, as described in Example 6 and shown in FIG. 17. Thus, any products which separate from the main product peak when the MIPC separation is conducted at 66° C. (partially denaturing conditions) would have to be PCR induced mutations and not simply the result of "overhangs". In the discussion which follows, the 405 base pair product refers to the product obtained after treatment of the 500 base pair PCR amplification product with HaeIII endonuclease.

FIG. 19 shows three PCR reaction product profiles which demonstrate the use of MIPC to optimize the yield of a desired product produced by a PCR process by analysis and evaluation of said reaction product profiles and adjusting PCR process variables to optimize the yield of the desired product as compared to a predetermined standard profile.

The product profile at the top of FIG. 19 represents a PCR process (described in Example 4) in which AmpliTaq® DNA polymerase (Perkin-Elmer Applied Biosystems, Foster City, Calif.) was used to produce a 405 base pair DNA fragment. The MIPC separation was conducted at 66° C., a temperature which is known not to denature the entire 405 base pair DNA fragment, but sufficient to cause denaturing at a site of a PCR induced mutation, i.e. a base pair mismatch. Since such locally denatured fragments containing a PCR induced mutation have a lower retention time than fragments which contain no base pair mismatch (and are therefore not denatured), the replication fidelity of the AmpliTaq® induced PCR process can be evaluated and quantitated by MIPC analysis of the reaction mixture.

In addition to the large primer dimer peak near the void volume, the top profile of FIG. 19 shows the 405 base pair homoduplex product peak at a retention time of just over 6 minutes and a broader peak having a retention time of less than 6 minutes. The lower retention time peak was obtained under DMIPC conditions known to separate PCR induced mutations from their corresponding homoduplex. This lower retention time peak is a heteroduplex PCR induced mutation. Integration of the 405 base pair peak having a retention time of just over 6 minutes compared to that of a standard of known concentration showed the 405 base pair product to contain 10 ng. The only other peaks in the reaction product profile were a primer dimer peak near the void volume and a PCR induced mutation peak having a retention time just under 6 minutes.

Having identified a large PCR induced mutation and a large primer dimer peak in the PCR reaction product profile, the profile was evaluated to determine how the reaction variables could be adjusted to improve the yield of the desired 405 base pair product. The primer dimer artifact could have no influence on product yield since the primers were present in very large excess relative to the template. Therefore, improving the fidelity of replication should cause a reduction in the amount of heteroduplex PCR induced mutation product and also cause an increase in the yield of desired 405 base pair product. Since the DNA polymerase enzyme has the greatest influence over fidelity of replications, the DNA polymerase reaction variable was adjusted. As a result of this analysis and evaluation, the PCR process cycles were then repeated after adjusting the enzyme by substituting the AmpliTaq® Polymerase with Pyrococuss furiosus (Pfu) (Stratagene, Inc., La Jolla, Calif.) as described in Examples 7 and 8. All other reaction conditions remained unchanged. Pfu is a proof reading enzyme and would, therefore, be expected to reduce base mismatches during the PCR process. DMIPC analysis of the PCR process performed in the presence of Pfu gave the middle reaction product profile of FIG. 19. Integration of the 405 base pair peak having a retention time of just over 6 minutes compared to that of a standard of known concentration showed a 350% increase in the 405 base pair product to 35 ng. This improvement was predicted as a result of the analysis and identification of products in the PCR reaction product profile and adjusting the reaction variable known to be responsible for the formation of undesired products.

A further adjustment to PCR process, described in Examples 7 and 8, was made to optimize the PCR process by using PFUTurbo™ (Stratagene, Inc., La Jolla, Calif.), a DNA polymerase having greater proof reading capability than PFU. All other reaction conditions remained unchanged. Analysis by DMIPC of the PCR process containing PFUTurbo™, furnished the reaction product profile at the bottom of FIG. 19. Integration of the 405 base pair peak having a retention time of just over 6 minutes compared to that of a standard of known concentration showed a further significant increase (265%) in the yield of the 405 base pair product to 93 ng. This improvement was predicted as a result of the analysis and identification of products in the PCR reaction product profile and adjusting the reaction variable known to be responsible for the formation of undesired products.

In another example, FIG. 20 shows three PCR reaction product profiles which demonstrate the use of MIPC to provide a means for optimizing PCR fidelity by analysis and evaluation of reaction product profiles and adjusting PCR process variables to minimize deviations from replication fidelity as compared to a predetermined standard profile.

The product profile at the top of FIG. 20 represents a PCR process (described in Examples 4 and 10) in which AmpliTaq® DNA polymerase (Perkin-Elmer Applied Biosystems, Foster City, Calif.) was used to produce a 405 base pair DNA fragment. The MIPC separation was conducted at 66° C., a temperature which is known not to denature the entire 405 base pair DNA fragment, but sufficient to cause denaturation at a site of a PCR induced mutation, i.e. a base pair mismatch. Since such locally denatured fragments containing a PCR induced mutation have a lower retention time than fragments which contain no base pair mismatch (and are therefore not denatured at 66° C.), the replication fidelity of the AmpliTaq® induced PCR process can be evaluated and quantitated by MIPC analysis of the reaction mixture.

In addition to the large primer dimer peak near the void volume, the top profile of FIG. 20 shows the 405 base pair product peak at a retention time of just over 6 minutes and a broader peak having a retention time of less than 6 minutes. The lower retention time peak was obtained under MIPC conditions known to separate PCR induced mutations from their corresponding homoduplex. This lower retention time peak is, therefore, a PCR induced mutation. Integration of the product profile shows that the PCR induced mutation is present to the extent of 62%, indicating very poor replication fidelity.

Having identified a large PCR induced mutation in the PCR reaction product profile, the profile was evaluated for a potential cause of the identified PCR induced mutation. The primer dimer artifact, is known to have no influence on replication fidelity and can be ignored. Therefore, a clear potential source of this problem must be the DNA polymerase since this reaction component has the most influence over replication fidelity. As a result of this analysis and evaluation, the PCR process cycles were then repeated after adjusting the enzyme to Pyrococuss furiosus (Pfu) (Stratagene, Inc., La Jolla, Calif.) as described in Example 7. All other reaction conditions remained unchanged. Pfu is a proof reading enzyme and would, therefore, be expected to reduce base mismatches during the PCR process. MIPC analysis of the PCR process performed in the presence of Pfu gave the middle reaction product profile of FIG. 20. Quantitation of the product profile showed a large decrease in the amount of undesired PCR induced mutation product to 25%. This improvement was predicted as a result of the analysis and identification of products in the PCR reaction product profile and adjusting the reaction variable, AmpliTaq®, known to be responsible for the formation of undesired products.

A further adjustment to the PCR process was made (described in Example 7) to optimize the PCR process by using PFUTurbo™ (Stratagene, Inc., La Jolla, Calif.), a DNA polymerase having greater proof reading capability than Pfu. All other reaction conditions remained unchanged. Analysis by MIPC of the PCR process containing PFUTurbo™, furnished the reaction product profile at the bottom of FIG. 20. Quantitation of the reaction product profile showed a further reduction in the undesired PCR induced mutation product to 18%. This improvement was predicted as a result of the analysis and identification of products in the PCR reaction product profile and adjusting the reaction variable known to be responsible for the formation of undesired products.

Figure 21:
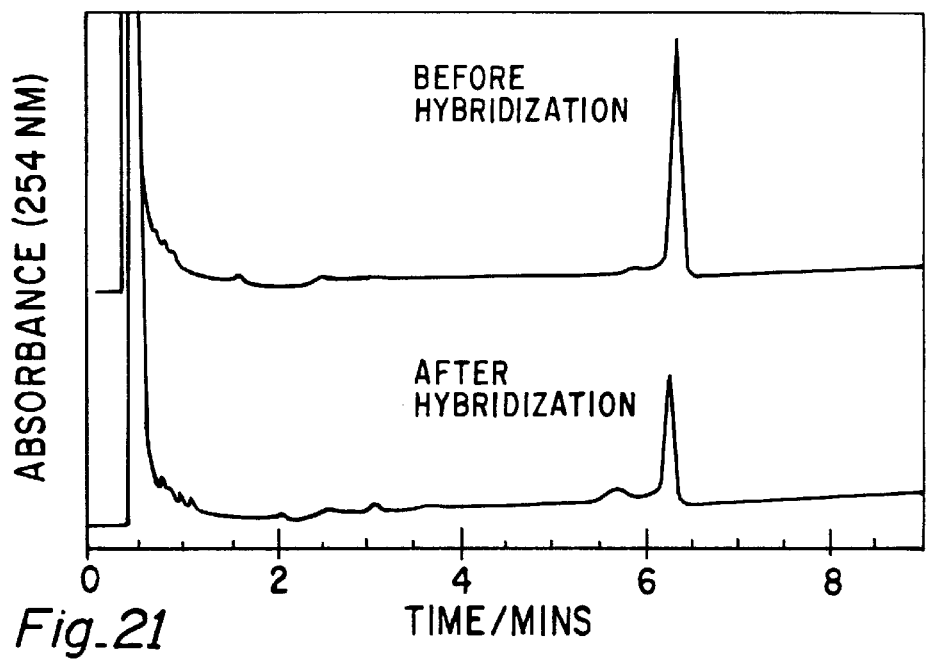
FIG. 21 shows the effect of post-PCR hybridization on the analysis results of a PCR reaction as analyzed using MIPC.

All the 405 base pair PCR reaction products discussed hereinabove were analyzed after heating the products to effect a post-process hybridization after the final PCR cycle. The final hybridization procedure is described in Example 15. A final hybridization is not normally performed after the final PCR cycle. However, Applicants have found that an inaccurate and artificially low value is obtained for PCR induced mutations without a final hybridization. This observation is demonstrated in FIG. 21. The top trace of FIG. 21 shows a chromatogram depicting the separation of a 405 base pair fragment, before post-process hybridization, by MIPC at 66° C., i.e., a temperature sufficient to cause denaturation at a site of PCR induced mutation. The heteroduplex PCR induced mutation product is seen as a small peak having a retention of just under 6 minutes. The large, sharp 405 base pair product peak is seen at a retention time of just over 6 minutes. Integration of these peaks indicates that the PCR induced mutation product was present at an 8% level.

The lower trace of FIG. 21 shows an identical MIPC separation chromatogram except that the 405 base pair product was hybridized (post-process) as described above, before separation. The lower retention time heteroduplex which represents PCR induced mutations increased to 23.1%. Therefore, the most preferred embodiment includes a post-process hybridization step in order to obtain an accurate representation of the true degree of PCR induced mutation.

Thus, using the method of the invention, a PCR process was analyzed and the products were separated by MIPC to provide a PCR reaction product profile. The separated products were identified and quantitated. As a result of this analysis and evaluation, it was possible to ascertain that a problem related to replication fidelity existed in the first examined PCR process. Thus, it was possible to predict which reaction variable could be adjusted in order to improve replication fidelity. The reaction variable most likely responsible for the observed poor replication fidelity was adjusted and the PCR process was repeated using the adjusted conditions. The degree of PCR replication fidelity improved as predicted. Furthermore, the degree of improvement was quantitated by integration of the reaction product profiles using MIPC.

Having predicted and demonstrated the improvement in the PCR process, the process was further optimized by again adjusting the previously identified reaction variable. Essentially all workers skilled in the mutation detection art have heretofore assumed near perfect PCR replication and have not considered that observed mutations in the sample might actually be PCR induced mutations and not mutations endogenous to the sample. The occurrence of PCR induced mutations as a problem common to all prior art PCR applications, especially in the area of mutation detection, has been virtually completely unrecognized, but can now be readily measured using the method of the present invention.

Figure 22:
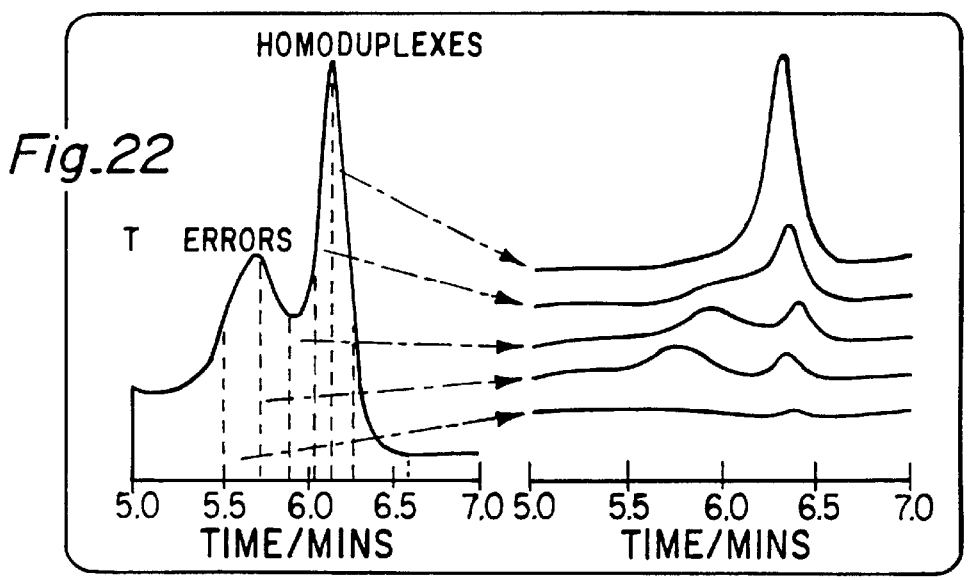
FIG. 22 shows the use of MIPC to collect a pure PCR product.

In another aspect of the invention, as described in Example 11 and shown in FIG. 22, the desired PCR product was separated from reaction impurities by MIPC and isolated as it eluted from the MIPC column. Analysis of the collected fractions by MIPC at 68° C. showed that the heteroduplex product(s) were separated in the early fractions and that pure 405 base pair homoduplex product was isolated in the last fraction. A rapid separation of heteroduplex and homoduplex along with the isolation of the latter as described herein, has not been previously reported.

A pure homoduplex fragment, separated and isolated by the method of this invention can be used in a variety of ways. Non-limiting examples of these uses include the use of a relatively large amount of pure fragment as a template in a PCR process. The purity and relatively large amount of such a template in a PCR process would yield a large amount of pure amplified product. Alternatively, a pure fragment could be incorporated into a plasmid and reproduced in a cell. Because of its high initial purity, large amounts of the fragment would be reproduced and isolated from the reproduced plasmids at a very high level of purity since little to no undesired fragments would be present and available for reproduction in the cell. Highly purified PCR products are of great value to the scientific community. Some examples of where the availability of high purity PCR products are important, include, but are not limited to, sequencing studies, cloning, production of additional quantities of an amplified polynucleotide by PCR, production of polynucleotide standards.

The ability to detect mutations in double stranded polynucleotides, and especially in DNA fragments, is of great importance in medicine, as well as in the physical and social sciences. The Human Genome Project is providing an enormous amount of genetic information which is setting new criteria for evaluating the links between mutations and human disorders (Guyer, et al. *Proc. Natl. Acad. Sci., USA* 92:10841 (1995)). The ultimate source of disease, for example, is described by genetic code that differs from wild type (Cotton, TIG 13:43 (1997)). Understanding the genetic basis of disease can be the starting point for a cure. Similarly, determination of differences in genetic code can provide powerful and perhaps definitive insights into the study of evolution and populations (Cooper et al., Human Genet. 69:201 (1997)). Understanding these and other issues related to genetic coding is based on the ability to identify anomalies, i.e., mutations, in a DNA fragment relative to the wild type. A need exists, therefore, for a methodology to detect mutations in an accurate, reproducible and reliable manner.

The discussion to follow will refer to DNA fragments for the sake of simplicity. However, it is to be understood that the discussion applies to all double stranded polynucleotides.

The "melting temperature" is defined herein to mean the temperature at which 50% of the base pairs in a DNA fragment have separated.

A "homoduplex" is defined herein to mean, a double stranded DNA fragment wherein the bases in each strand are complementary relative to their counterpart bases in the other strand.

A "heteroduplex" is defined herein to mean a double stranded DNA fragment wherein at least one base in each strand is not complementary to at least one counterpart base in the other strand. Since at least one base pair in a heteroduplex is not complementary, it takes less energy to separate the bases at that site compared to its fully complementary base pair analog in a homoduplex. This results in the lower melting temperature at the site of a mismatched base of a hetroduplex compared to a homoduplex.

The term "hybridization" refers to a process of heating and cooling a dsDNA sample, e.g., heating to 95° C. followed by slow cooling. The heating process causes the DNA strands to denature. Upon cooling, the strands re-combine into duplexes in a statistical fashion. If the sample contains a mixture of wild type and mutant DNA, then hybridization will form a mixture of hetero- and homoduplexes.

The "heteromutant site separation temperature" T(hsst) is defined herein to mean the temperature which will selectively denature the heteroduplex DNA at a site of mutation. This is a temperature which is optimal to effect a chromatographic separation of heteroduplexes and homoduplexes by MIPC and hence, detect mutations.

The term "Matched Ion Polynucleotide Chromatography" as used herein is defined as a process for separating single and double stranded polynucleotides using non-polar separation media, wherein the process uses a counterion agent, and an organic solvent to release the polynucleotides from the separation media. MIPC separations can be completed in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns. Mutation detection at the temperature required for partial denaturation (melting) of the DNA at the site of mutation can therefore be easily performed. The system used for MIPC separations is rugged and provides reproducible results. It is computer controlled and the entire analysis of multiple samples can be automated. The system offers automated sample injection, data collection, choice of predetermined eluting solvent composition based on the size of the fragments to be separated, and column temperature selection based on the base pair sequence of the fragments being analyzed. The separated mixture components can be displayed either in a gel format as a linear array of bands or as an array of peaks. The display can be stored in a computer storage device. The display can be expanded and the detection threshold can be adjusted to optimize the product profile display. The reaction profile can be displayed in real time or retrieved from the storage device for display at a later time. A mutation separation profile, a genotyping profile, or any other chromatographic separation profile display can be viewed on a video display screen or as hard copy printed by a printer.

Depending on the conditions, MIPC separates double stranded polynucleotides by size or by base pair sequence and is therefore a preferred separation technology for detecting the presence of particular fragments of DNA and RNA of interest. A separation system for mutation detection having the convenience, automation, sensitivity, and range of capabilities of MIPC has not been previously described.

When mixtures of DNA fragments are applied to an MIPC column, they are separated by size, the smaller fragments eluting from the column first. However, when MIPC is performed at an elevated temperature which is sufficient to denature that portion of a DNA fragment domain which contains a heteromutant site, then heteroduplexes separate from homoduplexes. MIPC, when performed at a temperature which is sufficient to partially denature a heteroduplex, is referred to as "Denaturing Matched Ion Polynucleotide Chromatography" (DMIPC).

The term "heteromutant" is defined herein to mean a DNA fragment containing a polymorphism or non-complementary base pair.

The term "mutation separation temperature range" is defined herein to mean the temperature range between the highest temperature at which a DNA segment is completely non-denatured and the lowest temperature at which a DNA segment is completely denatured.

The term "mutation separation profile" is defined herein to mean a DMIPC separation chromatogram which shows the separation of heteroduplexes from homoduplexes. Such separation profiles are characteristic of samples which contain mutations or polymorphisms and have been hybridized prior to being separated by DMIPC. The DMIPC separation chromatograms shown in FIG. 24 which were performed at 51° C. to 61° C. exemplify mutation separation profiles as defined herein.

The term "temperature titration" of DNA as used herein is an experimental procedure in which the retention-time from DMIPC is plotted as the ordinate against column temperature as the abscissa.

Figure 23:
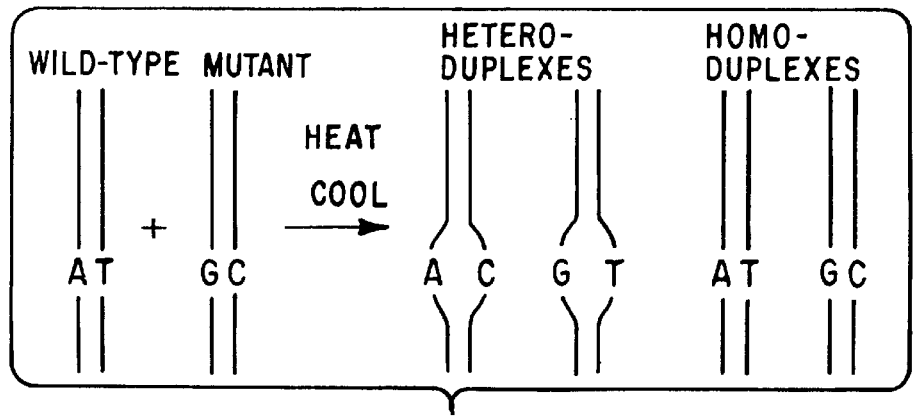
FIG. 23 shows a schematic representation of a hybridization to form homoduplex and heteroduplex.

A reliable way to detect mutations is by hybridization of the putative mutant strand in a sample with the wild type strand (Lerman, et al., Meth. Enzymol., 155:482 (1987)). If a mutant strand is present, then two homoduplexes and two heteroduplexes will be formed as a result of the hybridization process, as shown in FIG. 23. Hence separation of heteroduplexes from homoduplexes provides a direct method of confirming the presence or absence of mutant DNA segments in a sample.

Current gel electrophoresis mutation detection methods depend on the difference in melting temperature between a heteroduplex and a homoduplex. DNA separation methods separate DNA fragments based on the number of base pairs when the separations are performed below the denaturing (melting) temperature of the mismatched base pair in a heteroduplex. However, DNA fragments of the same number of base pairs can be separated when the separations are performed at the T(hsst). Such separations have been accomplished by denaturing gradient gel electrophoresis or denaturing gradient capillary electrophoresis. However, these techniques are operationally difficult to perform, are time-consuming, require a great deal of expertise and are not always reproducible. For example, denaturing gradient capillary electrophoresis analysis takes at least 30 minutes per run plus setup time. A denaturing gradient gel electrophoresis analysis takes several hours plus setup time. The fact that electrophoretic mobility decreases exponentially with the length of the denatured portion of the DNA fragment further exacerbates the problem of long analysis time inherent in electrophoretic separations. These analytical methods are not useful for routine analysis of PCR products where quick setup, ease of use, high throughput, high reproducibility, and quantitative results are necessary. An advantage of the present invention is the ability to automate the determination of T(hsst) by DMIPC for the purpose of mutation detection.

Recently, Matched Ion Polynucleotide Chromatography (MIPC) has been introduced as a DNA separation method. MIPC is easy to implement, provides reproducible results, and is capable of effectively separating single and double stranded polynucleotides on the basis of both size and base sequence. It is capable of separating heteroduplexes from homoduplexes which differ by even a single base. MIPC can separate mixtures of single and double stranded polynucleotides in general and DNA fragments in particular, without any of the limitations of the previously known gel based methods described above.

The temperature dependent separation of 209 base pair homoduplexes and heteroduplexes by DMIPC is shown in FIG. 24 as a series of separation chromatograms and the separation process is described in Example 16. The sample, containing a heterozygous sample of 209 base pair homoduplex fragments wherein the mutant fragments contained a single base pair deviation from the wild type, was hybridized as described in Example 15. The hybridization process created 2 homoduplexes and 2 heteroduplexes as shown schematically in FIG. 23. This mixture was separated as described in Example 16. As shown in FIG. 24, when MIPC was performed at 51° C., a single peak, representing all 4 mixture components, was seen. This result was expected since all 4 components have the same base pair length and the separation was performed at non-denaturing conditions, i.e., at a temperature too low to cause any denaturing. At 53° C. a shoulder appeared on the low retention time side of the main peak. This indicated the beginning of melting as well the potential presence and the partial separation of a heteroduplex. As the temperature of the separation was increased incrementally, the original single peak was eventually separated into 4 clearly defined peaks. The 2 lower retention time peaks representing the 2 heteroduplexes and the 2 higher retention time peaks representing the 2 homoduplexes are shown in FIG. 24. The 2 homoduplexes separate because the A-T base pair denatures at a lower temperature than the C-G base pair. Without wishing to be bound by theory, the results are consistent with a greater degree of denaturation in one duplex and/or a difference in the polarity of one partially denatured heteroduplex compared to the other, resulting in a difference in retention time on the MIPC column. A temperature titration of the homoduplex and heteroduplex species from the elution profiles of FIG. 24 is shown FIG. 25.

As seen in FIG. 24, the temperature range of 57° to 58° C. was optimal for this separation. The appearance of four distinct peaks was observed when a mutation was present in the original sample, in agreement with the expected results, based on the hybridization schematic in FIG. 23. Above that temperature the double stranded fragments are completely denatured, rather than being denatured only at the site of base pair mismatch. This is evidenced by the single peak, representing 4 single polynucleotide strands, seen at low retention time when the separation was carried out at 59° C. and above.

In some mutation analyses, only two peaks or a partially resolved peak(s) are observed in DMIPC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

If a sample contained homozygous DNA fragments of the same length, then hybridization and analysis by MIPC would only produce a single peak at any temperature since no heteroduplexes could be formed. In the operation of the present method, the determination of a mutation can be made by hybridizing the homozygous sample with the known wild type fragment and performing a DMIPC analysis at a partially denaturing temperature. If the sample contained only wild type fragments then a single peak would be seen in the DMIPC analysis since no heteroduplexes could be formed. If the sample contained homozygous mutant fragments, then analysis by DMIPC would show the separation of homoduplexes and heteroduplexes as seen in FIG. 24.

The temperature at which 50% of a constant melting domain is denatured may also be determined experimentally by plotting the UV absorbance of a DNA sample against temperature. The absorbance increases with temperature and the resulting plot is called a melting profile (Breslauer et al., *Proc. Natl. Acad. Sci. USA* 83:3746 (1986); Breslauer, *Calculating Thermodynamic Data for Transitions of any Molecularity*, p. 221, Marky et al. eds., J. Wiley and Sons (1987)). The midpoint of the absorbance axis on the melting profile represents the melting temperature (Tm), i.e. the temperature at which 50% of the DNA strands in the duplex are denatured. In one embodiment of the present invention, this observed Tm is used as a starting temperature for performing DMIPC for mutation detection.

In another embodiment of the present invention, software such as MELT (Lerman, et al., *Meth. Enzymol.* 155:482 (1987)) or WinMelt™, version 2.0, is used to obtain a calculated Tm which is used as a starting temperature for performing DMIPC for mutation detection. These software programs show that despite individual differences in base pair stability, the melting temperature of nearby base pairs is closely coupled, i.e., there is a cooperative effect. Thus, there are long regions of 30 to 300 base pairs, called "domains", in which the melting temperature is fairly constant. In a similar manner, the software MELTSCAN (Brossette, et al., *Nucleic Acid Res.* 22:4321 (1994)) calculates melting domains in a DNA fragment and their corresponding melting temperatures. The concept of a constant temperature melting domain is important since it makes possible the detection of a mutation in any portion of the domain at a single heteromutant site selective temperature.

The use of software packages to identify a starting temperature for performing DMIPC in connection with mutation detection has not heretofore been described and is an important aspect of the present invention. Prior to the present invention, time consuming methods development procedures were required to determine the starting temperature for mutation detection analysis. Applicants have found, however, that the calculated melting temperature, though useful for mutation detection using gel electrophoresis, must be adjusted when applied to mutation detection by DMIPC.

Applicants have developed a formula for determining the heteromutant site separation temperature T(hsst). In general, this formula is expressed by the equation $T(hsst) = X + m \cdot T(w)$, wherein T(hsst) is the heteromutant site separation temperature and where X is the DMIPC detection factor, and m is a weighting factor; both factors are used to adjust T(w) to the T(hsst). X can have a positive or negative value. In a particular embodiment of the invention, T(w) is the melting temperature determined from a UV melting profile of the normal (i.e. wild type) DNA duplex. In another particular embodiment of the invention, T(w) is calculated by software. The values of m are preferably between 0 and 2. Since X depends on the sequence of the fragment to be analyzed, its value can vary by up to about 10° C.

In another embodiment of the invention, T(hsst) is refined experimentally from the calculated melting temperature as described in the Examples, wherein a DMIPC analysis is initiated at the melting temperature calculated by software (Example 17) or determined from a melting profile of UV absorbance vs. temperature (Example 18). Subsequent samples are then injected and analyzed at incrementally lower and higher temperatures until an optimum separation is achieved. In a preferred embodiment of the invention, all aspects of the analysis are automated and the temperature increments are selected, e.g. 2° C. increments.

Applicants have surprisingly discovered that in most cases the T(hsst) is generally only 1–20° C. lower than the melting temperature as determined from a UV absorbance vs. temperature melting curve, or as determined from a temperature titration curve. After the temperature titration curve is formed, the T(hsst) can usually be determined in just 1 or 2 runs. Furthermore, Applicants have discovered that the mutation separation temperature range for DNA fragments of about 200–400 bp over which denaturation occurs is about 5° C. Therefore, even if the procedure described hereinabove only approached the T(hsst), it would be obvious in which direction to alter the temperature to achieve an optimum separation. In one embodiment, the increments are set at about 0.3°–0.5° C. In a preferred embodiment, the increments are set at 0.1° C. allowing a very accurate determination of T(hsst).

The foregoing discussion has primarily been concerned with DNA fragments having a size of about 200–400 bp. In some cases, it is more convenient to directly screen a long fragment, e.g., an exon, of up to 1.5 kb for mutations. Such long fragments generally contain multiple melting temperature domains. Double-stranded DNA fragments melt in a series of discontinuous steps as different regions with differing thermal stabilities denature in response to increasing temperature. These different regions of thermal stability are referred to as "domains", and each domain is approximately 50–300 bp in length. Each domain has its own respective Tm and will exhibit thermodynamic behavior which is related to its respective Tm. The presence of a base mismatch within a domain will destabilize it, resulting in a decrease in the Tm of that domain in the heteroduplex relative to its fully hydrogen-bonded counterpart found in the homoduplex. Generally, as discovered by Applicants, the presence of a base mismatch will lower the Tm by approximately 1–2° C. FIG. 26 depicts in schematic form the melting of a theoretical three domain fragment.

As described above, every DNA fragment is comprised of one or more regions of independent thermal stability or domains. The Tm of a domain serves as a thermodynamic signature and determines the thermodynamic behavior of a domain. As depicted in the schematic in FIG. 26, as the temperature is gradually increased, domain A will denature first because its Tm is lower than that of domain B or C. Domain B has an intermediate Tm and would melt next, and domain C would be the last to melt because its domain has the highest Tm within this fragment.

Rather than gradually "unzippering" from one end to the other, the base pairs within a domain melt in unison over a very narrow temperature range. The denaturing of a domain is characterized by a sigmoidal profile (FIG. 27) which indicates "cooperativity" among the base-pairs comprising the domain. The midpoint of the absorbance range is the Tm and corresponds to a temperature at which the domain exists in equilibrium between single and double stranded states. As the temperature is increased beyond the Tm, the entire domain will rapidly convert to a completely single-stranded conformation.

In the three domain molecule illustrated in FIG. 26, a putative point mutation could be present in any of the domains: A, B or C. In order to establish a high probability of detecting polymorphic mutations or mutations in previously uncharacterized DNA fragments, it is necessary to carefully select one or more temperatures at which fragment analysis will be performed by DMIPC.

The DMIPC system is capable of automatically profiling the melting behavior of a DNA fragment by running a series of separations at incremental temperature increases over the entire likely denaturation range (e.g. 50°–70° C.).

Figure 27:
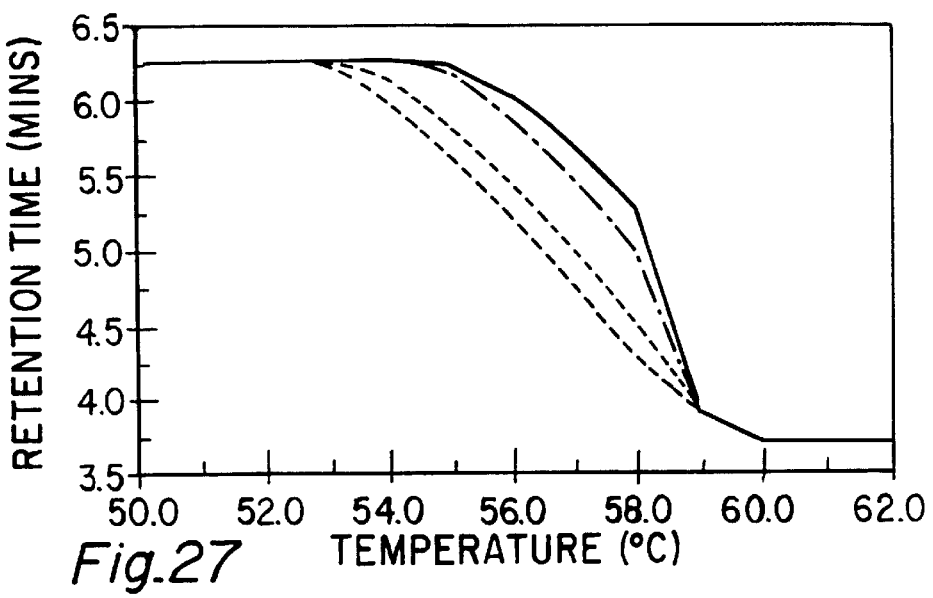
FIG. 27 shows a temperature titration of two homoduplexes (upper two curves) and two heteroduplexes (lower two curves).

FIG. 27 depicts the melting of the four related homo- and heteroduplex forms of a DNA fragment (the homoduplexes are represented by dashed lines). These melting profiles illustrate how the midpoints of the heteroduplex inflections are shifted to the left, indicating lower Tms and more rapid elution from the DMIPC column compared to the homoduplexes. It is also apparent that the Tms of the heteroduplexes are approximately 1°–2° C. lower than the homoduplexes.

Figure 28:
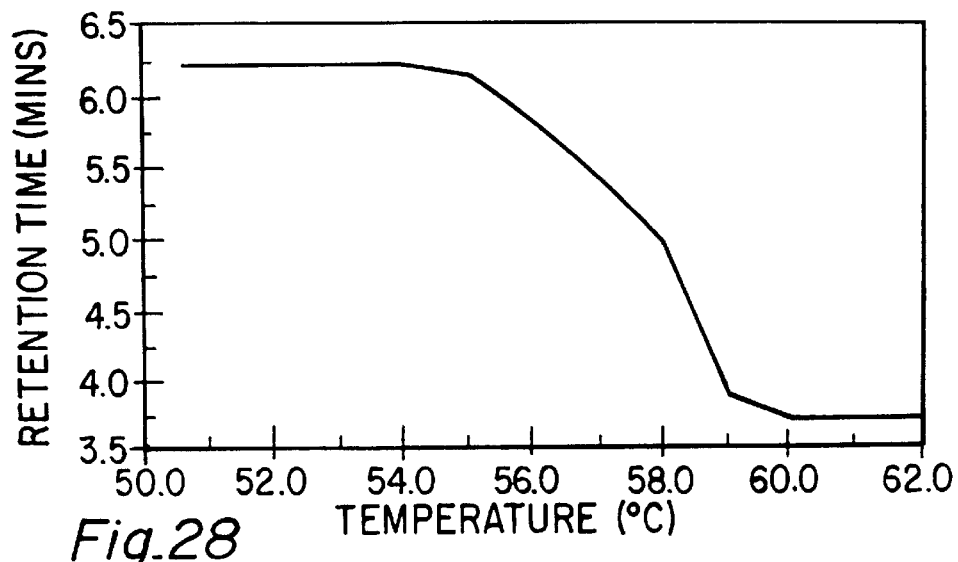
FIG. 28 shows the temperature titration for DNA fragment sY81.

FIG. 28 depicts the melting profile of 230 bp restriction fragment designated sY81. Any domains present in this fragment are now represented by a single sigmoidal curve extending between approximately 540–590° C. The temperature at this midpoint of the inflection is the Tm of the melting profile of the homoduplex fragment or $Tm_{homo}$. Determining the $Tm_{homo}$ from the melting profile is necessary for selecting an appropriate temperature at which to carry out mutation screening. Since the presence of a base mismatch will lower the Tm of the corresponding heteroduplex domain being scrutinized by approximately 1°–2° C., a fairly accurate estimation can be made of the Tm of the respective heteroduplex fragment, $Tm_{hetero}$, where $Tm_{hetero}=Tm_{homo}-1°$ C. This equation is an example of the general equation for T(hsst) described hereinabove and in which T(w) has a value of 1° C.

As indicated above, the appearance of the melting profile indicates that the $Tm_{homo}$ is approximately 56° C. Therefore, the ideal temperature for screening for mutations within this fragment would be $Tm_{hetero}=Tm_{homo}-1°$ C. or 55°. However, given the steepness of the slope created by the inflections for both domains and the closeness of the two domains' Tms, we also know that any domains present in this fragment will be partially denatured at that temperature, In the case where the Tms of two different domains are within 5° C. of one another, it is possible to screen for mutations in both domains simultaneously by selecting a single analysis temperature. However, the temperature selected must be less than or equal to the Tm of that domain which has the lower Tm. If an intermediate temperature is selected, the lower Tm domain in both the heteroduplex and homoduplex fragments will be denatured and the ability to detect mutations in that domain will be lost. If the DNA fragment melts over a temperature range greater than 5° C., more than one temperature must be used to screen the fragment.

Figure 29:
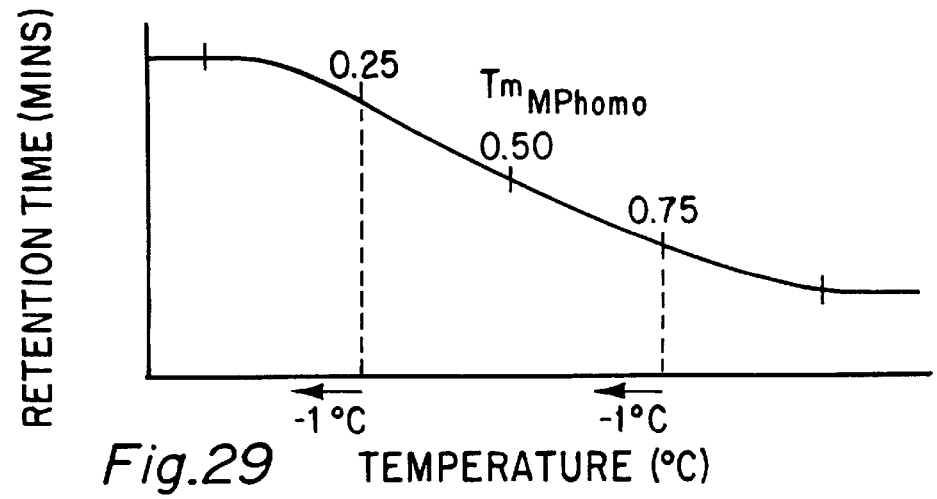
FIG. 29 shows a theoretical temperature titration of a three domain DNA fragment in which the domains have melting temperatures of 55° C., 60° C. and 65° C., respectively.

For example, if a DNA fragment contains three domains A, B and C with Tms of 55° C., 60° C., and 65° C., respectively, the slope of the melting profile will extend over a 10° C. range and be broader than the profile depicted in FIG. 28. This indicates that more than one screening temperature will have to be used to comprehensively screen all of the domains within this fragment for the presence of mutations. Domains A and B can be simultaneously screened at a temperature of 54° C. and domains B and C can be simultaneously screened at 59° C. However, there is no single temperature which will allow all three domains to be screened simultaneously. FIG. 29 depicts a theoretical melting profile for a three domain fragment with Tms of 55° C., 60° C. and 65° C.

In a particular embodiment of the present invention, when a melting profile which extends over a temperature range greater than about 5° C.–7° C., the following steps can be used to carry out comprehensive mutation screening, as shown in FIG. 29.

1. Divide the melting curve, which includes the inflection, into quarters.
2. Subtract 1° C. from temperatures at positions 0.25 and 0.75.
3. Carry out the first analysis at a temperature corresponding to position 0.25 less 1° C.
4. Carry out the second analysis at a temperature corresponding to the 0.75 position less 1° C.

As indicated hereinabove, all other parameters being constant, the melting of DNA causes the retention time on a liquid chromatography column to decrease as the temperature of the separation is increased.

In one embodiment of the present invention, a sample containing the mutation is examined at a series of temperatures using a heuristic optimization approach. The optimum temperature obtained by this procedure is the temperature at which the mutant DNA fragment is most easily distinguished from the wild-type DNA by the difference in the pattern of peaks. This approach is not systematic and relies on the knowledge on whether a heteroduplex is present in the sample. However, prior knowledge of a mismatch is not always available.

A preferred embodiment of the present invention is a method for selection of the T(hsst) is based on the temperature titration. This temperature titration can be obtained by experimental observation or obtained from a theoretical analysis of thermodynamic information. Furthermore, it has been discovered by Applicants that the optimum temperature for mutation detection corresponds to the early stages of denaturation of the segment of the wild type DNA fragment containing the mutation. A plot of retention time vs. temperature shows a parallel relationship between wild type and heteroduplex such that the retention time of both fragments is decreasing with about the same slope. This surprising and consistent relationship discovered by Applicants essentially eliminates the necessity of collecting data on the heteropduplex sample in order to select T(hsst). Instead the melting characteristics of the wild-type fragment can be used to determine T(hsst). This relationship is illustrated in the temperature titration of Example 19, in which both homoduplexes and heteroduplexes in a mixture obtained from a 209 bp DYS217 mutation, gave a slope of about −0.9 min/°C.

Figure 30:
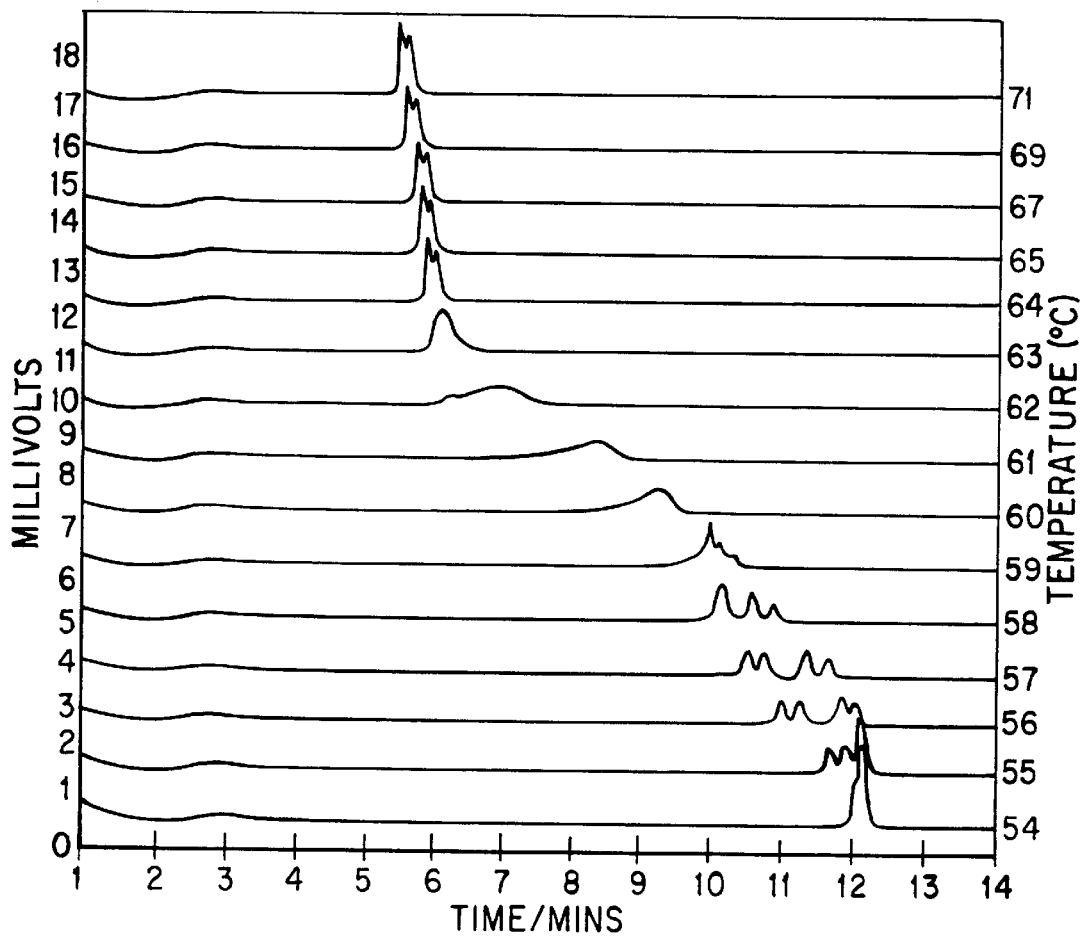
FIG. 30 shows the effect of column temperature on separation of homoduplex and heteroduplex DNA for DYS271 209 bp mutation mixture with a heteroduplex mismatch at position 168.

FIG. 30, a temperature titration for a DYS271 209 bp mutation standard mixture with a heteroduplex mismatch at the 168 bp position, shows how temperature titration information may be obtained experimentally. The data show that the 2 heteroduplex and 2 homoduplex peaks from a mismatch are well resolved at 56° C. As the temperature is increased, they become broad peaks (60° C.–63° C.) and then as the temperature is further increased the peaks merge into single stranded DNA. Since under these conditions, single stranded DNA is separated under sequence as well as size parameters, the peak is split. It is possible to miss this region if the separation is optimized for the mutation at 168 bp because elution conditions for rapid separation would cause the single stranded (melted) peaks to be merged into the first part of the gradient.

Figures 31, 32, 33:
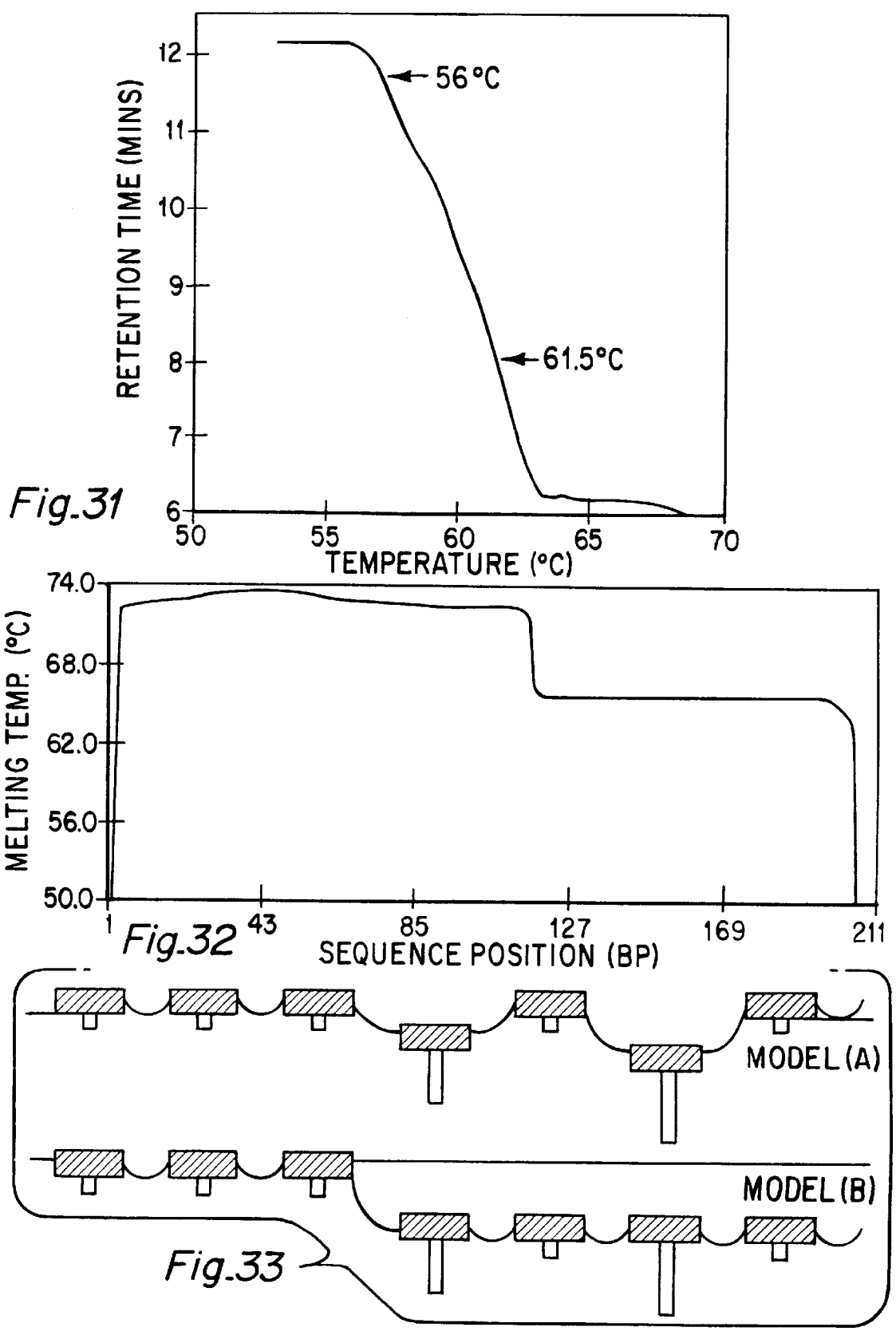
FIG. 31 shows a temperature titration for the wild type homoduplex from FIG. 30 with the inflection points indicated by arrows.
FIG. 32 is a DNA melting map of the DYS271 209 bp mutation mixture.
FIG. 33 is a schematic representation of a cooperative approach (Model A) and a non-cooperative approach (Model B) to modeling DNA melting within a fragment.

In an example of a preferred method for determining the T(hsst), FIG. 31 is a temperature titration for the latest eluting wild type homoduplex from the data of FIG. 30. The plot shows two inflection points. The first is at 56° C. and it is notable that this is the temperature where the two heteroduplex peaks and the two homoduplex peaks are well resolved as seen in FIG. 30. The retention times for the two wild type homoduplex peaks track the two heteroduplex peaks with a slope of approximately −0.9 minutes/°C. In FIG. 31 there is a second inflection point at 61.5° C. indicating that there is a high melting region within the fragment, but the mismatch is not in this high melting region.

In a preferred embodiment of the invention, the T(hsst) is selected from the temperature titration graph of the wild type homoduplex by first determining a range of temperature in which retention time is decreasing by about 0.9min/°C., and second, obtaining the inflection point on the temperature titration plot within that region and subtracting 1° C.

In another preferred embodiment of the invention, the T(hsst) is selected to correspond with a point in which the melting of the homoduplex is 25% complete. Generally, one would run DMIPC of the actual hybridized sample at three different temperatures, e.g., about 2° C. on either side of the T(hsst) as well as the predicted T(hsst). The observation of either the appearance of two inflection points, as shown in FIG. 31, or a temperature titration curve in which the 0–100% melting range is greater than about 5° C., requires two temperatures to perform the mutation analysis. Either of these observations would indicate that the fragment has two types of regions contained within the fragment, each requiring a different temperature. It is an important aspect of the method of the present invention, and based on the highly consistent and reproducible nature of the DMIPC method, that once the correct T(hsst) for a particular fragment is determined, the same temperature can be used for all later analyses of that fragment. In addition, a database of optimum temperatures corresponding to sequences which have been analyzed, can be assembled for the purpose of describing the necessary conditions for analysis of a particular mutation without having to go through the procedure of measuring the optimum temperature experimentally.

In another embodiment of the present invention, a thermodynamic mathematical model of the melting behavior of known fragments can be used to predict the melting behavior of new fragments without any experimental work on the sample itself. The model can be used to predict optimum temperatures for mutation detection and also to assess the suitability of the fragment to the technique. In effect, a temperature titration can be determined using the sequence information of the fragment and behavior predicted by thermodynamic data and models, and the fitting of these models to chromatography behavior.

Modeling of melting behavior of DNA is well developed in the literature. However, the published thermodynamic melting procedures must be modified before they can be fully used for temperature prediction for mutation detection.

The hydrogen bonding energies of nucleic acids can be measured. For example, information of this type is reported by Breslauer et al. (*Proc. Natl. Acad. Sci.* 83:3746 (1986)).

For short oligonucleotides, a simple melting model can be used in which neighboring bases (or pairs of bases) do not exert a long range influence beyond the boundary of the unit. For longer fragments, an intrinsic helical tendency is combined with a conditional probability such that the probability of a base being in the helical state is strongly affected by its neighbors. A recursive algorithm is required such as the Fixman-Freire implementation of Poland's model (Poland, *Biopolymers* 13:1859 (1974) and Fixman et al., *Biopolymers* 16:2693 (1977)). The parameters used in the Fixman-Freire algorithm have been optimized to predict melting behavior at equilibrium, in aqueous solution. An example of implementation of a thermodynamic approach to DNA melting is shown in FIG. 32 with a DNA melting profile of the DYS271 209 bp mutation. The program used to make this plot is a commercial program, WinMelt™, version 2, available form BioRad Laboratories (Richmond, Calif.). The plot shows that there are two melting domains. This approach is called a cooperative melting prediction since the melting of any particular base pair is influenced by its neighbors. This influence extends as far as the neighbors contain a similar GC content. The lower domain contains the heteroduplex mismatch at 168 bp. The plot correlates well with experiment data with two domains and the lower melting domain containing the mismatch.

However, WinMelt™ or any similar program cannot be used to predict the optimum temperature for performing mutation detection due to fact that the column, buffer and solvent can affect the melting temperature of the DNA. Since these programs use the cooperative model for melting, programs do not predict well the "temperature titrations" observed in DMIPC separations of DNA without selecting the coefficients and offsets that have been correlated with the DMIPC performance. In one embodiment, the noncooperative thermodynamic approach to modeling of DNA melting can be used. However, the preferred thermodynamic model is based on a modification of the cooperative approach.

In a preferred embodiment of the invention, a calculated melting temperature is derived using a first mathematical model such as the Fixman-Freire implementation of Poland's model. A predicted melting temperature is then derived by adjusting the calculated melting temperature according to a second mathematical model. A preferred example of a second mathematical model is an adjustment equation developed by comparing calculated temperatures based on the first model with empirically-determined temperatures observed from temperature titrations. The adjustment equation can be used to predict the T(hsst) of melting for DMPIC using only the sequence information of the wild type or homoduplex DNA. An adjustment of the Fixman-Freire calculated temperature is necessary to account for differences between the conditions used in obtaining the thermodynamic data (Breslauer et al. *Proc Natl. Acad. Sci USA* 83:3746 (1986)) and the conditions used in DMIPC.

FIG. 33 shows the difference between a cooperative approach and a noncooperative approach to DNA melting. FIG. 33 employs an analogy in which the bases in a DNA sequence are represented by pontoons (the horizontal gray rectangles) on water, and the melting temperatures are represented by ballast (the black vertical bars, with the heavier ballast represented by longer bars) with a lower melting temperature represented by a heavier ballast. In the noncooperative approach (Model A), each nucleic acid base pair in a sequence has particular stability determined by each particular hydrogen bonding energy. The stability or the melting of each base pair is independent of any surrounding base pairs. Model A shows that those base pairs that contain a high melting propensity will melt, but will not affect the melting of base pairs that have a lower propensity to melt. The cooperative approach is shown in Model B. In this case whole regions of the fragment are affect by the weighted cooperative effect of a particular region. In this model, fragments contain domains that have a propensity to melt at a particular temperature. As the temperature is increased, the different domains each at the appropriate temperature will melt.

Figure 34:
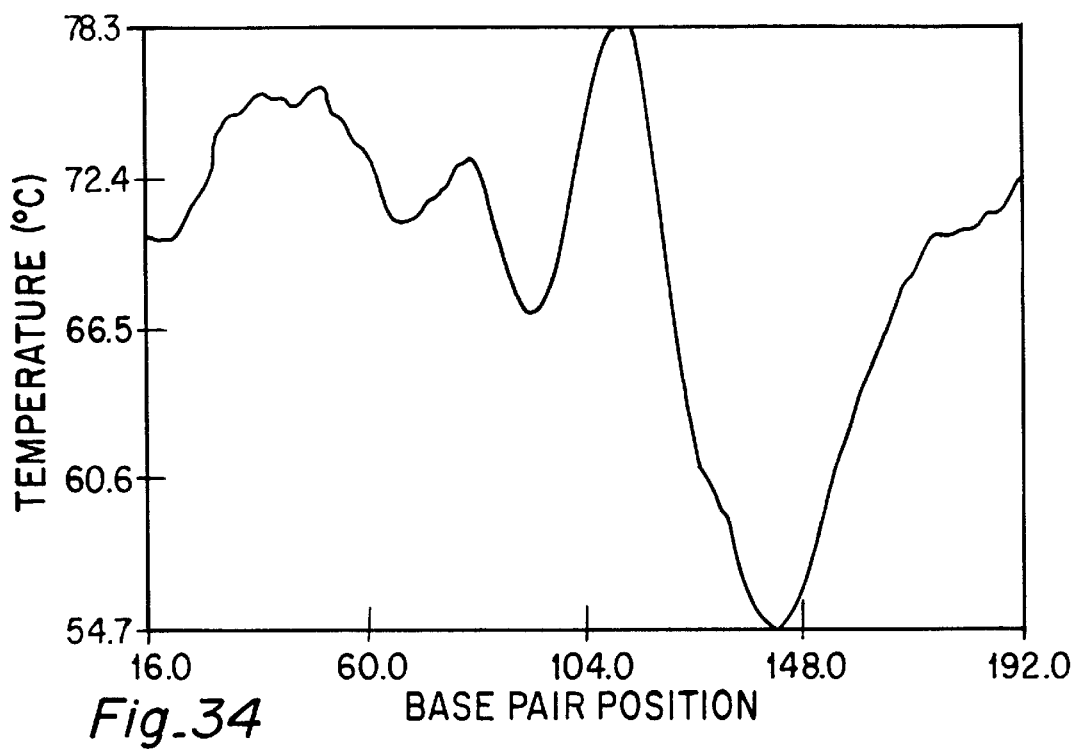
FIG. 34 shows the melting profile of the DYS271 209 bp mutation mixture using a noncooperative weighted model.
Figure 35:
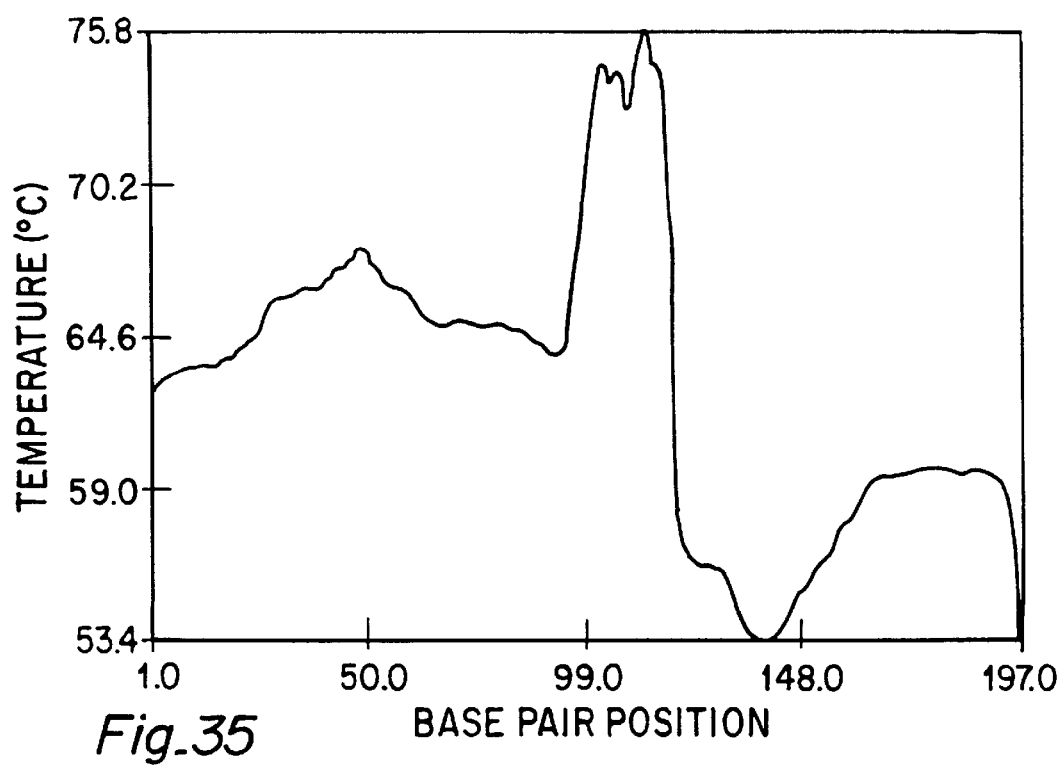
FIG. 35 shows a profile of the melting of a DYS271 209 bp mutation mixture using a cooperative model where the loop entropy has been changed to mimic a noncooperative model.

FIG. 34 shows a modified noncooperative approach to measuring the melting profile of the 209 bp mutation standard. The plot starts at base 16 and ends at base 192 because a moving weighted window of 30 bases was used to generate each point and smooth out the curve. FIG. 35 shows the same plot with the Fixman-Freire cooperative approach but where the loop entropy is $\sigma=0.01$ and the fragment is set to be 10% helical. Thus, it is possible to set parameters in a cooperative approach to mimic behavior in a noncooperative approach.

Figure 36:
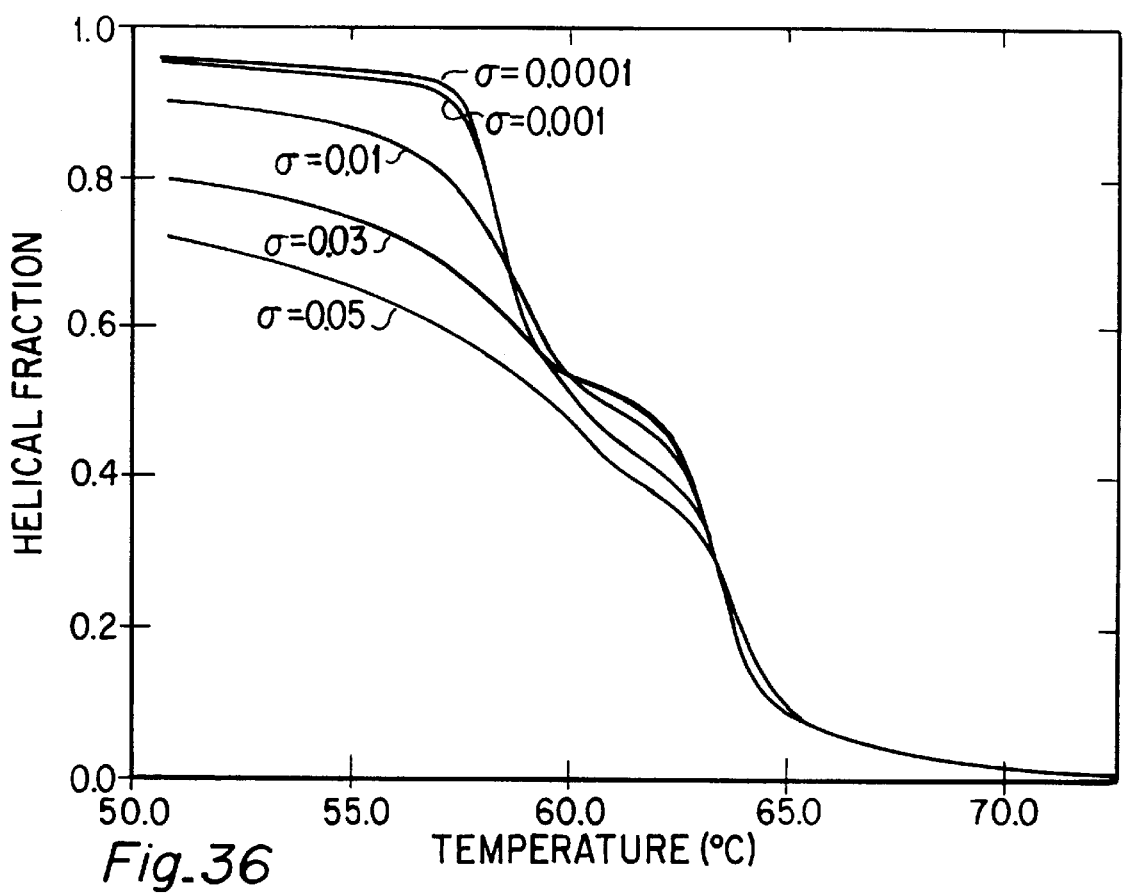
FIG. 36 shows a melting profile of DYS271 209 bp mutation mixture using a cooperative model with different loop entropies with a temperature offset, a slope, and a fragment size dependent term included.

An important feature of the present invention is to provide a method which correlates empirical temperature titrations to thermodynamic parameters. The thermodynamic parameters that relate the extent of melting to retention time are used so that the temperature titrations are modeled more accurately. A temperature offset, a slope, a fragment size dependent term, and the loop entropy and in principal even the 10 nearest neighbor free energies can be optimized. For example, the effect of loop entropy is shown in FIG. 36.

Figure 38:
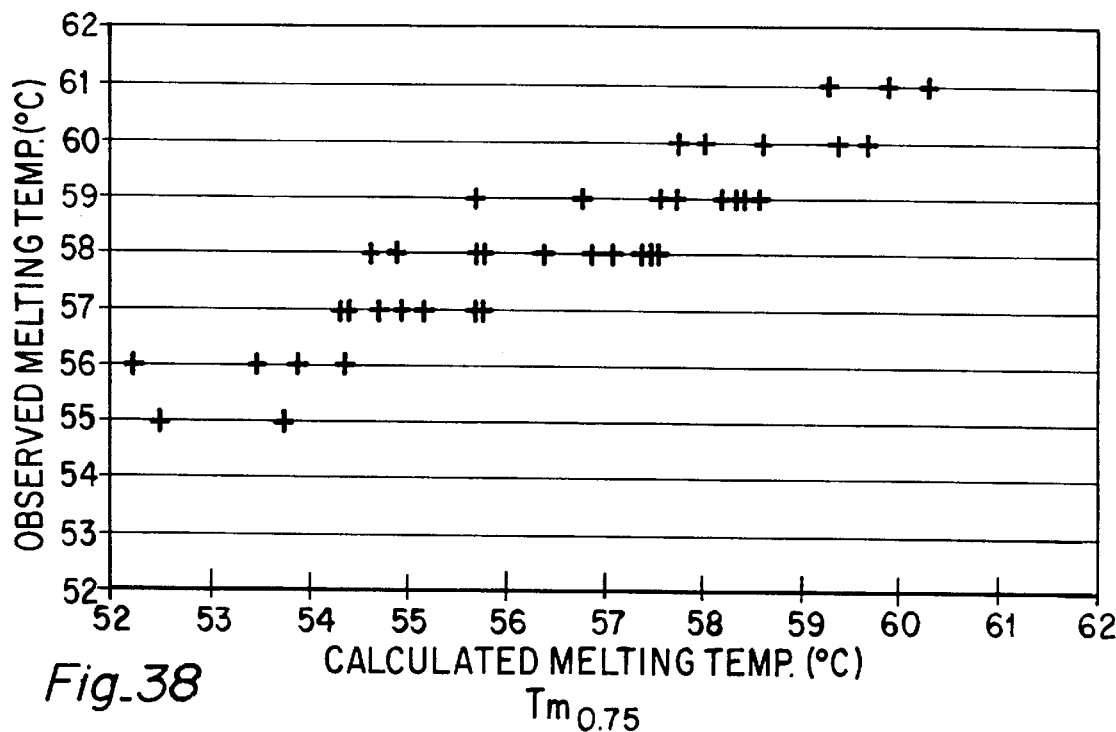
FIG. 38 is a graph of calculated melting temperature versus empirically determined melting temperature.
Figure 39:
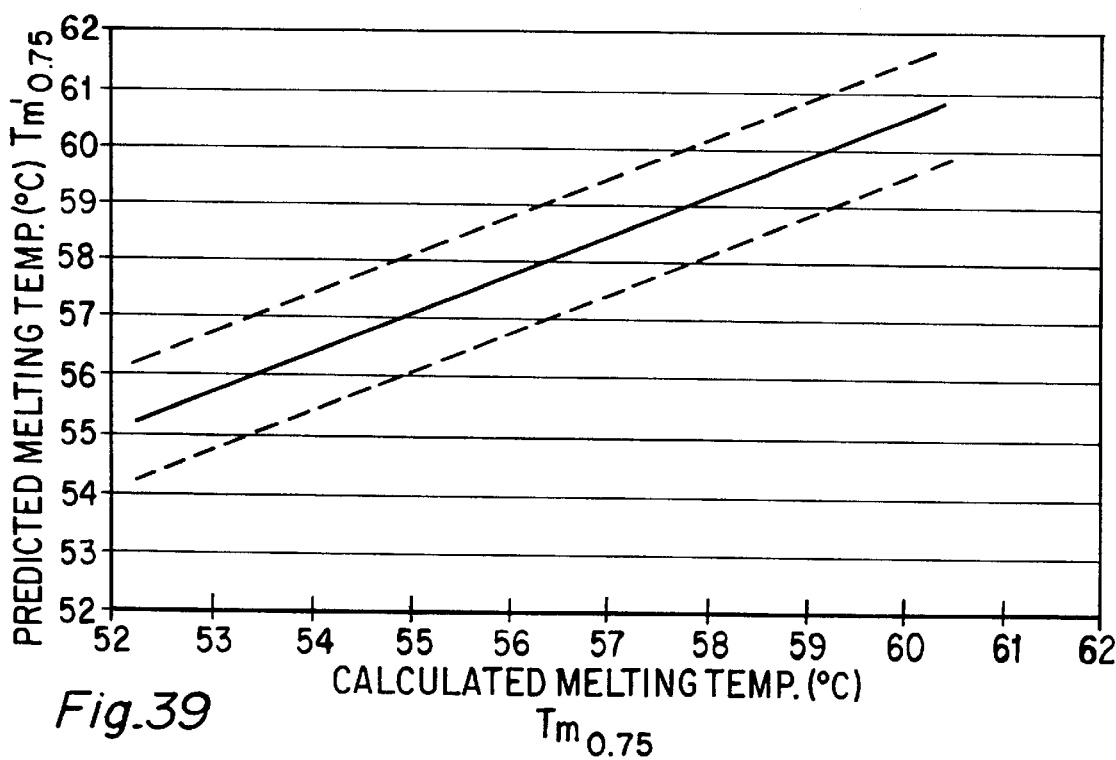
FIG. 39 is a graph of calculated melting temperature versus predicted melting temperature.

FIGS. 38 and 39 show how an adjustment equation for obtaining the predicted melting temperature can be obtained. FIG. 38 is a graph of calculated melting temperature versus empirically determined melting temperature. In FIG. 38, the abscissa represents a melting temperature corresponding to 75% helical content, $Tm_{0.75}$, i.e. a point on the melting profile where denaturation is just beginning (75% helical which is equivalent to 25% melting) calculated by the Fixman-Freire model using a loop entropy of 0.0001. The ordinate represents empirically determined melting temperatures which are preferably those previously optimized for use in high throughput screening by DMIPC for known mutations. The data plotted on the graph indicate the empirically determined melting temperatures for each of 40 experimental temperature titrations of hybridized fragments.

FIG. 39 is a graph of calculated melting temperature versus predicted melting temperature. The solid line represents a linear fit of the 40 points from FIG. 38. As indicated in FIG. 39, the line $Tm_{075}'$ is defined by the equation $$Tm_{075}'=19.6+0.68 \cdot Tm_{075}$$

Also plotted on the graph of FIG. 38 are dashed lines representing one degree above and below the line representing $Tm_{075}'$. These dashed lines indicate that the accuracy of the predicted $Tm_{075}'$ may be expected to be within about one degree of the empirically determined values.

A predicted melting temperature can be obtained by first calculating $Tm_{075}$ according to the Fixman-Freire algorithm, and then by adjusting $Tm_{075}$ according to the above equation.

Therefore, in a preferred embodiment of the invention, the equation above is used to predict a point on the melting profile where denaturation is just beginning (75% helical which is comparable to 25% melting on an experimental titration curve), where $Tm'_{0.75}$ is the predicted temperature corresponding to 75% helical content and $Tm_{0.75}$ is the temperature calculated from the Fixman-Freire algorithm using a loop entropy of 0.0001. This has improved predictive power at calculating the optimal temperature for mutation detection compared with the unmodified algorithm. As the loop entropy term is increased, the melting profiles become less dominated by domain like stepwise melting (FIG. 36). This term can therefore be optimized to model the experimental curves more accurately. The melting temperature in the above embodiment was selected at 75% helical content. Those skilled in the art will recognize that other points on the empirical temperature titration curves can be selected, e.g., 50% or 90% helical content, and calculated temperatures can be obtained and adjusted as described hereinabove. The use of thermodynamic data and equations to predict temperature titrations can be performed in many different ways. The above approach is preferred for this invention. However, since the approach is an empirical one with the calculated temperatures fitted to actual optimum temperatures for mutation detection, the use of the equations can be performed in other ways with different weighted coefficients.

The present invention provides a method for detecting mutations in a DNA sample using MIPC. Although the discussion to follow refers to DNA fragments, it is to be understood that the invention can be practiced with any double stranded polynucleotides.

In one embodiment of the invention, a mixture of homoduplexes and heteroduplexes is formed prior to the MIPC analysis. A standard polynucleotide homoduplex is added to the sample and the mixture is subjected to denaturation, e.g. by heating the mixture to about 90° C. The denatured single stranded polynucleotides formed during the denaturation process are then annealed by slowly cooling the mixture to ambient temperature. A new mixture of homoduplexes and heteroduplexes is formed if the sample contains a mutation. If the sample does not contain a mutation, only a homoduplex of the standard polynucleotide will be formed. In the preferred embodiment, the standard polynucleotide is the "wild type" polynucleotide.

It is well known in the DNA art that a heteroduplex strand will denature selectively at the site of base pair mismatch, creating a "bubble", at a lower temperature than is necessary to denature the remainder of the heteroduplex strand, i.e., those portions of the heteroduplex strand which contain complementary base pairs. This phenomenon, generally referred to as partial denaturation, occurs because the hydrogen bonds between mismatched bases are weaker than the hydrogen bonds between complementary bases. Therefore, less energy is required to denature the heteroduplex at the mutation site, hence the lower temperature required to partially denature the hetroduplex at the site of base pair mismatch than in the remainder of the strand.

Although MIPC separates DNA fragments by base pair length, homoduplex and heteroduplex fragments having the same base pair length are separated when the chromatography is conducted under partially denaturing temperature conditions, i.e., at a temperature which partially denatures a heteroduplex as described above. When MIPC is used under partially denaturing conditions to separate a mixture of homoduplexes and heteroduplexes, the heteroduplexes usually elute ahead of the homoduplexes.

An important aspect of the invention is the surprising, and heretofore unreported discovery by Applicants, that there exists a highly reproducible relationship between the concentration of organic solvent in the mobile phase required to elute DNA fragments from an MIPC column and the base pair length of the DNA fragments. Using this relationship, a "preliminary organic solvent concentration" required to elute a DNA fragment of known size can be obtained from a reference which relates the concentration of organic solvent in the mobile phase required to elute a given base pair length fragment to the base pair length of DNA fragments, obviating the need to develop methods for elution conditions. This reference is used in the invention to determine the preliminary solvent concentration. The "preliminary solvent concentration" is defined to mean the concentration of organic solvent, obtained from a reference, which is required to elute a fragment of corresponding base pair length from a MIPC column under non-denaturing conditions (about 50° C.).

The reference relating the organic solvent concentration in the mobile phase required to elute DNA fragments having different base pair lengths is represented by the graph in FIG. 40. It is to be understood that the relationship depicted in the graph in FIG. 40 can be expressed over different ranges of base pair length and solvent concentrations. The data used to generate the reference depicted in FIG. 40 can be represented as a graph or a table. The data can be used to obtain an equation of a best-fit curve. For example, the following equation gave the curve shown in FIG. 38:

$$\%B_p = 19.24 + [53.6 \cdot bp/(78.5 + bp)]$$

The reference graph, FIG. 40, was derived by Applicants as described in Example 20. Standard fragments of known base pair lengths were applied to an MIPC column and the concentration of organic solvent in the mobile phase sufficient to elute each fragment was determined when the chromatography was conducted at 50° C. The concentrations of organic solvent so determined, were plotted against their respective base pair length fragments to create FIG. 40. The standard fragments of known base pair length were obtained from a pUC18 DNA-HaeIII digest (S6293, Sigma-Aldrich). The fragments used to prepare the reference of FIG. 40 (in base pair length) were 80, 102, 174, 257, 267, 298, 434, 458, and 587. It is to be understood that the method described herein for creating the reference of FIG. 40 is only one of many other methods which can be used to construct such a reference. For example, other sets of standard fragments could be used.

The essential, and heretofore unrecognized feature of the invention on which the reference concept is based, is the discovery by Applicants that under non-denaturing conditions, DNA fragments are separated by their size and this separation is highly reproducible using MIPC. Therefore, it is not necessary to calibrate a MIPC column for each sample analysis. Daily or even weekly calibrations are usually not necessary. Once a solvent concentration has been determined for a given base pair length, the retention time of that fragment will be constant at that solvent concentration, not only from day to day on the same column, but also from one column to another. It is this surprising discovery that makes it possible to create a reference relating solvent concentration to base pair length and to predict a preliminary solvent concentration for eluting a DNA fragment of known base pair length without any additional methods development. Although good results can be obtained with default values and no calibration, preferred practice is to calibrate when a new column or eluant (buffer or mobile phase) is installed on the instrument.

An example of a procedure for pre-selection of organic solvent concentration in the mobile phase for mutation detection by MIPC is described in Example 21, and shown in FIG. 41. In one embodiment of this invention, two buffers are prepared: A first buffer, "A" containing only the counterion agent (e.g., 0.1 M TEAA) and a second buffer, "B", containing the counterion agent and organic solvent (e.g., 0.1 M TEAA, 25% acetonitrile). These buffers are mixed to achieve the desired concentration of organic solvent in the mobile phase during the separation.

To select a preliminary mobile phase organic solvent concentration for mutation detection, the %B corresponding to the base pair length fragment of interest is obtained from the reference graph of mobile phase concentration vs. base pair length (FIG. 40). Once the preliminary solvent concentration, based on the base pair length of the DNA fragments to be eluted, is obtained from the reference, a "fragment bracketing range" of organic solvent is selected. The fragment bracketing range has an initial concentration of organic solvent and a final concentration of organic solvent. The initial concentration contains an organic solvent concentration up to an amount required to elute the first eluting DNA molecule in the mixture. The final concentration contains an organic solvent concentration sufficient to elute the last eluting DNA fragment in the mixture. In a preferred embodiment, the initial solvent concentration of the pre-selected fragment bracketing range is less than or equal to about 15 percentage units below the %B of the preliminary solvent concentration. The final solvent concentration of the pre-selected fragment bracketing range is at least about 5 percentage units higher than the %B of the preliminary solvent concentration. When used in a MIPC analysis to detect mutations, the chromatography is run using a gradient based on the pre-selected fragment bracketing range. Although the procedure described above is widely applicable in practice, it will be appreciated that initial and final solvent concentrations can be adjusted for specific applications.

In a preferred embodiment, the chromatography system is controlled by a computer and is run in an automated fashion. The chromatography column is equilibrated using the initial solvent concentration. Following sample injection, the solvent concentration is increased at the rate of 2% minute over 5–15 minutes. Preferably, the gradient is run over 10 minutes to reach the final concentration of the pre-selected fragment bracketing range. The solvent concentration is then immediately increased to 100% B for 2 minutes to wash the column. The solvent concentration is then reduced to the initial solvent concentration and the column is equilibrated for two minutes in preparation for the next sample injection. This entire process is automated and the entire time span between samples, including column washing and equilibration, is less than 15 minutes.

In an other embodiment, the MIPC process described above can be optimized to increase throughput in mutation detection assays or other analyses which require screening a large number of samples. For example, once a sample has been analyzed using the preferred automated embodiment of the invention described above, the process an be optimized by adjusting the slope of the solvent gradient to effect earlier elution of heteroduplexes, so long as the separation of homoduplexes is maintained. Optionally, the solvent gradient can be programmed to ramp up to 100% for column washing immediately after the retention time of the heteroduplex is passed, without waiting for the homoduplex to appear. Following washing, the solvent concentration can be immediately ramped down to the initial concentration to equilibrate the column for the next analysis. In this manner the entire chromatography time for a sample can be reduced from about 15 minutes to less than 10 minutes, and preferably, to less than about 5–7 minutes.

The determination of the pre-selected fragment bracketing range can be represented by the formulas: $\%B_i = \%B_p - 15$, and $\%B_f = \%B_p + 5$, where $\%B_i$ is the initial percentage of buffer B in the mobile phase, $\%B_f$ is the final percentage of buffer B in the mobile phase, and $\%B_p$ is the preliminary percent B in the mobile phase as obtained form the reference.

In a preferred embodiment of the invention, the fragment bracketing range is selected automatically by software residing in the computer. In this embodiment, the user enters the base pair length of the fragment to be analyzed into a user interface screen. Software, using reference data which relates base pair length to solvent concentrations and the equation shown above, calculates the injection conditions, the initial and final solvent concentrations of the pre-selected fragment bracketing range required to effect the desired separations, and the column wash conditions.

The preferred gradient used in the MIPC mutation detection analysis is shown graphically in FIG. 41. However, both linear or nonlinear gradients which are steeper than 2% per minute, can be used to expedite the analysis as long as the homoduplex and heteroduplex fragment separation is retained. A linear or nonlinear gradient which is shallower than 2% per minute can also be used. The latter approach is useful to enhance the separation of poorly resolved homoduplex and heteroduplex peaks.

The organic solvent in the mobile phase is selected from the group consisting of methanol, ethanol, acetonitrile, ethyl acetate, and 2-propanol. The preferred organic solvent in the mobile phase is acetonitrile.

The mobile phase contains a counterion agent selected from the group consisting of lower alkyl primary, secondary, and tertiary amines, lower trialkyammonium salts and lower quaternary alkyalmmonium salts. Examples of counterion agents include, but are not limited to octylammonium acetate, decylammonium acetate, octadecylammonium acetate, pyridiniumammonium acetate, cyclohexylammonium acetate, diethylammonium acetate, propylethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde et al. in *Ion Chromatography*, $2^{nd}$ Ed., Dr. Alfred Huthig Verlag Heidelberg (1987). The preferred counterion agent is triethylammonium acetate.

For separation of polynucleotide samples, such as DNA fragments, using temperature to effect at least partial denaturation, the pH of the mobile phase is typically maintained between about 7 and 9. Preferably, the mobile phase is maintained at a pH of about 7.3.

In using the invention in its preferred embodiment to effect a separation of homoduplexes and heteroduplexes for the purpose of mutation detection, a DNA sample is hybridized with a wild type DNA fragment by denaturing and annealing the mixture as described herein above. The DNA sample can be hybridized with wild type directly. The DNA sample can also be amplified by PCR and then hybridized with wild type. Alternatively, a wild type fragment may be added to the sample prior to PCR amplification. The amplified mixture can then be hybridized following amplification. In each of these three hybridization scenarios, a mixture of homoduplexes and heteroduplexes is produced if a mutation is present in the sample. The sample, so prepared, is analyzed by MIPC under partially denaturing conditions, preferably at 56° to 58° C., for the presence of a mutation using the method of the invention for pre-selecting the preliminary organic solvent concentration and the fragment bracketing range as described hereinabove.

When the method of the invention is used for screening a large number of samples for the presence of a mutation, the throughput of samples may be increased significantly by speeding up the analysis for each sample using a steeper gradient for the fragment bracketing range.

In all embodiments and aspects of the invention, the polynucleotide fragments are detected as they are separated and eluted from the column. Any detector capable of detecting polynucleotides can be used in the MIPC mutation detection method. The preferred detector is an online UV detector. If the DNA fragments are tagged with fluorescent or radioactive tags, then a fluorescence detector or radioactivity detector can be employed, respectively. Following detection, the separated fragments are displayed on a video display screen or printed by a printer. The fragments so displayed appear either as peaks or as bands in a lane, i.e., in a virtual gel display format as described in U.S. patent application Ser. No. 09/039,061 filed Mar. 13, 1998. The choice of format is selectable by the user.

The mutation detection method of the invention can also be used to detect mutations in DNA samples when the base pair length of the fragment is unknown. Although the base pair length of such samples can be determined by the method of the invention, the presence of a mutation can only be determined if the sample is from a heterozygous source. Hybridization of a heterozygous sample will result in the formation of heteroduplexes and homoduplexes, which can be detected by DMIPC. However, a homozygous mutant will not produce heteroduplexes after hybridization. A homozygous mutant in an unknown fragment will, therefore not be detected. Since the sequence of a DNA fragment of unknown length is also unknown, hybridization with wild type to produce heteroduplexes is not possible.

In practice, the sample is applied to an MIPC column without PCR amplification. An unknown sample cannot be amplified since primers cannot be designed for an unknown sequence. However, the sample is hybridized prior to analysis in order to create a mixture of heteroduplexes and homoduplexes if the sample was from a heterozygous source.

The chromatography is conducted under non-denaturing conditions, i.e., 50° C., using a preliminary solvent concentration selected from the lowest base pair portion of the reference FIG. 40 or similar reference. Since the separation of polynucleotides by MIPC is dependent on base pair length under non-denaturing conditions, only fragments of 80 bp or less will elute using the solvent concentration corresponding to 80 bp. If no peak is eluted after about 15 minutes, the sample must contain a fragment longer than 80 bp. Therefore, the concentration of solvent in the mobile phase is increased to the concentration corresponding to the next base pair length fragment. The process of incremental increases in solvent concentration is continued until a peak is detected. The solvent concentration at which the unknown sample is eluted is adjusted to effect elution in about 10 minutes. The chromatography is then repeated under denaturing conditions (56° to 58° C.) using a fragment bracketing range of solvent concentration in a linear 2% per minute gradient as described hereinabove. The appearance of lower retention time peak(s) in addition to the homoduplex peak (s), when the sample is eluted under partially denaturing conditions, indicates that the unknown sample is heterozygous. In addition, by examining the reference of FIG. 40, the base pair length corresponding to the solvent concentration which effected elution of the unknown fragment can be determined, thereby establishing the base pair length of an unknown fragment.

Mixtures of polynucleotides in general, and double stranded DNA in particular, are effectively separated using Matched Ion Polynucleotide Chromatography (MIPC). MIPC separations of polynucleotides at non-denaturing temperature, typically less than about 50° C., are based on base pair length. However, even traces of multivalent cations anywhere in the solvent flow path can cause a significant deterioration in the resolution of the separation after multiple uses of an MIPC column. This can result in increased cost caused by the need to purchase replacement columns and increased downtime.

Therefore, effective measures to prevent multivalent metal cation contamination of the separation system components, including separation media and mobile phase contacting. These measures include, but are not limited to, washing protocols to remove traces of multivalent cations from the separation media and installation of guard cartridges containing cation capture resins, in line between the mobile phase reservoir and the MIPC column. These, and similar measures, taken to prevent system contamination with multivalent cations have resulted in extended column life and reduced analysis downtime.

Recently, MIPC has been successfully applied to the detection of mutations in double stranded DNA by separating heteroduplexes from homoduplexes. Such separations depend on the lower temperature required to denature a heteroduplex at the site of base pair mismatch compared to a fully complementary homoduplex DNA fragment. MIPC, when performed at a temperature which is sufficient to partially denature a heteroduplex is referred to herein as Denaturing Matched Ion Polynucleotide Chromatography (DMIPC). DMIPC is typically performed at a temperature between 52° C. and 70° C. The optimum temperature for performing DMIPC is 54° C. to 59° C.

The previously described precautions taken to remove multivalent metal cations were adequate for maintaining column life, as demonstrated by good separation efficiency, under non-denaturing conditions. However, Applicants have surprisingly found that when performed at partially denaturing temperature, conditions for effective DMIPC separations become more stringent. For example, a separation of a standard pUC18 HaeIII digest on a MIPC column at 50° C. provided a good separation of all the DNA fragments in the digest. However, a standard 209 bp DYS271 mutation detection mixture of homoduplexes and heteroduplexes (Transgenomic, Inc., San Jose, Calif.) applied to the same MIPC column and eluted under DMIPC conditions, i.e., 56° C., afforded a poor separation the mixture components. In order to optimize column life and maintain effective separation performance of homoduplexes from heteroduplexes at partially denaturing temperatures, as is required for mutation detection, special column washing and storage procedures are used in the embodiments of the invention as described hereinbelow.

In one aspect of this invention, therefore, an aqueous solution of multivalent cation binding agent is flowed through the column to maintain separation efficiency. In order to maintain the separation efficiency of a MIPC column at partially denaturing temperature, the column is preferably washed with multivalent cation binding agent solution after about 500 uses or when the performance starts to degrade.

Non-limiting examples of multivalent cation binding agents which can be used in the present invention are selected from the group consisting of acetylacetone, alizarin, aluminon, chloranilic acid, kojic acid, morin, rhodizonic acid, thionalide, thiourea, α-furildioxime, nioxime, salicylaldoxime, dimethylglyoxime, α-furildioxime, cupferron, α-nitroso-β-naphthol, nitroso-R-salt, diphenylthiocarbazone, diphenylcarbazone, eriochrome black T, PAN, SPADNS, glyoxal-bis(2-hydroxyanil), murexide. α-benzoinoxime, mandelic acid, anthranilic acid, ethylenediamine, glycine, triaminotriethylamine, thionalide, triethylenetetramine, EDTA, metalphthalein, arsonic acids, α,α'-bipyridine, 4-hydroxybenzothiazole, β-hydroxyquinaldine, β-hydroxyquinoline, 1,10-phenanthroline, picolinic acid, quinaldic acid, α,α', α"-terpyridyl, 9-methyl-2,3,7-trihydroxy-6-fluorone, pyrocatechol, rhodizonic acid, salicylaldoxime, salicylic acid, tiron, 4-chloro-1,2-dimercaptobenzene, dithiol, mercaptobenzothiazole, rubeanic acid, oxalic acid, sodium diethyldlthiocarbarbamate, and zinc dibenzyldithiocarbamate. These and other examples are described by Perrin in *Organic Complexing Reagents: Structure, Behavior, and Application to Inorganic Analysis,* Robert E. Krieger Publishing Co. (1964).

In a preferred embodiment the multivalent cation binding agent is water soluble. The solubility in water can be enhanced by attaching covalently bound ionic functionality, such as, sulfate, carboxylate, or hydroxy. The cation binding agent must be easily removed from the column by washing with water, organic solvent or mobile phase. The cation binding agent must not interfere with the use of the column. A preferred multivalent cation binding agent is EDTA.

The concentration of a solution of the cation binding agent can be between 0.01M and 1M. In a preferred embodiment, the column washing solution contains EDTA at a concentration of about 0.03 to 0.1M.

In another embodiment, the solution contains an organic solvent selected from the group consisting of acetonitrile, ethanol, methanol, 2-propanol, and ethyl acetate. A preferred solution contains at least 2% organic solvent to prevent microbial growth. In a most preferred embodiment a solution containing 25% acetonitrile is used to wash a MIPC column.

The multivalent cation binding solution can, optionally, contain a counterion agent. The counterion agent is selected from the group consisting of lower primary, secondary and tertiary amines, and lower trialkyammonium and quaternary ammonium salts. Examples of counterion agents include, but are not limited to octylammonium acetate, decylammonium acetate, octadecylammonium acetate, pyridiniumammonium acetate, cyclohexylammonium acetate, diethylammonium acetate, propylethylammonium acetate, butylethylammonium acetate, methylhexylammonium acetate, tetramethylammonium acetate, tetraethylammonium acetate, tetrapropylammonium acetate, tetrabutylammonium acetate, dimethydiethylammonium acetate, triethylammonium acetate, tripropylammonium acetate, tributylammonium acetate, tetraethylammonium acetate, tetrapropylammonium acetate, and tetrabutylammonium acetate. Although the anion in the above examples is acetate, other anions may also be used, including carbonate, phosphate, sulfate, nitrate, propionate, formate, chloride, and bromide, or any combination of cation and anion. These and other agents are described by Gjerde et al. in *Ion Chromatography,* $2^{nd}$ Ed., Dr. Alfred Huthig Verlag Heidelberg (1987).

In one embodiment, the MIPC separation column is washed with the multivalent cation binding solution at an elevated temperature in the range of 50° to 80° C. In a preferred embodiment the column is washed with a solution containing EDTA, TEAA, and acetonitrile, in the 70° to 80° C. temperature range. In a specific embodiment, the solution contains 0.032 M EDTA, 0.1M TEAA, and 25% acetonitrile.

Column washing can range from 30 seconds to one hour. For example, in a high throughput DMIPC assay, the column can be washed for 30 seconds after each sample, followed by equilibration with mobile phase. Since DMIPC can be automated by computer, the column washing procedure can be incorporated into the mobile phase selection program without additional operator involvement. In a preferred procedure, the column is washed with multivalent cation binding agent for 30 to 60 minutes at a flow rate preferably in the range of about 0.05 to 1.0 mL/min.

In one embodiment, a DMIPC column is tested with a standard mutation detection mixture of homoduplexes and heteroduplexes after about 1000 sample analyses. If the separation of the standard mixture has deteriorated compared to a freshly washed column, then the column can be washed for 30 to 60 minutes with the multivalent cation binding solution at a temperature above about 50° C. to restore separation performance.

In another aspect, Applicants have discovered that column separation efficiency can be preserved by storing the column separation media in the column containing a solution of multivalent cation binding agent therein. The solution of binding agent may also contain a counterion agent. Any of the multivalent cation binding agents, counterion agents, and solvents described hereinabove are suitable for the purpose of storing a MIPC column. In a preferred embodiment, a column packed with MIPC separation media is stored in an organic solvent containing a multivalent cation binding agent and a counterion agent. An example of this preferred embodiment is 0.032 M EDTA and 0.1M tetraethylammonium acetate in 25% aqueous acetonitrile. In preparation for storage, a solution of multivalent cation binding agent, as described above, is passed through the column for about 30 minutes. The column is then disconnected from the HPLC apparatus and the column ends are capped with commercially available threaded end caps made of material which does not release multivalent cations. Such end caps can be made of coated stainless steel, titanium, organic polymer or any combination thereof.

Figure 42:
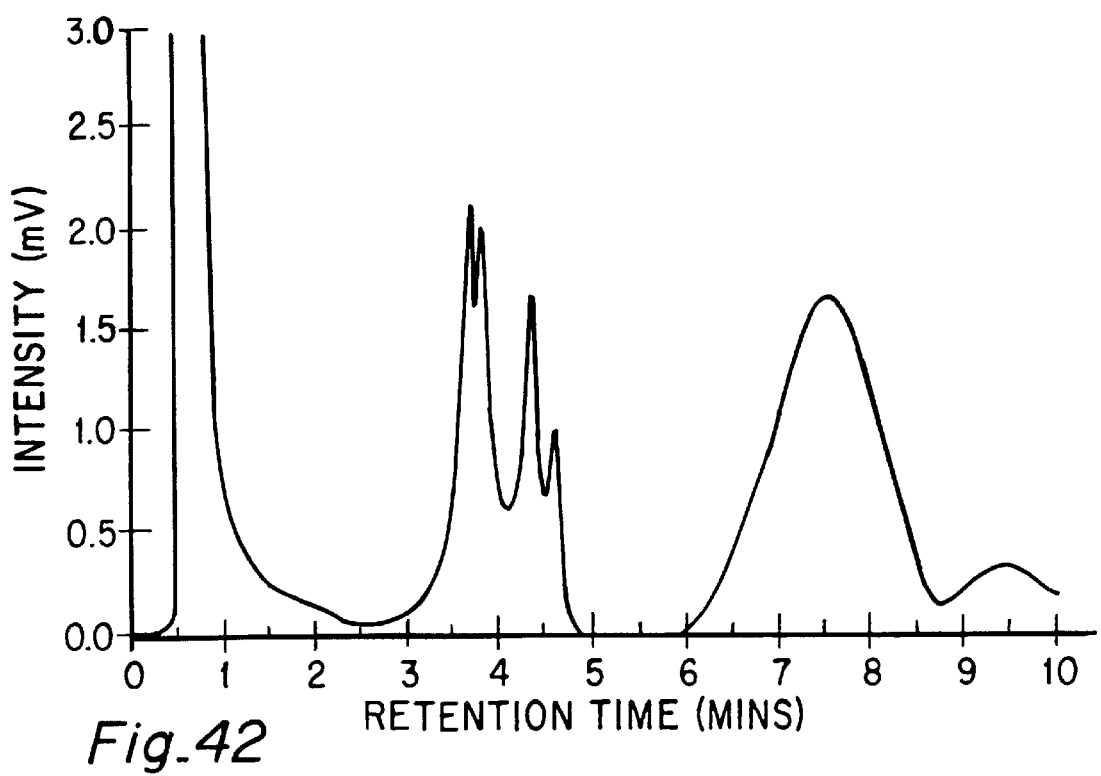
FIG. 42 is an elution profile showing separation of a 209 base pair homoduplex/heteroduplex mutation detection mixture performed by DMIPC at 56° C.
Figure 43:
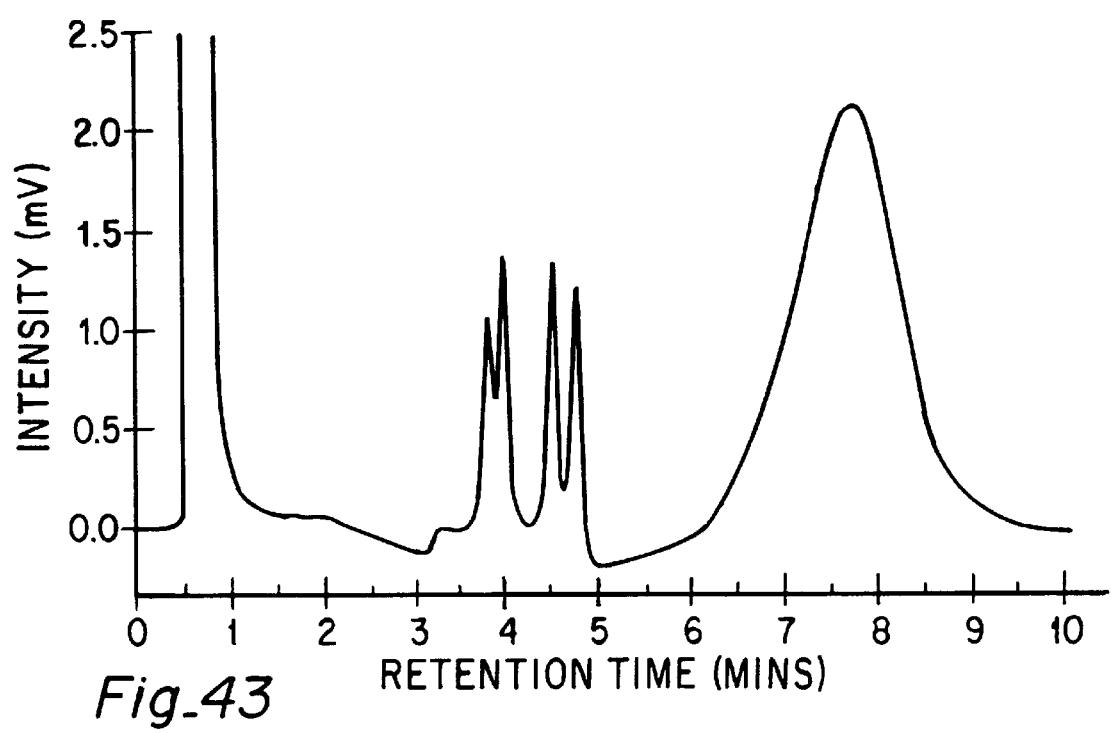
FIG. 43 is an elution profile of another injection of the same 209 bp mixture and using the same column as in FIG. 42, but after changing the guard cartridge and replacing the pump-valve filter.
Figure 44:
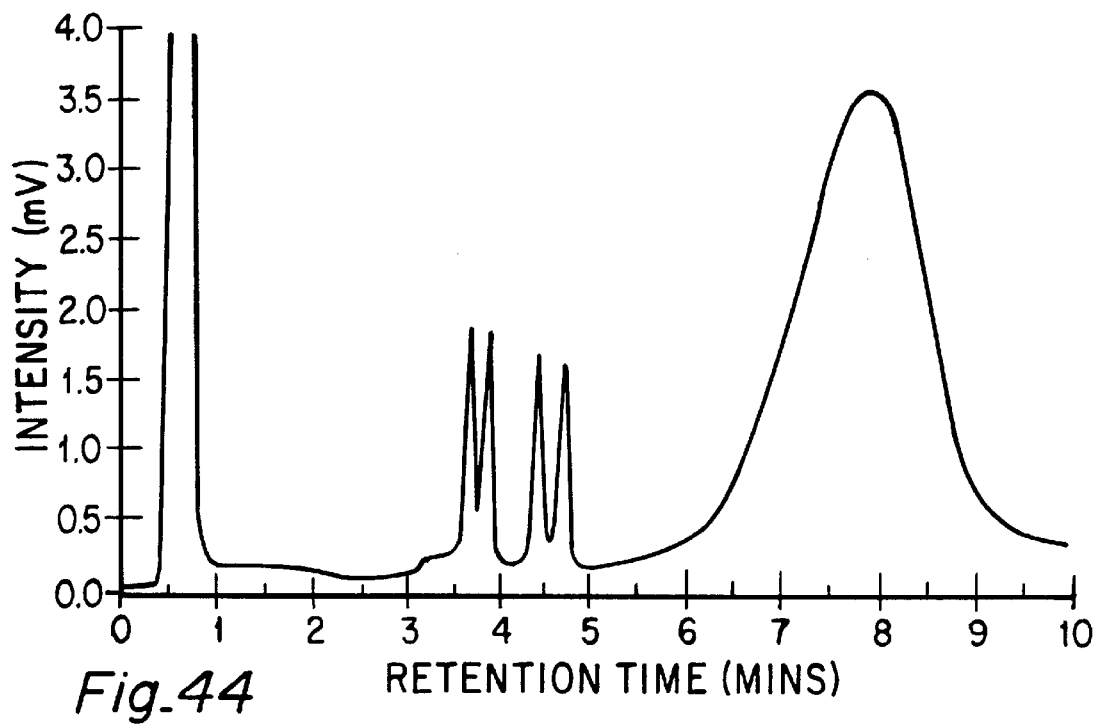
FIG. 44 is an elution profile of another injection of the same 209 bp mixture and using the same column as in FIG. 43, but after flushing the column with 0.1 M TEAA, 25% acetonitrile, and 0.32 M EDTA for 45 minutes at 75° C.

The effectiveness of the surprising discovery made by Applicants that washing a MIPC column with a multivalent cation binding agent restores the ability of the column to separate heteroduplexes and homoduplexes in mutation detection protocols under DMIPC conditions, is described in Example 24 and demonstrated in FIGS. 42, 43, and 44.

As described in Example 24, Applicants noticed a decrease in resolution of homoduplexes and heteroduplexes during the use of a MIPC column in mutation detection. However, no apparent degradation in resolution was observed when a DNA standard containing pUC18 HaeIII digest (Sigma/Aldrich Chemical Co.) was applied at 50° C. (not shown). In order to further test the column performance, a mixture of homoduplexes and heteroduplexes in a 209 bp DNA standard was applied to the column under DMIPC conditions of 56° C. (Kuklin et al., *Genetic Testing* 1:201 (1998). It was surprisingly observed the peaks representing the homoduplexes and heteroduplexes of the mutation detection standard were poorly resolved (FIG. 42).

FIG. 43 shows some improvement in the separation of homoduplexes and heteroduplexes of the standard mutation detection mixture when a guard cartridge containing cation capture resin was deployed in line between the solvent reservoir and the MIPC system. The chromatography shown in FIG. 43 was performed at 56° C. The column used in FIG. 43 was the same column used in the separation shown in FIG. 42 and for separating the standard pUC18 HaeIII digest.

FIG. 44 shows the separation of homoduplexes and heteroduplexes of the standard mutation detection mixture at 56° C. on the same column used to generate the chromatograms in FIGS. 42 and 43. However, in FIG. 44 the column was washed for 45 minutes with a solution comprising 32 mM EDTA and 0.1M triethylammonium acetate in 25% acetonitrile at 75° C. prior to sample application. FIG. 44 shows four cleanly resolved peaks representing the two homoduplexes and the two heteroduplexes of the standard 209 bp mutation detection mixture. This restoration of the separation ability, after washing with a solution containing a cation binding agent, of the MIPC column under DMIPC conditions compared to the chromatograms of FIGS. 42 and 43 clearly shows the effectiveness and the utility of the present invention.

In an important aspect of the present invention, Applicants have developed a standardized criteria to evaluate the performance of a DMIPC separation media. DMIPC as used herein, is defined as a process for separating heteroduplexes and homoduplexes using non-polar beads in the column, wherein the process uses a counterion agent, and an organic solvent to desorb the nucleic acid from the beads, and wherein the beads are characterized as having a Mutation Separation Factor (MSF) of at least 0.1. In an operational embodiment, the beads have a Mutation Separation Factor of at least 0.2. In a preferred embodiment, the beads have a Mutation Separation Factor of at least 0.5. In an optimal embodiment, the beads have a Mutation Separation Factor of at least 1.0.

The performance of the column is demonstrated by high efficiency separation by DMIPC of heteroduplexes and homoduplexes. We have found that the best criterion for measuring performance is a Mutation Separation Factor as described in Example 23. This is measured as the difference between the areas of the resolved heteroduplex and homoduplex peaks. A correction factor may be applied to the generated areas underneath the peaks. Factors, such as the following listed below, may affect the calculated areas of the peaks and reproducibility of the same: baseline drawn, peak normalization, inconsistent temperature control, inconsistent elution conditions, detector instability, flow rate instability, inconsistent PCR conditions, and standard and sample degradation.

The Mutation Separation Factor (MSF) is determined by the following equation:

$$MSF = (\text{area peak 2} - \text{area peak 1})/\text{area peak 1}$$

where area peak 1 is the area of the peak measured after DMIPC analysis of wild type and area peak 2 is the total area of the peaks or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

Other features of the invention will become apparent in the course of the following descriptions of exemplary embodiments which are given for illustration of the invention and are not intended to be limiting thereof.

All references cited herein are hereby incorporated by reference in their entirety.

Procedures described in the past tense in the examples below have been carried out in the laboratory. Procedures described in the present tense have not yet been carried out in the laboratory, and are constructively reduced to practice with the filing of this application.

EXAMPLES

Examples 1

Sample Concentration by Application of a Plurality of Sample Aliquots

A 5 µL standard sample 0.2 µg pUC18 HaeIII restriction digest, D6293, Sigma/Aldrich Chemical Co.,) containing 80, 102, 174, 257, 167, 298, 434, 458, 587 base pair DNA fragments was injected onto a MIPC column and the column was eluted under gradient conditions to produce a reference chromatogram as shown in FIG. 1. The pH 7 mobile phase comprised component A, 0.1M triethylammonium acetate (TEAA) and component B, 0.1M TEAA, 25% acetonitrile. Gradient conditions used in the separation shown in FIG. 1 were 35 to 55% B in three minutes, followed by 55 to 65% B in seven minutes, 65% B for 2.5 minutes, 100% B (column wash) for 1.5 minutes, and 35% B for 2 minutes to equilibrate the column for the next sample application. The backpressure was 2100 psi, temperature 50° C., UV detection at 260 nm, flow rate of 0.75 mL/min. The column was a DNASep™ (621-0546, Transgenomic, Inc. San Jose, Calif.) 50×4.6 mm i.d.

In a separate experiment, another 5 µL sample of pUC18 DNA-HaeIII digest was applied to a MIPC column and washed in an isocratic mode with 35% B for 10 minutes. FIG. 2 shows that no DNA fragments eluted as represented by the flat baseline of the chromatogram. A second 5 µL pUC18 DNA-HaeIII digest was injected onto the same MIPC column and the column was eluted (FIG. 3) with 35% B followed by the gradient described above in relation to FIG. 1.

Example 2

Melting Profiles and Mutation Detection of 200 bp Fragments Based on Primer Design p53 exon 6 genomic DNA having a C to T mutation at location 13346 was amplified by PCR in which three different sets of primers were used. Each primer set was designed to produce DNA fragments (amplicons) having the mutation located in a different melting domain. The melting profiles, calculated using WinMelt™, showing the melting domains of the three fragments and the relative position of mutation within the fragments is shown in FIG. 4. The primers which produced the 200 bp fragment 1 were designed to locate the mutation at position 159, near the 3'-end of the fragment. The primers which produced the 201 bp fragment 2 were designed to locate the mutation at position 59, near the 5'-end of the fragment. The primers which produced the 200 bp fragment 3, were designed to locate the mutation at position 91, near the middle of the fragment. The melting profiles of the three fragments in FIG. 4 are presented relative to the point of mutation. The temperature and sequence positions do not refer to a specific temperature and base pair length, but rather, refer to relative temperature and sequence position.

The primer sets used are indicated in the following table:

| Fragment 1 | |
|---|---|
| Forward Primer | 5'-ACGGAGGTTGTGAGGCGCTG (SEQ ID NO:1) |
| Reverse Primer | 5'-CTGTCATCCAMTACTCCACACGC (SEQ ID NO:2) |
| Forward Primer | 5'-CAGGCCTCTGATTCCTCATG (SEQ ID NO:3) |
| Reverse Primer | 5'-CCACTGACMCCACCCTTMCC (SEQ ID NO:4) |
| Forward Primer | 5'-MGAATTCACAGGGCTGT (SEQ ID NO:5) |
| Reverse Primer | 5'-TAGGATCCAGTTGCAAACCAGACCTCAG (SEQ ID NO:6) |

The PCR conditions used with each of the three primer sets are described below. For each set of primers, the components shown in the following table were combined, vortexed to ensure good mixing, and centrifuged:

| COMPONENT NAME | QUANTITY |
|---|---|
| 10X Taq polymerase buffer | 10 µL |
| 10X dNTP mixture | 10 µL |
| Forward primer, 10 µM | 2 µL |
| Reverse primer 10 µM | 2 µL |
| Water | 73.5 µL |
| Taq (AmpliTaq ® DNA polymerase) | 0.5 µL |
| p53 DNA template | 2 µL |

Aliquots were then distributed into PCR tubes. The PCR tubes were placed into thermocycler and the temperature cycling program was initiated. The cycling program parameters are shown in the table below:

| STEP | TEMPERATURE, ° C. | TIME, seconds |
|---|---|---|
| 1 | 94 | 120 |
| 2 | 94 | 10 |
| 3 | 56 | 20 |
| 4 | 72 | 30 |
| 5 | Repeat from step 2, 34X | |
| 6 | 72 | 30 |
| 7 | 4 | |
| 8 | end | |

The PCR products produced using the above protocol were analyzed by DMIPC using a Transgenomic WAVE™ DNA Fragment Analysis System (Transgenomic, Inc., San Jose, Calif.). Following initial DMIPC analysis, the samples were hybridized by heating to 95° C. for four minutes, then slowly cooling to 25° C. The samples were then re-analyzed by DMIPC.

The DMIPC conditions used for the mutation detection separations shown in the chromatograms of FIGS. 5, 6 and 7 are shown below:

| TIME, min. | % A | % B |
|---|---|---|
| 0.0 | 56 | 44 |
| 0.1 | 51 | 49 |
| 9.1 | 42 | 58 |
| 9.2 | 0 | 100 |
| 9.7 | 0 | 100 |
| 9.8 | 56 | 44 |
| 12.3 | 56 | 44 |

The mobile phase contained solvent A: 0.1M TEAA and solvent B: 0.1M TEAA in 25% acetonitrile at a flow rate of 0.9 mL/min. The column temperature during DMIPC was 61° C. for fragment 1, 61° C. for fragment 2, and 62° C. for fragment 3.

Example 3

Figure 8:
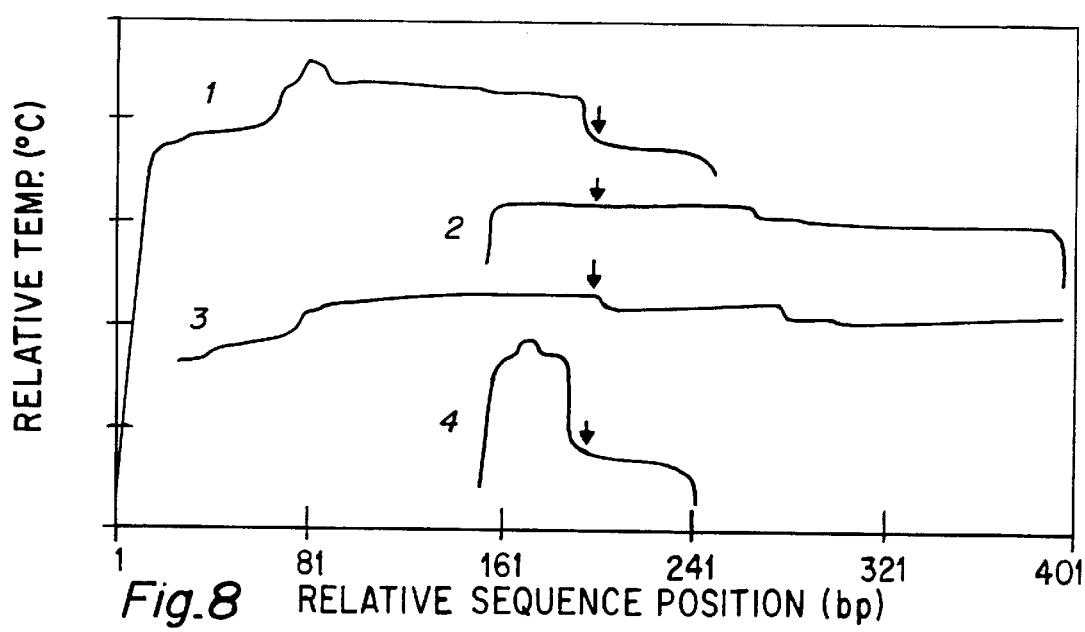
FIG. 8 shows the melting map of four DNA fragments with a mutation site indicated by an arrow.

Melting Profiles and Mutation Detection of 100–400 bp Fragments Based on Primer Design The template was bacteriophage Lambda (base pairs 31500–32500) with a mutation at position 32061 (available from FMC Corp. BioProducts, Rockland, Me.) was amplified by means of PCR processes in which four different sets of primers were used. The Lambda sequence has been published by O'Conner et al. in *Biophys. J* 74:A285 (1998) and by Garner et al at the Mutation Detection 97 4th International Workshop, Human *Genome Organization, May* 29–Jun. 2, 1997, Brno, Czech Republic, Poster no. 29. Each primer set was designed to produce amplicon fragments such that each would have the mutation located in a different melting domain. The melting maps, as calculated using WinMelt™, showing the melting domains of the four amplicon fragments and the relative position of the mutation within the fragments is shown in FIG. 8. The primers which produced the 248 bp fragment 1 were designed to locate the mutation at position 198, near the 3'-end of the fragment. The primers which produced the 253 bp fragment 2 were designed to locate the mutation at position 50, near the 5'-end of the fragment. The primers which produced the 400 bp fragment 3, were designed to locate the mutation at position 199, near the middle of the longest fragment. The primers which produced the 100 bp fragment 4, were designed to locate the mutation at position 51, near the middle of the shortest fragment. The melting maps of the 4 fragments in FIG. 8 are presented relative to the point of mutation. The temperature and sequence positions do not refer to a specific temperature and base pair length, but rather, refer to relative temperature and sequence position.

The primer sets used are indicated in the following table:

| Fragment 1 | |
|---|---|
| Forward Primer | 5'-ACATTTTCATGTCAGGCCAC (SEQ ID NO:7) |
| Reverse Primer | 5'-ATCGTCAGMCTGACACAGG (SEQ ID NO:8) |
| Fragment 2 | |
| Forward Primer | 5'-GGATMTGTCCGGTGTCATG (SEQ ID NO:9) |
| Reverse Primer | 5'-ATACACTGCAGMCGTCAGC (SEQ ID NO:10) |
| Fragment 3 | |
| Forward Primer | 5'-ACATTTTCATGTCAGGCCAC (SEQ ID NO:7) |
| Reverse Primer | 5'-ATACACTGCAGMCGTCAGC (SEQ ID NO:10) |
| Fragment 4 | |
| Forward Primer | 5'-GGATMTGTCCGGTGTCATG (SEQ ID NO:9) |
| Reverse Primer | 5'-ATCGTCAGMCTGACACAGG SEQ ID NO:8 |

The PCR conditions used with each of the three primers are described in the tables below. All the components were combined, vortexed to ensure good mixing, and centrifuged. Aliquots were then distributed into PCR tubes as shown in the following table:

| COMPONENT | FRAGMENT 1 | FRAGMENT 2 | FRAGMENT 3 | FRAGMENT 4 |
|---|---|---|---|---|
| Pfu 10X Buffer | 5 μL | 5 μL | 5 μL | 5 μL |
| 100 μM dNTP mixture | 4 μL | 4 μL | 4 μL | 4 μL |
| Forward primer | 13.5 μL | 7.5 μL | 13.5 μL | 7.5 μL |
| Reverse primer | 8.5 μL | 7 μL | 7 μL | 8.5 μL |
| water | 13.5 μL | 21 μL | 15 μL | 19.5 μL |
| Lambda DNA template | 5 μL | 5 μL | 5 μL | 5 μL |
| PFU Turbo | 0.5 μL | 0.5 μL | 0.5 μL | 0.5 μL |

The PCR tubes were placed into a thermocycler and the temperature cycling program was initiated. The cycling program parameters are shown in the table below:

| STEP | TEMPERATURE, ° C. | Time, minutes |
|---|---|---|
| 1 | 94 | 2 |
| 2 | 94 | 1 |
| 3 | 58 | 1 |
| 4 | 72 | 1 |
| 5 | Repeat from step 2, 34X | |
| 6 | 72 | 10 |
| 7 | End | |

The PCR products produced using the above protocol were analyzed by DMIPC using a Transgenomic WAVE™ DNA Fragment Analysis System (Transgenomic, INC., San Jose, Calif.). Following initial DMIPC analysis, the samples were hybridized by heating to 95° C. for four minutes, then slowly cooling to 25° C. The samples were then re-analyzed by DMIPC.

Figure 9:
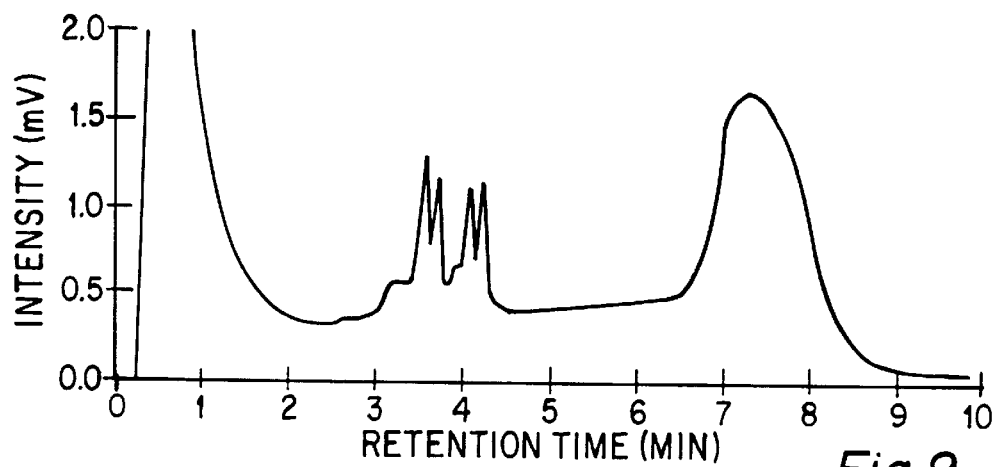
FIG. 9 shows the DMIPC elution profile of fragment 1 of FIG. 8.
Figure 10:
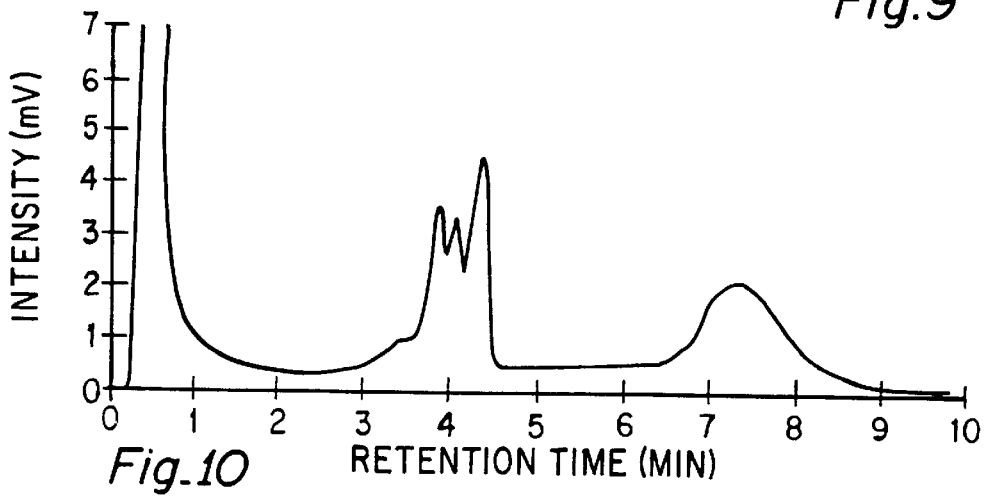
FIG. 10 shows the DMIPC elution profile of fragment 2 of FIG. 8.

The DMIPC conditions used for the mutation detection separations shown in the chromatograms of FIGS. 9 and 10 are shown below:

| TIME, min. | % A | % B |
|---|---|---|
| 0.0 | 50 | 50 |
| 0.1 | 45 | 55 |
| 4.6 | 36 | 64 |
| 4.7 | 0 | 100 |
| 5.2 | 0 | 100 |
| 5.3 | 50 | 50 |
| 7.8 | 50 | 50 |

Figure 11:
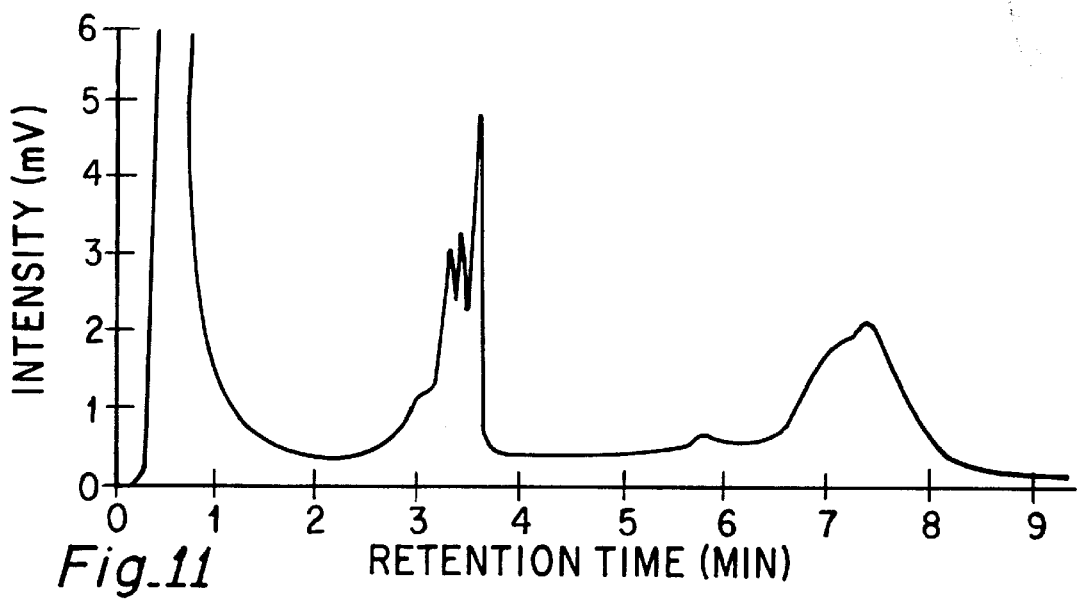
FIG. 11 shows the DMIPC elution profile of fragment 3 of FIG. 8.

The DMIPC conditions used for the mutation detection separations shown in the chromatograms of FIG. 11 are shown below:

| TIME, min. | % A | % B |
|---|---|---|
| 0.0 | 46 | 54 |
| 0.1 | 41 | 59 |
| 4.6 | 32 | 68 |
| 4.7 | 0 | 100 |
| 5.2 | 0 | 100 |
| 5.3 | 46 | 54 |
| 7.8 | 46 | 54 |

Figure 12:
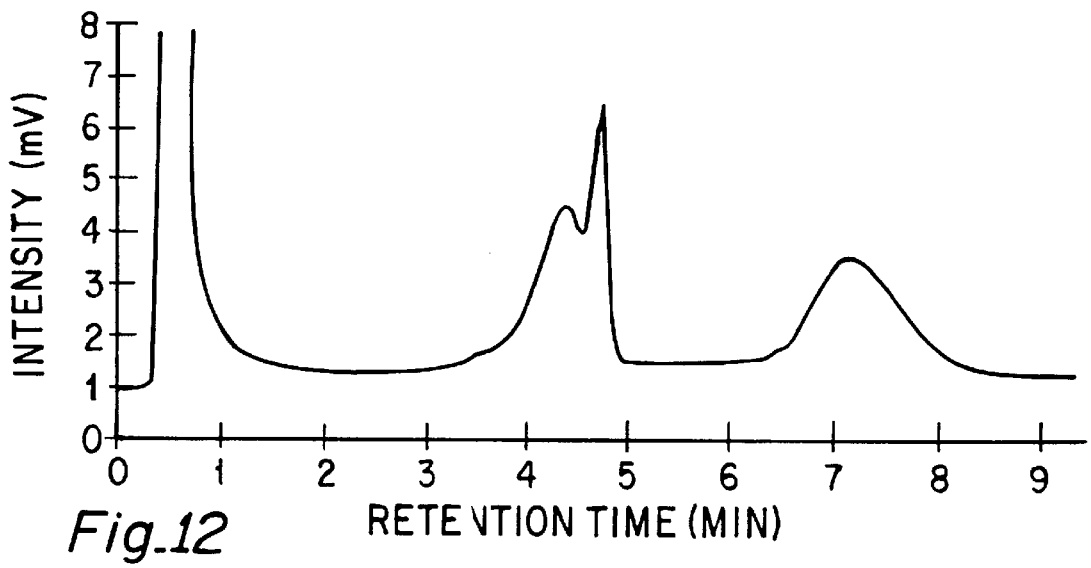
FIG. 12 shows the DMIPC elution profile of fragment 4 of FIG. 8.

The DMI PC conditions used for the mutation detection separations shown in the chromatograms of FIG. 12 are shown below:

| TIME, min. | % A | % B |
|---|---|---|
| 0.0 | 61 | 39 |
| 0.1 | 56 | 44 |
| 4.6 | 47 | 53 |
| 4.7 | 0 | 100 |
| 52 | 0 | 100 |
| 5.3 | 61 | 39 |
| 7.8 | 61 | 39 |

For FIGS. 9–12, the mobile phase contained solvent A: 0.1M TEAA and solvent B: 0.1M TEAA in 25% acetonitrile at a flow rate of 0.9 mL/min. The column temperature during DMIPC was 62° C. for fragment 1, 62° C. for fragment 2, 63° C for fragment 3, and 60° fragment 4.

Example 4

Polymerase Chain Reaction (PCR) Materials and Procedure

Samples for PCR amplification were purchased from Perkin-Elmer Applied Biosystems (Foster City, Calif.) in the GeneAmp (PCR Reagent Kit (Part No. N801-0055), which included AmpliTaq® (DNA polymerase, GeneAmp (10× PCR Buffer, dNTP's as well as DNA template and primers. To compare the effect of DNA polymerase on PCR fidelity, additional samples were prepared which substituted Cloned Pfu DNA Polymerase (Cat. No. 600153, Stratagene, La Jolla, Calif., USA) and PFUTurbonm DNA Polymerase (Cat. No. 600250, Stratagene) for AmpliTaq® DNA polymerase. In these samples, the GeneAmp 10×PCR Buffer was replaced with 10×Cloned Pfu DNA polymerase reaction buffer (Cat. No. 600153-82, Stratagene). The DNA template was diluted to 100 ng/mL in 10 mM Tris-HCl, pH 8.0 (Cat. No. 0291, Teknova, Half Moon Bay, Calif., USA), 1 mM EDTA, pH 8.0 (Cat. No. 0306, Teknova), 10 mM NaCl (Cat. No. S7653, Sigma, St. Louis, Mo., USA). A 500-bp product was amplified from the DNA control template (bacteriophage Lambda DNA) from Control Primer #1 (5'-GATGAGTTCGTGTCCCTACMCTGG-3') (SEQ ID NO:11) and Control Primer #2 (5'-GGTTATCGAAATCGCCACAGCGCC-3') (SEQ ID NO:12).

Components were added to PCR tubes (Part No. TFI-0201, MJ Research, Watertown, Mass., USA) in the following order: 53 μL ddH20, 10 μL 10×PCR buffer, 200 μM each dNTP, 2.5 U/100 μL AmpliTaq®, Cloned Pfu or PFU-Turbo™ DNA Polymerase,1 μM Control Primer #1, 1 μM Control Primer #2, and 1 ng DNA control template to total 100 μL. Amplification was performed on the MJ Research (Watertown, Mass., USA) PTC-100 Thermocycler using 15 or 35 PCR cycles.

Example 5

Cleavage of 500 Base Pair PCR Product to Create Blunt Ends

The 500 bp PCR product has four cleavage cites for HaeIII endonuclease (R5628, Sigma-Aldrich, St. Louis, Mo., USA) at bases 37, 47, 452 and 457, producing a 405 bp blunt ended product. HaeIII was diluted 1:30 with ddH20. In a PCR tube, diluted HaeIII was added to PCR product (1 part diluted HaeIII:2 parts PCR sample), vortexed, then incubated at room temperature. The PCR samples were analyzed before, during and after digestion with HaeIII to ensure the cleavage was complete.

Example 6

MIPC of 500 Base Pair PCR Product and 405 Base Pair Blunt End Product

Figure 17:
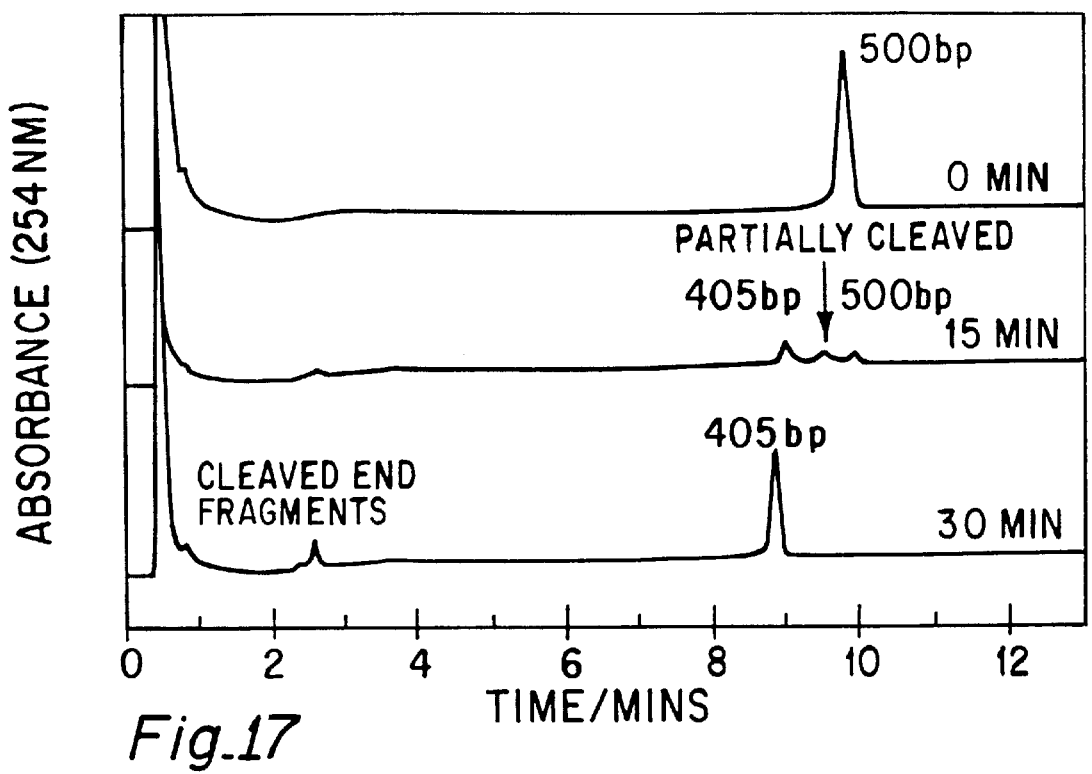
FIG. 17 shows a MIPC chromatogram of a 500 bp PCR product and a 405 bp blunt end fragment.

As shown in FIG. 17, a 405 bp blunt ended product was produced after a 500 bp PCR product was cleaved with HaeIII endonuclease. At 0 minutes, a full 500 bp product peak was seen before cleavage with HaeIII. After 15 minutes, the 500 bp product had been partially cleaved, showing 3 species: uncleaved 500 bp, partially cleaved intermediate species with portion of the ends removed, and cleaved 405 bp product. Finally, after 30 minutes, cleavage of all 4 end fragments was complete. MIPC analysis conditions using the WAVE™ DNA Fragment Analysis System, were as follows: Solvent A: 0.1M TEAA, Solvent B: 0.1M TEAA, 25% Acetonitrile, linear gradient from 31–53% solvent B in 0.1 minute, 53–77% B in 12 minutes; flow rate: 0.9 mL/min; temperature: 50° C.; detection; UV, at 254 nM.

Example 7

PCR-induced Mutation Analysis by MIPC and Corresponding Reaction Product Profiles As a baseline, a sample was run under conditions that would intentionally enhance the mutation rate, but could be found in a typical PCR lab. This control sample, containing PCR mutations in 61.7% of its fragments, was amplified using AmpliTaq® DNA polymerase with 35 PCR cycles. Additional samples were run to study factors which effect the PCR fidelity. These samples were identical to the control except for a change in the cycle number, or type of DNA polymerase. Samples which were PCR amplified using 15 cycles of AmpliTaq®) had a 51.6% mutation rate. This 10.1% decrease from the 35 cycle amplification is expected since with fewer cycles there are fewer opportunities for mutations to occur. Substituting Pfu or PFUTurbo™ for AmpliTaq® DNA polymerase had a positive effect on the fidelity of the PCR product. PFUTurbo™ had an error rate equal to Pfu, but produced a higher yield due to a novel thermostable factor (Stratagene, PFUTurbo™ DNA Polymerase Instruction Manual, Revision #107001). The mutation rate dropped to 24.8% and 18.4% for Pfu and PFU-Turbo™, respectively (FIG. 20)

An additional experiment was performed to further optimize PCR conditions using Pfu and PFUTurbo™. After reducing the dNTP concentration from 200 $\mu$M to 100 $\mu$M each dNTP, dropping the primer concentration from 1 $\mu$M to 0.2 $\mu$M, and amplifying samples using a modified "touchdown" PCR protocol, the mutation rate dropped to 23.1% and 17.8% for Pfu and PFUTurbo™, respectively.

Example 8

Analysis of PCR Yield by MIPC and Corresponding Reaction Product Profiles

A 405 bp PCR product was amplified with AmpliTaq®, Pfu and PFUTurbo™. Substituting Pfu or PFUTurbo™ for AmpliTaq® DNA polymerase had a positive effect on the yield of the PCR product. The yield of homoduplex product was determined by integration of the peak area and that of a standard of known quantity. AmpliTaq® gave the lowest yield (10 ng) and a large quantity of primer dimer (peak at 2 mins). Pfu or PFUTurbo™ gave yields of 35 ng and 93 ng, respectively, and lower amounts of primer dimers (FIG. 19). MIPC analysis conditions using the WAVE™ DNA Fragment Analysis System, were as follows: Solvent A: 0.1M TEAA, Solvent B: 0.1M TEAA, 25% Acetonitrile; linear gradient from 31–53% solvent B in 0.1 min, 53–71% B in 9 min; flow rate: 0.9 mL/min; temperature: 66° C.; detection: UV, 254 nM.

Example 9

Effect of Temperature on the Separation of Homoduplexes and Heteroduplexes by MIPC A 405 bp PCR product was amplified with AmpliTaq® was chromatographed under partially denaturing conditions (FIG. 18). Samples were run at 62° C., 64° C., and 66° C. The main peak corresponded to pure homoduplex DNA of length 405 bp. It is concluded that upon increasing the temperature, the retention times decrease due to partial denaturation. At 66° C., the sample showed the greatest resolution between the homoduplex and heteroduplex peaks. MIPC analysis conditions using the WAVE ™ DNA Fragment Analysis System, were as follows: Solvent A: 0.1M TEAA, Solvent B: 0.1M TEAA, 25% Acetonitrile; linear gradient from 31–53% solvent B in 0.1 min, 53–71% B in 9 min; flow rate: 0.9 mL/min; temperature: 66° C.; detection: UV, 254 nM.

Example 10

Effect of Hybridization on the Analysis of PCR Replication Fidelity by MIPC A final hybridization cycle is necessary to melt and reanneal strands to form homoduplexes and heteroduplexes. To inhibit further polymerizing activity, EDTA (Cat. No. 0306, Teknova, Half Moon Bay, USA), at a final concentration of 20 mM, was added to chelate free magnesium remaining in the PCR samples. The samples were then loaded into the thermocycler (Model PTC-100,MJ Research), heated to 95° C. for 4 minutes, then slowly cooled to 25° C. After hybridization, the heteroduplex peak (at 5.6 min) increased from 8.2% to 23.1% mutation, showing that an artificially low mutation rate would be produced by elimination of this step. MIPC analysis conditions using the WAVE™ DNA Fragment Analysis System, were as follows: Solvent A: 0.1M TEAA, Solvent B: 0.1M TEAA, 25% Acetonitrile; linear gradient from 31–53% solvent B in 0.1 min, 53–71% B in 9 min; flow rate: 0.9 mL/min; temperature: 66° C.; detection: UV, 254 nM.

Example 11

Separation and Isolation of Pure PCR Product by MIPC 138 ng of a 209 bp DNA fragment (DYS271 from the human Y chromosome) was injected onto a MIPC column and separated under non-denaturing conditions (52° C.). The peak corresponding to the fragment was collected in a 300 $\mu$L vial. Aliquots of the collected liquid (5 $\mu$L and 20 $\mu$L in separate experiments) were then amplified directly by PCR and quantified (in nanogram units) by re-analysis on the WAVE™ System. A control was performed by diluting a portion of the original such that both the control and the collected fractions gave the same peak area when re-injected onto the WAVE™ System. The initial copy number of DNA in the control then matched that in the collected fraction. Any difference in PCR yield should reflect only the effect of the elution buffer in which the fractions were collected. MIPC analysis conditions using the WAVE™ DNA Fragment Analysis System, were as follows: Solvent A: 0.1M TEAA, Solvent B: 0.1M TEAA, 25% Acetonitrile; linear gradient from 43–57% solvent B in 0.5 min, 29–71% B in 7.5 min; flow rate: 0.9 mL/min; temperature: 52° C.; detection: UV, 254 nM. The following reagents were used: 10 mM Tris buffer pH 8, 100 µM each dNTP, 0.2 µM primers, 2.5 mM $MgCl_2$ 2.5 U Perkin-Elmer AmpliTaq®.

Example 12

Adjustment of PCR Primers Based on Detection by MIPC of Excessive Primer Dimer Formation For long-range primer design, detection of unknown mutations requires a highly sensitive and reproducible method. To achieve such level of accuracy, it is better to fragment the exon into 150–450 bp sections despite the fact that single-base mutations have been detected in 1.5-k bp fragments. If the sequence is known, the melting map is constructed using appropriate software. Regions that differ by more than 15° C. in the same fragment should be avoided. If this is not possible, substitute dGTP with $N^7$-dGTP (7-deaza-2'-deoxyguanosine 5'-triphosphate) to lower the melting temperature of GC rich regions, or to include a short G-C clamp of 3 or 4 bases.

For local primer design, primers with non-template tails such as universal sequencing primers or T7 promoters should be avoided. The difference in Tm between Primer 1 and 2 is less than 1° C. Difference in Tm between primer and template is about 25° C. The 3'-pentomer of each primer is more stable than ΔG, =–6 kcal/mol. Any possible primer dimers should be less stable than the 3'-pentomer by at least 5 kcal/mol. To avoid degradation, storage in Tris-HCl (pH 8.0) buffer is preferable rather than in pure water.

Example 13

Adjustment of PCR Variables to Reduce PCR Induced Mutations Detected by MIPC Despite the Use of Proof Reading Enzyme For smaller fragments up to 250 bp, Taq or Taq Gold™ (Perkin-Elmer Applied Biosystems, Foster City, Calif., USA) usually give satisfactory results, although Pfu will still give the best results particularly above 25 cycles of amplification (Taq can easily cause 15% of dsDNA fragments to contain one or more mutations). As a guide, use Taq only if cycle number multiplied by base-pairs are less than 10,000. PCR reactions should be performed with the manufacturers recommended buffer and the following recommended conditions: 2.0–2.5 mM $MgCl_2$, 100 µM each dNTP, 0.2 µM each primer, 2.5U per 100 µL of Pfu, Taq (or Taq Gold™); about 50 ng template.

Example 14

Reduction of Excessive by Products, Detected by MIPC, Resulting from an Excessive Number of PCR Cycles One can experimentally manipulate the probability of DNA sequence changes by altering the number of cycles (n) and/or the polymerase error rate per nucleotide (p): f=np/2, where f is the error frequency, n is the number of pcr cycles and p is the error rate. For example, the expected error frequency when p=1/10000 is $1\times10^{-3}$ after 20 cycles, or one error per 1000 nucleotides. Thus the number of cycles should be kept to a minimum required to produce a feasible amount of product DNA.

Example 15

Analyte Hybridization Procedure

A PCR process is terminated by addition of 5 mM EDTA, 60 mM NaCl, 10 mM TrisHCl pH 8.0 to the reaction mixture. The reaction mixture is heated 95° C. for 3 min. then cooled to 25° C. over 45 min. Homozygous mutant must be combined with wild type in approximately 1:1 ratio prior to hybridization.

Example 16

Description of Temperature Dependent DMIPC Separation Process

The following Example refers to FIG. 24 (heteroduplex separations over a 51° to 61° C. temperature range).

A 209 base pair fragment from the human Y chromosome, locus DYS271 with an A to G mutation at position 168 was hybridized with wild type as described in Example 15 above and the sample was injected onto an MIPC column (50 mm×4.6 mm i.d.) at 51° C. The column was eluted at 0.9 mL/min with a gradient of acetonitrile in 0.1M TEAA over 7 minutes. The chromatography was monitored 260 nm using an UV detector. The heteroduplex present in the mixture was not denatured at 51° C.; therefore, a single peak was observed.

As seen in FIG. 24, the injection and chromatography of the sample was repeated at 1° C. incremental increases in temperature. A shoulder was observed on the low retention time side of the main peak at 53° C. indicating the potential presence of a heteroduplex. At 54° C. three peaks were seen. And at 550–58° C. four peaks were seen indicating the definite presence of a mutation. The two lower retention time peaks were two heteroduplexes and the higher retention time peaks were homoduplexes.

Example 17

Determination of T(hsst) by Starting a DMIPC Analysis at a Melting Temperature Calculated by Software The heteromutant site separation temperature T(hsst) of 209 base pair heteroduplexes in Example 16 above is determined by applying the formula T(hsst)=X+m·T(w) using a software package such as MELT. The melting temperature, T(w), determined by MELT was 52° C. The sample is applied to a MIPC column at 52° C. and eluted as described in Example 16 above. A single peak is seen. This result indicates that the sample either does not contain a mutation (heteroduplex) or the temperature at which the chromatography was performed is below the T(hsst). Therefore, the temperature is increased by 2° C. to 54° C. and chromatography is repeated. Three peaks are then apparent, indicating the presence of a mutation. The temperature is increased by another 2° C. increment to 56° C. and the chromatography is repeated. The separation is optimized as evidenced by the appearance of two distinct heteroduplex peaks at lower retention time and two distinct homoduplex peaks at higher retention time. Using T(w)=52, m=+1, and X=+4 in the above formula, T(hsst) is determined to be 56° C.

Example 18

Determination of T(hsst) by Starting a DMIPC Analysis at a Melting Temperature Determined from a UV Melting Profile The T(hsst) is determined in a similar manner as for Example 17, but starting with a T(w) based on a UV melting profile obtained as described S. Lim (Varian Technical Note "DNA denaturation using the Cary ⅓ Thermal Analysis System", No. UV-51, pp. 1–5, June 1991, Varian Associates, Palo Alto, Calif.) and using a pH 7.3 buffer comprising 0.1 M TEAA, and acetonitrile at a concentration as obtained from FIG. 38 for a 209 bp fragment.

Example 19

Effect of Temperature on the Retention Time and Resolution of a Homoduplex/heteroduplex Mixture A 209 base pair fragment from the human Y chromosome, locus DYS271 with an A to G mutation at position 168 was hybridized with wild type as described in Example 15 above and the sample was injected onto an MIPC column (50 mm×4.6 mm i.d.) at 51° C. The chromatography was monitored 260 nm using an UV detector. The heteroduplex present in the mixture was not denatured at 51° C.; therefore, a single peak was observed. The column was eluted at 0.9 mL/min with a solvent A: 0.1M TEAA and solvent B: 0.1M TEAA, 25% acetonitrile using the following gradient:

| T (min) | % A | % B |
|---|---|---|
| 0 | 67 | 33 |
| 0.1 | 62 | 38 |
| 12.1 | 40 | 60 |
| 12.2 | 0 | 100 |
| 12.7 | 0 | 100 |
| 12.8 | 67 | 33 |
| 15.3 | 67 | 33 |

The DMIPC retention times of a DYS271 209 bp mutation standard mixture of heteroduplex and homoduplex species (available as a Mutation Standard from Transgenomic, Inc., San Jose, Calif.; the mutation is described by Seielstad et al., *Hum. Mol. Genet.* 3:2159 (1994)) was measured as a function of oven temperature starting at 50° C. and continuing in 0.5 and 0.3 degree increments up to 57.5° C. (FIG. 37) in a temperature titration. The HPLC instrument was a unit controlled via RS232 interface from customized system software. The software control was from Transgenomic Inc. (San Jose, Calif.) custom prototype front-end software package (an extensively modified version of WAVEMaker™). This oven was produced from a Model PTC200 M J Research thermocycler that was modified to contain a DNASep™ column and preheat lines (150cm×0.007" i.d.) made of PEEK tubing. The preheat tubing was interwound between the PCR tube wells (i.e., physically placed around the wells themselevs and in thermal contact with the 96-well heating block) and then was connected to the column placed in a cavity machined out of the thermocycler. The oven response was high with approximately 10 seconds required to reach a set temperature. It took about 2 minutes for the fluid to reach the set temperature. This response was much faster than conventional ovens for liquid chromatography. The oven was peltier cooled, so that increases and decreases in temperature were reached rapidly.

The mobile phase used in the separation comprised 0.1M TEAA (solvent A) and 0.1M TEAA in 25% acetonitrile (solvent B). The MIPC column was eluted with the gradient shown below at a flow rate of 0.9 mumin.

| Time | % A | % B |
|---|---|---|
| 0 | 55 | 45 |
| 0.1 | 50 | 50 |
| 6.1 | 38 | 62 |
| 6.2 | 0 | 100 |
| 6.7 | 0 | 100 |
| 6.8 | 55 | 45 |
| 9.3 | 55 | 45 |

Figure 37:
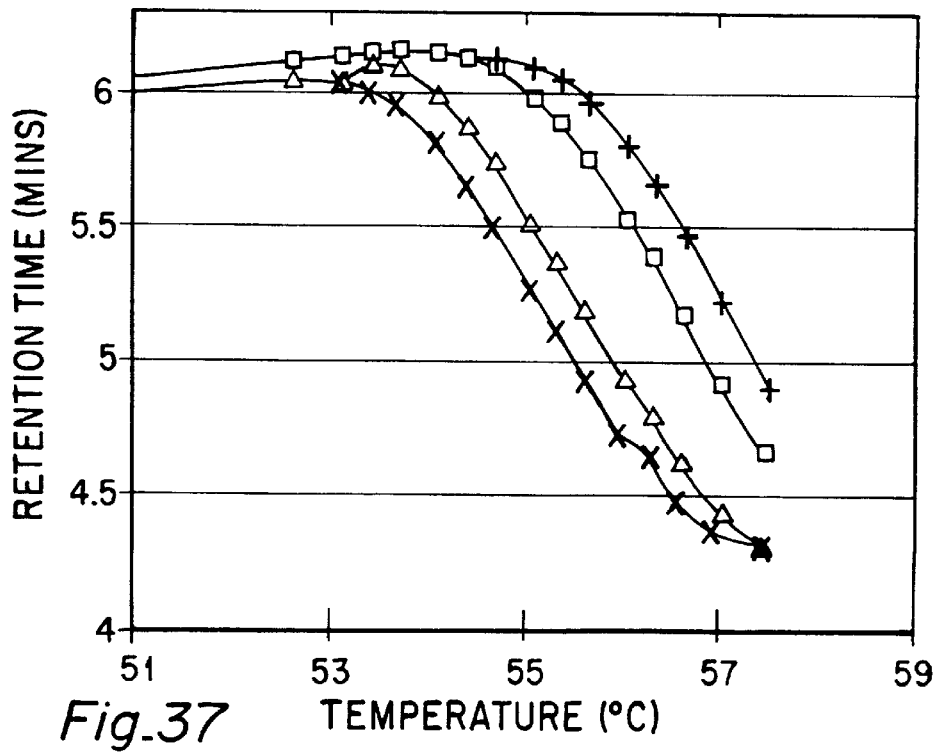
FIG. 37 shows the change in retention time with temperature for heteroduplex and homoduplex species in a DYS271 209 bp mutation mixture.

FIG. 37 illustrates the critical dependence of separations on oven temperature and, more importantly, on the mobile phase fluid temperature. Even a 0.1° temperature change will be reflected by a change in retention time and peak pattern. For genotyping of mutations, it is therefore critical that temperature is reproducible between runs and between instruments preferably to at least 0.1° C. and most preferably to at least 0.05° C. The data here shows the effect of temperature control based on the resolution of the homoduplexes and heteroduplexes is critical within a range of better than 0.1° C. The actual gradient d(retention time (min))/d (temperature (°C.)) from the plot was measured to be −0.875 min/°C.

Example 20

Preparation of a Reference Graph of Mobile Phase vs. Nucleotide Base Pair Length A standard pUC18 HaeIII restriction enzyme digest containing DNA fragments having base pair lengths of 80, 102, 174, 257, 267, 298, 434, 458 and 587 was applied to an MIPC column at non-denaturing temperature, 50° C. The column was eluted with a mobile phase linear gradient comprising Solvent A (0.1M TEAA, pH 7) and Solvent B (0.1M TEAA in 25% acetonitrile). The flow rate was 0.75 mL/min and detection was by UV at 260 nm. The gradient is shown below:

| TIME, min. | % A | % B |
|---|---|---|
| 0.0 | 65 | 35 |
| 3.0 | 45 | 55 |
| 10,0 | 35 | 65 |
| 13.5 | 35 | 65 |
| 15.0 | 0 | 100 |
| 16.5 | 0 | 100 |
| 17.5 | 65 | 35 |
| 19 | 65 | 35 |

The reference curve (FIG. 40) was constructed by taking the retention time of each fragment and finding the corresponding %B from the gradient. The %B was then plotted against base pair as shown in FIG. 40.

Example 21

Selection of Mobile Phase For Mutation Detection

The example which follows is for a 500 base pair DNA fragment. However, the same solvent selection approach is used for DNA fragments of any base pair length.

To select a preliminary mobile phase organic solvent concentration for mutation detection, the %B corresponding to the base pair length fragment of interest is obtained from the reference graph (FIG. 40). Using this reference, the preliminary solvent concentration of 65% B is required to elute the 500 base pair fragment from an MIPC column under non-denaturing conditions of 50° C. To ensure complete removal of the fragment from the column during a mutation detection analysis, the mobile phase solvent concentration is augmented by 5 percentage units, to 70% B in this example. This is the final mobile phase organic solvent concentration. The initial mobile phase solvent concentration is set by subtracting 15 percentage units from the preliminary concentration B determined from the reference. In this example, the initial mobile phase solvent concentration is set at 50% B (65% minus 15%). The mobile phase gradient for the fragment bracketing range used in the mutation detection by MIPC is 2% per minute increase in the percent of B in the mobile phase over 10 minutes. This is followed by an immediate increase to 100% B for about 2 min to wash the column. After this wash, the mobile phase concentration is brought back to the initial 50% B for 2 minutes to equilibrate the column in preparation for the next sample injection. A graphical representation of the gradient described above is depicted in FIG. 41.

The procedure described above is used initially under non-denaturing conditions, for example 50° C., to establish the quality of a DNA sample which has been amplified by PCR. To detect the presence of mutations in the amplified sample the above procedure is repeated under partially denaturing conditions, for example 57° C. The appearance of one or more lower retention time peaks in the chromatogram under partially denaturing conditions indicates the presence of one or mutations (heteroduplexes).

Example 22

Use of PEEK and Titanium Frits in Mutation Detection

The resin lots used in this experiment were shown to be suitable for mutation detection having passed the Mutation Separation Factor test, with a value of >0.1, as described in Example 23.

The types of titanium frits used for columns have a significant effect on the capability to resolve heteroduplexes from homoduplexes. Work was performed with titanium frits from two separate lots. The source of all frits used in this example has been obtained from Isolation Technologies (Hopedale, Mass.). The elution conditions used in this example were identical to those used in FIG. 37.

Figure 45:
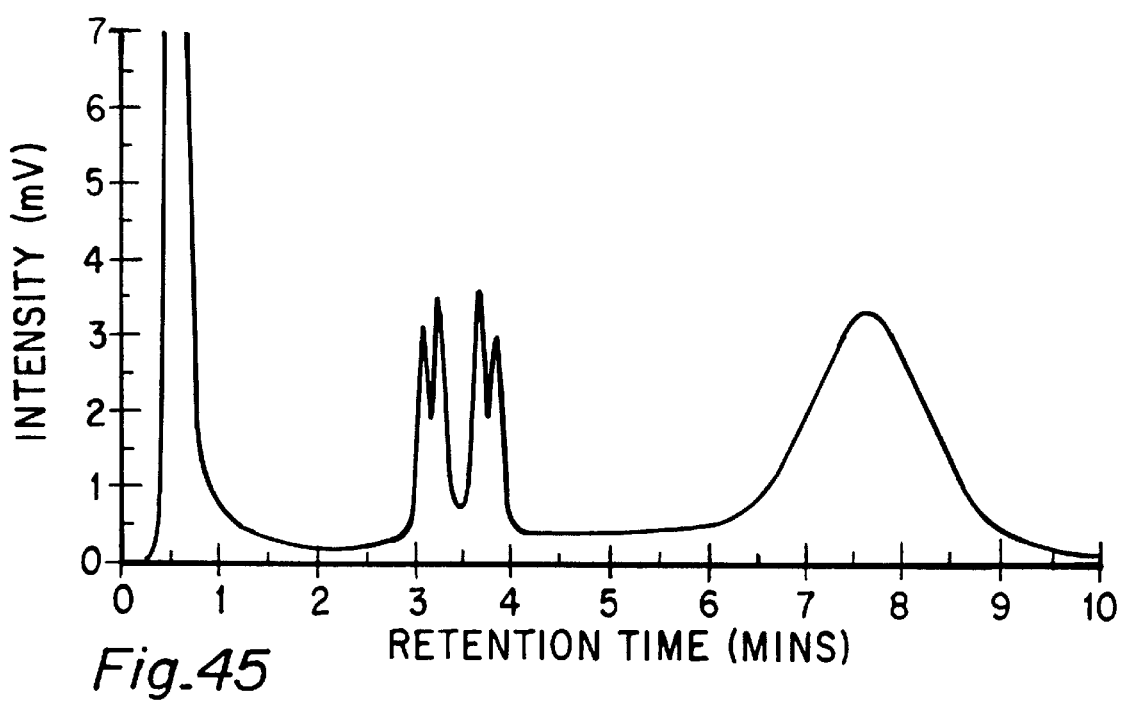
FIG. 45 is an elution profile of DYS271 209 bp mutation standard using titanium frits from lot A.
Figure 46:
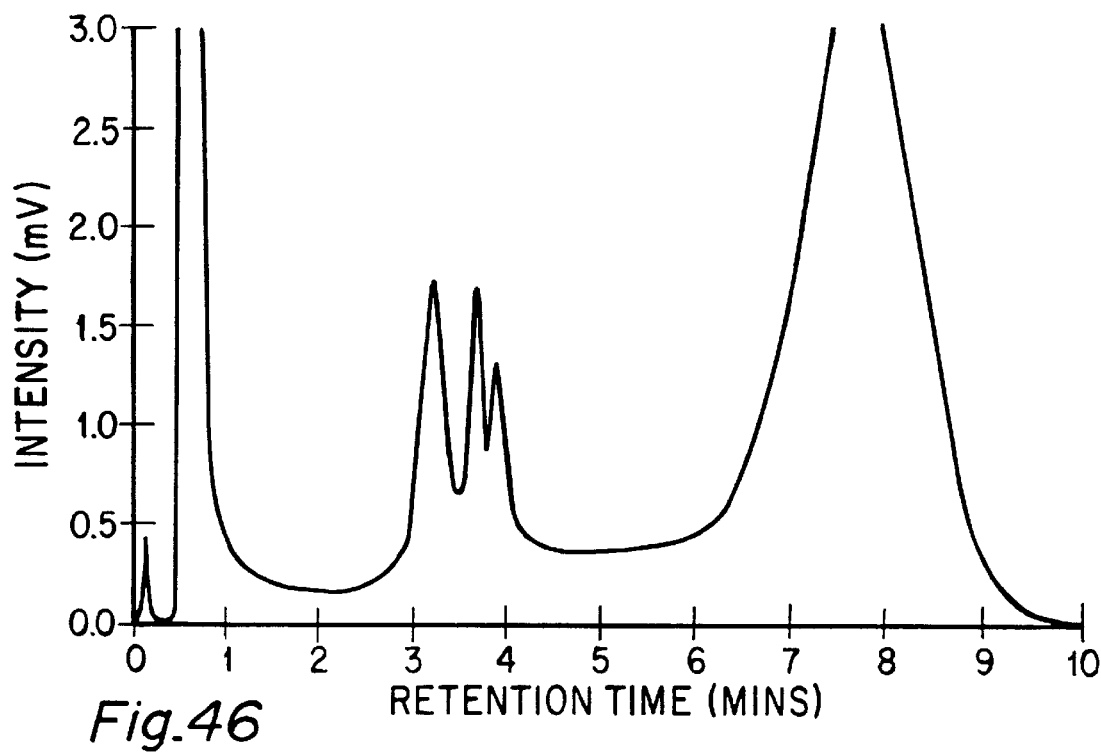
FIG. 46 is an elution profile of DYS271 209 bp mutation standard using titanium frits from lot B.

FIG. 45 shows the separation of the DYS271 209 bp mutation standard using titanium frits from lot A. Four peaks appear, with the two heteroduplex peaks clearly separated from the two homoduplex peaks, with retention times of 3.07 and 3.24 minutes for the heteroduplexes, and 3.65 and 3.82 minutes for the homoduplexes. However, in FIG. 46, the same 209 mutation standard using titanium frits from lot B yields a different result: only three peaks appear, and the second homoduplex peak has disappeared altogether. Thus, the type of titanium frit used may affect such resolution of heteroduplexes from homoduplexes. Treatment with 0.5M tetrasodium EDTA (sonication for 10 minutes and soaking for several days) has improved the performance of lot B.

Figure 47:
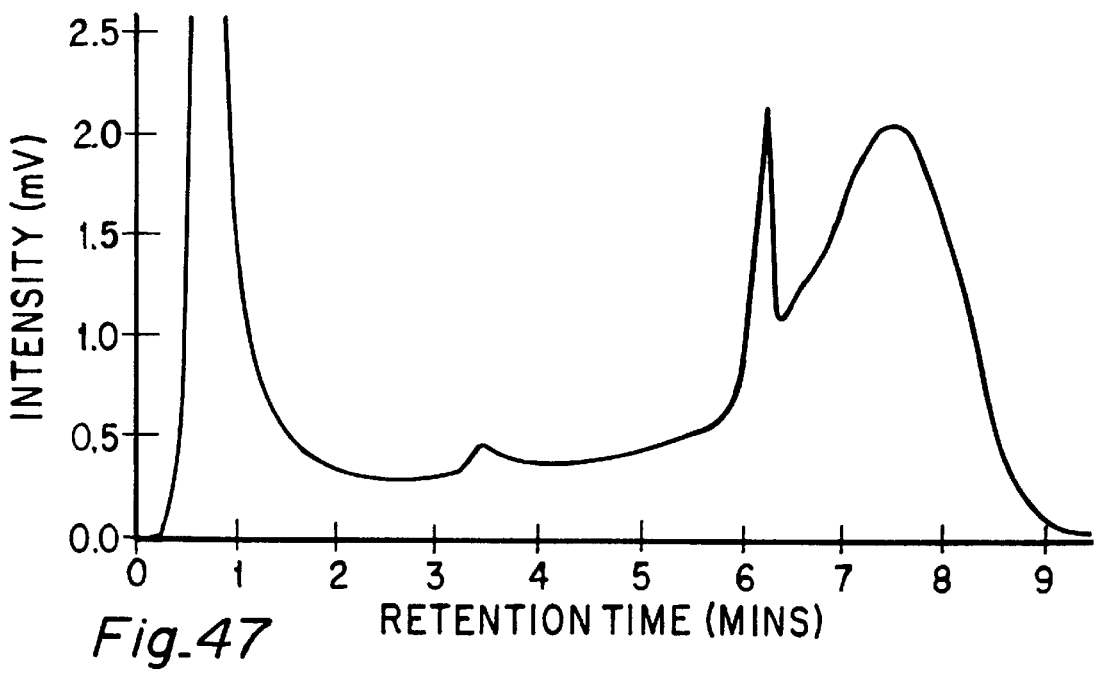
FIG. 47 is an elution profile of DYS271 209 bp mutation standard using PEEK frits.

Generally, columns containing PEEK frits are not able to separate heteroduplexes from homoduplexes satisfactorily unless very rigorous cleaning is performed. FIG. 47 shows that the optimum temperature at which the heteroduplexes are observed to separate from the homoduplexes is 56° C. Only one peak appears at a retention time of 3.45 minutes.

Example 23

Determination of the Mutation Separation Factor

The Mutation Separation Factor (MSF) is determined by the following equation:

$$MSF = (\text{area peak 2} - \text{area peak 1})/\text{area peak 1}$$

where area peak 1 is the area of the peak measured after DMIPC analysis of wild type and area peak 2 is the total area of the peaks or peaks measured after DMIPC analysis of a hybridized mixture containing a putative mutation, with the hereinabove correction factors taken into consideration, and where the peak heights have been normalized to the wild type peak height. Separation particles are packed in an HPLC column and tested for their ability to separate a standard hybridized mixture containing a wild type 100 bp Lambda DNA fragment and the corresponding 100 bp fragment containing an A to C mutation at position 51.

Depending on the packing volume and packing polarity, the procedure requires selection of the driving solvent concentration, pH, and temperature. Any one of the solvents can be used: acetonitrile, tetrahydrofuran, methanol, ethanol, or propanol. A counterion agent is selected from trialkylamine acetate, trialkylamine carbonate, trialkylamine phosphate, or any other type of cation that can form a matched ion with the polynucleotide anion.

Figure 49:
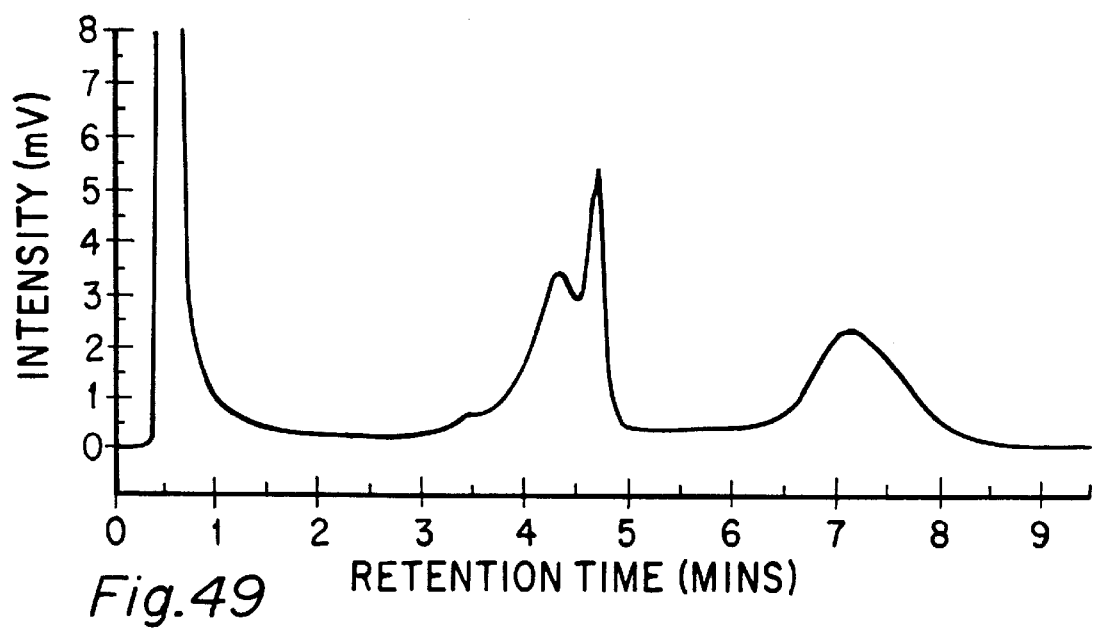
FIG. 49 is a DMIPC elution profile of a hybridized mixture containing a Lambda DNA strand containing a mutation and wild type strand.

As an example of the determination of the Mutation Separation Factor, FIG. 49 shows the resolution of the separation of the hybridized DNA mixture into heteroduplexes and homoduplexes.

The PCR conditions used with each of the primers are described in the 5 table below. All the components were combined and vortexed to ensure good mixing, and centrifuged. Aliquots were then distributed into PCR tubes as shown in the following table:

| COMPONENT | FRAGMENT |
|---|---|
| Pfu 10X Buffer | 5 µL |
| 100 µM dNTP Mix | 4 µL |
| Primer 1 (forward) | 7.5 µL |
| Primer 2 (reverse) | 8.5 µL |
| H$_2$O | 19.5 µL |
| Lambda DNA Template | 5 µL |
| Turbo Pfu | 0.5 µL |

The PCR tubes were placed into a thermocycler and the temperature cycling program was initiated. The cycling program parameters are shown in the table below:

| STEP | TEMPERATURE | TIME |
|---|---|---|
| 1 | 94° C. | 2 minutes |
| 2 | 94° C. | 1 minute |
| 3 | 58° C. | 1 minute |
| 4 | 72° C. | 1 minute |
| 6 | 72° C. | 10 minutes |
| 7 | End | |

The DMIPC conditions used for the mutation detection separations are shown below:
Eluent A: 0.1 M TEAA; Eluent B: 0.1M TEAA, 25% Acetonitrile; Flow rate: 0.900 mL/min; Gradient:

| TIME, min. | % A | % B |
|---|---|---|
| 0.0 | 50.0 | 50.0 |
| 0.1 | 45.0 | 55.0 |
| 4.6 | 36.0 | 64.0 |
| 4.7 | 0.0 | 100.0 |
| 5.2 | 0.0 | 100.0 |
| 5.3 | 50.0 | 50.0 |
| 7.8 | 50.0 | 50.0 |

The Lambda sequence has been published by O'Conner et al. in *Biophys. J* 74:A285 (1998) and by FMC Corp. at the Mutation Detection 97 $4^{th}$ International Workshop, Human Genome Organization, May 29–Jun. 2, 1997, Brno, Czech Republic, Poster no. 29. The 100 bp Lambda fragment sequence (base positions 32011–32110) used as a standard (available from FMC Corp.), the mutation was at position 32061. The chart below lists the primers used:

| Primers |
|---|
| Forward Primer: |
| 5'-GGATAATGTCCGGTGTCATG-3' (SEQ ID NO:9) |
| Reverse Primer: |
| 3'-GGACACAGTCAAGACTGCTA-5' (SEQ ID NO:8) |

Figure 48:
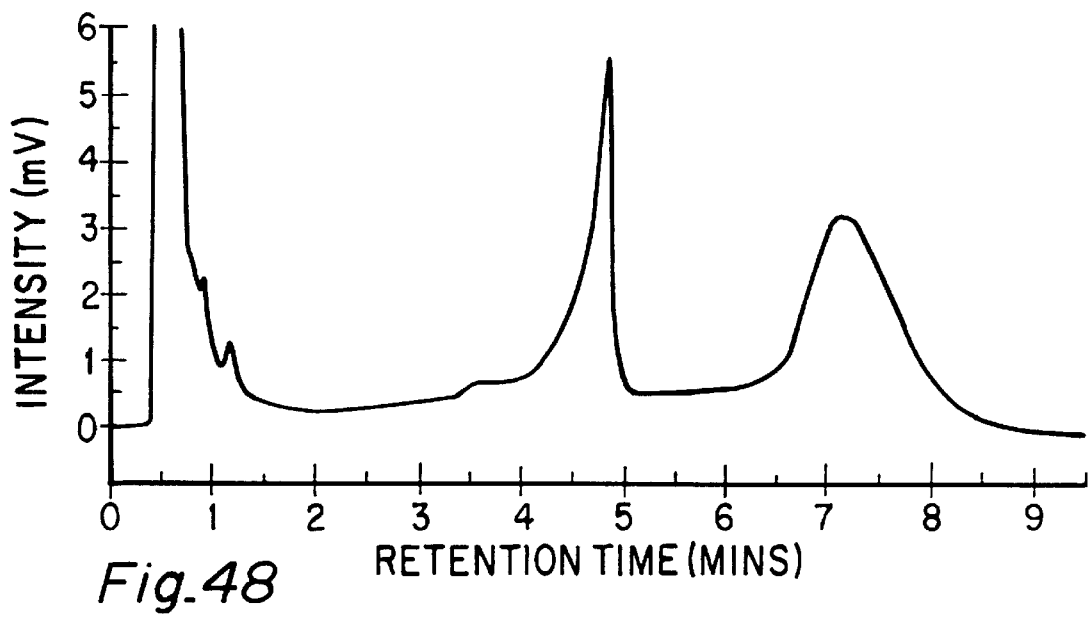
FIG. 48 is a DMIPC elution profile of a 100 bp PCR product from a wild-type strand of Lambda DNA.

FIG. 48 is a chromatogram of the wild type strand analyzed under the above conditions. The peak appearing has a retention time of 4.78 minutes and an area of 98621.

FIG. 49 is the Lambda mutation analyzed in identical conditions as FIG. 48 above. Two peaks are apparent in this chromatogram, with retention times of 4.32 and 4.68 minutes and a total area of 151246.

The Mutation Separation Factor may be calculated by applying these various peak areas to the above MSF equation. Thus, using the definition stated hereinabove, MSF=(area peak 2–area peak 1)/area peak 1, the MSF would be (151246–98621)/ 98621, or 0.533.

Example 24

Effect of Multivalent Cation Decontamination Measures on Sample Resolution by DMIPC The separation shown in FIG. 42 was obtained using a WAVE™ DNA Fragment Analysis System (Transgenomic, Inc., San Jose, Calif.) under the following conditions: Column: 50×4.6 mm i.d. containing alkylated poly(styrene-divinylbenzene) beads (DNASep®, Transgenomic, Inc.); mobile phase 0.1 M TEAA (1 M concentrate available from Transgenomic, Inc.) (Eluent A), pH 7.3; gradient: 50–53% 0.1 M TEAA and 25.0% acetonitrile (Eluent B) in 0.5 min; 53–60% B in 7 min; 60–100% B in 1.5 min; 100–50% B in 1 min; 50% B for 2 min. The flow rate was 0.9 mL/min, detection UV at 254 nm, and column temp. 56° C. The sample was 2 µL (=0.2 µg DNA, DYS271 209 bp mutation standard with an A to G mutation at position 168).

FIG. 43 is the same separation as performed in FIG. 42, but after changing the guard cartridge (20×4.0 mm, chelating cartridge, part no. 530012 from Transgenomic, Inc.) and replacing the pump-valve filter (Part no. 638-1423, Transgenomic, Inc.). The guard cartridge had dimensions of 10×3.2 mm, containing iminodiacetate chelating resin of 2.5 mequiv/g capacity and 10 µm particle size, and was positioned directly in front of the injection valve.

FIG. 44 is the same separation as performed in FIG. 43, but after flushing the column for 45 minutes with 0.1M TEAA, 25% acetonitrile, and 32 mM EDTA, at 75° C.

While the foregoing has presented specific embodiments of the present invention, it is to be understood that these embodiments have been presented by way of example only. It is expected that others will perceive and practice variations which, though differing from the foregoing, do not depart from the spirit and scope of the invention as described and claimed herein.

The invention claimed is:

1. A method for separating a sample mixture of polynucleotides by Matched Ion Polynucleotide Chromatography wherein the concentration of polynucleotides in the sample mixture is below a determined threshold concentration, the method comprising:

in a step prior to eluting the polynucleotides, accumulating the sample mixture of polynucleotides by applying the sample mixture to a Matched Ion Polynucleotide Chromotography column in a mobile phase comprising a level of organic solvent less than a level necessary to elute said polynucleotides from said column, wherein said threshold concentration is a concentration of polynucleotides that is at or below the limit of detection as determined by UV detection.

2. The method of claim 1 wherein the sample mixture is applied to the column in an aliquot of greater than 10 μL, and the mobile phase includes a counterion reagent.

3. The method of claim 1 wherein said accumulating step comprises flowing said mobile phase under isocratic conditions through said column wherein impurities are removed from said mixture.

4. A method for separating a mixture of double stranded polynucleotides, comprising flowing a mixture of polynucleotides having up to 1500 base pairs through a separation column containing polymer beads having an average diameter of 0.5 to 100 microns, wherein said beads are characterized by having a Mutation Separation Factor of at least 0.01, and separating said mixture of polynucleotides using a mobile phase comprising a counterion agent and an organic solvent, and wherein said column is substantially free from multivalent cations which are free to interfere with the separation of said polynucleotides.

5. The method of claim 1 wherein said sample mixture is applied to said column in more than one aliquot.

6. The method of claim 4 wherein said column has been subjected to treatment with multivalent cation binding agent to remove any residual surface multivalent cation metal contaminants, wherein said multivalent cations include Fe(III) or Cr(III).

7. A method for concentrating a sample mixture of polynucleotides wherein the concentration of polynucleotides in the sample mixture is below a determined threshold concentration, the method comprising:

accumulating the sample mixture of polynucleotides by applying the sample mixture to a reverse-phase column in a mobile phase comprising a level of organic solvent less than a level necessary to elute said polynucleotides from said column, wherein said threshold concentration is a concentration of polynucleotides that is at or below the limit of detection as determined by UV detection.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
acggaggttg tgaggcgctg                    20

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2

```
ctgtcatcca aatactccac acgc                                              24

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
caggcctctg attcctcatg                                                   20

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
ccactgacaa ccaccettaa cc                                                22

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
aagaattcac agggctgt                                                     18

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
taggatccag ttgcaaacca gacctcag                                          28

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
acattttcat gtcaggccac                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
atcgtcagaa ctgacacagg                                                   20

<210> SEQ ID NO 9
<211> LENGTH: 20
<212> TYPE: DNA
<213> ORGANISM: Artificial Sequence
```

-continued

```
<220> FEATURE:
<223> OTHER INFORMATION: Primer

<400> SEQUENCE: 9
ggataatgtc cggtgtcatg                                          20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
atacactgca gaacgtcagc                                          20

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gatgagttcg tgtccctaca actgg                                    25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
ggttatcgaa atcagccaca gcgcc                                    25
```